US012749554B2

(12) United States Patent
Lee et al.

(10) Patent No.: US 12,749,554 B2
(45) Date of Patent: Sep. 29, 2026

(54) MACHINE LEARNING ENABLED PREDICTION OF MOLECULAR STRUCTURES AND PROPERTIES

(71) Applicant: Genentech, Inc., South San Francisco, CA (US)

(72) Inventors: Jae Hyeon Lee, Boston, MA (US); Andrew Martin Watkins, San Francisco, CA (US); Payman Yadollahpour, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 19/092,749

(22) Filed: Mar. 27, 2025

(65) Prior Publication Data

US 2025/0253009 A1 Aug. 7, 2025

Related U.S. Application Data

(63) Continuation of application No. PCT/US2023/075236, filed on Sep. 27, 2023.

(60) Provisional application No. 63/502,753, filed on May 17, 2023, provisional application No. 63/499,333, filed on May 1, 2023, provisional application No. 63/387,680, filed on Dec. 15, 2022, provisional application No. 63/377,335, filed on Sep. 27, 2022.

(51) Int. Cl.

| | |
|---|---|
| ***G16B 15/20*** | (2019.01) |
| ***G06N 20/00*** | (2019.01) |
| ***G16B 40/20*** | (2019.01) |
| ***G16B 45/00*** | (2019.01) |

(52) U.S. Cl.

CPC ............. *G16B 15/20* (2019.02); *G06N 20/00* (2019.01); *G16B 40/20* (2019.02); *G16B 45/00* (2019.02)

(58) Field of Classification Search

None

See application file for complete search history.

(56) References Cited

U.S. PATENT DOCUMENTS

2020/0326348 A1* 10/2020 Qiao ..................... G16B 30/20

OTHER PUBLICATIONS

Pierri CL. Computational approaches for protein function prediction: a combined strategy from multiple sequence alignment to molecular docking-based virtual screening. Biochimica et Biophysica Acta 1804: 1695-1712. (Year: 2010).*

Sunny S. Protein-protein docking: past, present, and future. The Protein Journal 41: 1-26. (Year: 2022).*

Wu T. Modeling and superimposition of multiple protein structures using affine transformations: analysis of the globins. Pacific Symposia on Biocomputing: 1-12. (Year: 1998).*

Boomsma W. A generative, probabilistic model of local protein structure. PNAS 105(26): 8932-8927. (Year: 2008).*

International Searching Authority, International Search Report and Written Opinion, mailed Jan. 29, 2024, for International Patent Application No. PCT/US2023/075236.

Anand et al., 2022, "Protein Structure and Sequence Generation with Equivariant Denoising Diffusion Probabilistic Models," ARXIV.org, Cornell University Library, XP091235104.

Jumper et al., 2021, "Highly accurate protein structure prediction with AlphaFold," Nature, 596(7873):583-589.

Lee et al., 2022, "ProteinSGM: Scote-based generative modeling for de novo protein design," bioRxiv, pp. 1-20, XP093116061.

Luo et al., 2022, "Antigen-Specific Antibody Design and Optimization with Diffusion-Based Generative Models for Protein Structures," bioRxiv, pp. 1-13, XP093116063.

Daupras et al., 2022, "Robust deep learning based protein sequence design using ProteinMPNN," bioRxiv, pp. 1-33, XP093116062.

Frey et al., 2022, "Neural Scaling of Deep Chemical Models," chemRxiv.

Musaelian et al., 2022, "Learning local equivariant representations for large-scale atomistic dynamics," arXiv.

Leman, et al., 2020, "Macromolecular modeling and design in Rosetta: recent methods and frameworks," Nat Methods.

Schneider et al., 2022, "SAbDab in the age of biotherapeutics: updates including SAbDab-nano, the nanobody structure tracker," Nucleic Acids Research.

Olsen et al., 2021, "Observed Antibody Space: A diverse database of cleaned, annotated, and translated unpaired and paired antibody sequences," Protein Science.

Kabsch, 1976, "A solution for the best rotation to relate two sets of vectors," Acta Crystallographica.

Geiger and Smidt, 2022, "e3nn: Euclidean neural networks," arXiv.

Kingma et al., 2017, "Adam: A method for stochastic optimization," arXiv.

Paszke et al., 2019, "PyTorch: An imperative style, high-performance deep learning library," arXiv.

Baek et al., 2021, "Accurate prediction of protein structures and interactions using a three-track neural network," Science.

(Continued)

*Primary Examiner* — Olivia M. Wise

*Assistant Examiner* — Robert J. Kallal

(74) *Attorney, Agent, or Firm* — Jones Day

(57) ABSTRACT

A method may include receiving a molecular structure file specifying an initial three-dimensional structure of a molecule. A representation of the molecule may be determined based on the molecular structure file. For example, the representation of the molecule may include a plurality of coarse-grained nodes, each corresponding to a structural body of two or more atoms (e.g., heavy atoms) forming an amino acid residue in the molecule. Alternatively, the representation of the molecule may include, for each residue in the molecule, a plurality of frames specifying a geometric state of the backbone of the residue and one or more torsion angles in the sidechain of the residue. A design computation model may be applied to determine a three-dimensional structure of the molecule by at least modifying the representation of the molecule. The three-dimensional structure may be associated with a desirable property and/or be configured for a downstream task.

29 Claims, 18 Drawing Sheets

(56) References Cited

OTHER PUBLICATIONS

Wu et al., 2022, "High-resolution de novo structure prediction from primary sequence," bioRxiv.
Lin et al., 2022, "Language models of protein sequences at the scale of evolution enable accurate structure prediction," bioRxiv.
Chowdhury et al., 2021, "Single-sequence protein structure prediction using language models from deep learning," bioRxiv.
Meller et al., 2022, "Predicting the locations of cryptic pockets from single protein structures using the PocketMiner graph neural network," bioRxiv.
Gainza et al., 2020, "Deciphering interaction fingerprints from protein molecular surfaces using geometric deep learning," Nat Methods.
Fernández-Quintero et al., 2022, "Paratope states in solution improve structure prediction and docking," Structure.
Jing et al., 2022, "Equivariant graph neural networks for 3d macromolecular structure," arXiv.
Rocklin et al., 2017, "Global analysis of protein folding using massively parallel design, synthesis, and testing," Science.
Berman et al., 2003, "Announcing the worldwide Protein Data Bank," Nat Struct Mol Biol.
Ruffolo et al., 2022, "Antibody structure prediction using interpretable deep learning," Patterns.
Ruffolo et al., 2022, "Fast, accurate antibody structure prediction from deep learning on massive set of natural antibodies," bioRxiv.
Das, 2011, "Four small puzzles that rosetta doesn't solve," PLOS ONE.
Hsu et al., 2022, "Learning inverse folding from millions of predicted structures," bioRxiv.
Simons et al., 1999, "Ab initio protein structure prediction of CASP III targets using ROSETTA," Protein.
Del Vecchio et al., 2021, "Neural message passing for joint paratope-epitope prediction," rXiv.
Gligorijevic et al., 2021, "Structure-based protein function prediction using graph convolutional networks," Nat Commun.
Wang et al., 2022, "Scaffolding protein functional sites using deep learning," Science.
Batzner et al. 2022, "E(3)-equivariant graph neural networks for data-efficient and accurate interatomic potentials," Nat Commun.
Batatia et al., 2022, "The Design Space of E(3)-Equivariant Atom-Centered Interatomic Potentials," arXiv.
Batatia et al., 2022, "MACE: Higher order equivariant message passing neural networks for fast and accurate force fields," arXiv.
Thomas et al., 2022, "Tensor field networks: Rotation- and translation-equivariant neural networks for 3D point clouds," arXiv.
Fuchs et al., 2020, "SE(3)-Transformers: 3D Roto-Translation Equivariant Attention Networks," arXiv.
Satorras et al., 2022, "E(n) equivariant graph neural networks," arXiv.
Brandstetter et al., 2022, "Geometric and physical quantities improve E(3) equivariant message passing," arXiv.
Liao and Smidt, 2022, "Equiformer: Equivariant graph attention transformer for 3d atomistic graphs," arXiv.
Ganea et al., 2022, "Independent SE(3)-equivariant models for end-to-end rigid protein docking," In International Conference on Learning Representations.
Jin et al., 2022, "Antibody-antigen docking and design via hierarchical structure refinement," In Proceedings of the 39th International Conference on Machine Learning.

* cited by examiner

200

```
{
    "ALA": [("C", "CA", "CB", "N"), ("C", "CA", "O")],
    "ARG": [("C", "CA", "CB", "N"), ("C", "CA", "O"), ("CB", "CG", "CD"), ("NE",
"NH1", "NH2", "CZ")],
    "ASP": [("C", "CA", "CB", "N"), ("C", "CA", "O"), ("CG", "OD1", "OD2")],
    "ASN": [("C", "CA", "CB", "N"), ("C", "CA", "O"), ("CG", "ND2", "OD1")],
    "CYS": [("C", "CA", "CB", "N"), ("C", "CA", "O"), ("CA", "CB", "SG")],
    "GLU": [("C", "CA", "CB", "N"), ("C", "CA", "O"), ("CG", "CD", "OE1", "OE2")],
    "GLN": [("C", "CA", "CB", "N"), ("C", "CA", "O"), ("CG", "CD", "OE1", "NE2")],
    "GLY": [("C", "CA", "N"), ("C", "CA", "O")],
    "HIS": [("C", "CA", "CB", "N"), ("C", "CA", "O"), ("CG", "CD2", "CE1", "ND1",
"NE2")],
    "ILE": [("C", "CA", "CB", "N"), ("C", "CA", "O"), ("CB", "CG1", "CG2"), ("CB",
"CG1", "CD1")], # assumes CG1 attached to CD1
    "LEU": [("C", "CA", "CB", "N"), ("C", "CA", "O"), ("CG", "CD1", "CD2")],
    "LYS": [("C", "CA", "CB", "N"), ("C", "CA", "O"), ("CB", "CG", "CD"), ("CD",
"CE", "NZ")],
    "MET": [("C", "CA", "CB", "N"), ("C", "CA", "O"), ("CG", "CE", "SD")],
    "PHE": [("C", "CA", "CB", "N"), ("C", "CA", "O"), ("CG", "CD1", "CD2", "CE1",
"CE2", "CZ")],
    "PRO": [("C", "CA", "CB", "N"), ("C", "CA", "O"), ("CB", "CG", "CD")],
    "SER": [("C", "CA", "CB", "N"), ("C", "CA", "O"), ("CA", "CB", "OG")],
    "THR": [("C", "CA", "CB", "N"), ("C", "CA", "O"), ("CB", "CG2", "OG1")],
    "TRP": [("C", "CA", "CB", "N"), ("C", "CA", "O"), ("CG", "CD1", "CD2", "CE2",
"CE3", "CZ2", "CZ3", "CH2", "NE1")],
    "TYR": [("C", "CA", "CB", "N"), ("C", "CA", "O"), ("CG", "CD1", "CD2", "CE1",
"CE2", "CZ", "OH")],
    "VAL": [("C", "CA", "CB", "N"), ("C", "CA", "O"), ("CB", "CG1", "CG2")]
}
```

FIG. 2A

250

```
cg_dict = {
    "ALA": [("C", "CA", "HA", "CB", "1HB", "2HB", "3HB", "N"), ("CA", "N", "H"), ("C", "CA", "O")],
    "ARG": [("C", "CA", "HA", "CB", "N"), ("CA", "N", "H"), ("C", "CA", "O"), ("CG", "1HB", "2HB"),
("CD", "1HG", "2HG"), ("NE", "1HD", "2HD"), ("CZ", "HE", "NH1", "NH2", "1HH1", "2HH1",
"1HH2", "2HH2")],
    "ASP": [("C", "CA", "HA", "CB", "N"), ("CA", "N", "H"), ("C", "CA", "O"), ("CG", "1HB", "2HB"),
("CG", "OD1", "OD2")],
    "ASN": [("C", "CA", "HA", "CB", "N"), ("CA", "N", "H"), ("C", "CA", "O"), ("CG", "1HB", "2HB"),
("ND2", "OD1", "1HD2", "2HD2")],
    "CYS": [("C", "CA", "HA", "CB", "N"), ("CA", "N", "H"), ("C", "CA", "O"), ("SG", "1HB", "2HB"),
("CB", "SG", "HG")],
    "GLU": [("C", "CA", "HA", "CB", "N"), ("CA", "N", "H"), ("C", "CA", "O"), ("CG", "1HB", "2HB"),
("CD", "1HG", "2HG"), ("CD", "OE1", "OE2")],
    "GLN": [("C", "CA", "HA", "CB", "N"), ("CA", "N", "H"), ("C", "CA", "O"), ("CG", "1HB", "2HB"),
("CD", "1HG", "2HG"), ("OE1", "NE2", "1HE2", "2HE2")],
    "GLY": [("C", "CA", "1HA", "2HA", "N"), ("CA", "N", "H"), ("C", "CA", "O")],
    "HIS": [("C", "CA", "HA", "CB", "N"), ("CA", "N", "H"), ("C", "CA", "O"), ("CG", "1HB", "2HB"),
("CD2", "HD2", "CE1", "HE1", "ND1", "NE2"), ("HN", "NH", "NN")], # NH: the nitrodgen with the
H, NN: the nitrogen without
    "ILE": [("C", "CA", "HA", "CB", "N"), ("CA", "N", "H"), ("C", "CA", "O"), ("CG1", "CG2", "HB",
"1HG2", "2HG2", "3HG2"), ("CD1", "1HG1", "2HG1", "1HD1", "2HD1", "3HD1")],
    "LEU": [("C", "CA", "HA", "CB", "N"), ("CA", "N", "H"), ("C", "CA", "O"), ("CG", "1HB", "2HB"),
("CD1", "CD2", "HG", "1HD1", "2HD1", "3HD1", "1HD2", "2HD2", "3HD2",)],
    "LYS": [("C", "CA", "HA", "CB", "N"), ("CA", "N", "H"), ("C", "CA", "O"), ("CG", "1HB", "2HB"),
("CD", "1HG", "2HG"), ("CE", "1HD", "2HD"), ("NZ", "1HE", "2HE", "1HZ", "2HZ", "3HZ")],
    "MET": [("C", "CA", "HA", "CB", "N"), ("CA", "N", "H"), ("C", "CA", "O"), ("CG", "1HB", "2HB"),
("SD", "1HG", "2HG"), ("CE", "1HE", "2HE", "3HE")], # adventurously allow MET a chi4!
    "PHE": [("C", "CA", "HA", "CB", "N"), ("CA", "N", "H"), ("C", "CA", "O"), ("CG", "1HB", "2HB"),
("CD1", "HD1" "CD2", "HD2", "CE1", "HE1", "CE2", "HE2", "CZ", "HZ")],
    "PRO": [("C", "CA", "HA", "CB", "N"), ("C", "CA", "O"), ("CG", "1HB", "2HB"), ("CD", "1HG",
"2HG"), ("CD", "1HD", "2HD")], # no ("CA", "N", "H") for you!
    "SER": [("C", "CA", "HA", "CB", "N"), ("CA", "N", "H"), ("C", "CA", "O"), ("OG", "1HB", "2HB"),
("CB", "OG", "HG")],
    "THR": [("C", "CA", "HA", "CB", "N"), ("CA", "N", "H"), ("C", "CA", "O"), ("OG1", "CG2", "HB",
"1HG2", "2HG2", "3HG2"), ("CB", "OG1", "HG1")],
    "TRP": [("C", "CA", "HA", "CB", "N"), ("CA", "N", "H"), ("C", "CA", "O"), ("CG", "1HB", "2HB"),
("CD1", "HD1", "CD2", "CE2", "CE3", "HE3", "CZ2", "HZ2", "CZ3", "HZ3", "CH2", "HH2" "NE1",
"HE1")],
    "TYR": [("C", "CA", "HA", "CB", "N"), ("CA", "N", "H"), ("C", "CA", "O"), ("CG", "1HB", "2HB"),
("CD1", "HD1", "CD2", "HD2", "CE1", "HE1", "CE2", "HE2", "CZ", "OH"), ("CZ", "OH", "HH")],
    "VAL": [("C", "CA", "HA", "CB", "N"), ("CA", "N", "H"), ("C", "CA", "O"), ("CG", "1HB", "2HB",
"CG1", "CG2", "1HG1", "2HG1", "3HG1", "1HG2", "2HG2", "3HG2")]
}
```

FIG. 2B

MACHINE LEARNING ENABLED PREDICTION OF MOLECULAR STRUCTURES AND PROPERTIES

CROSS REFERENCE TO RELATED APPLICATIONS

This application is of bypass continuation of International Patent Application No. PCT/US2023/075236, entitled "MACHINE LEARNING ENABLED PREDICTION OF MOLECULAR STRUCTURES AND PROPERTIES" and filed on Sep. 27, 2023, which claims priority to U.S. Provisional Application No. 63/377,335, entitled "MACHINE LEARNING ENABLED PREDICTION OF MOLECULAR STRUCTURES AND PROPERTIES" and filed on Sep. 27, 2022, U.S. Provisional Application No. 63/387,680, entitled "MACHINE LEARNING ENABLED PREDICTION OF MOLECULAR STRUCTURES AND PROPERTIES" and filed on Dec. 15, 2022, U.S. Provisional Application No. 63/499,333, entitled "MACHINE LEARNING ENABLED PREDICTION OF MOLECULAR STRUCTURES AND PROPERTIES" and filed on May 1, 2023, and U.S. Provisional Application No. 63/502,753, entitled "MACHINE LEARNING ENABLED PREDICTION OF MOLECULAR STRUCTURES AND PROPERTIES" and filed on May 17, 2023. The disclosures of the foregoing applications are incorporated herein by reference in their entirety.

TECHNICAL FIELD

The subject matter described herein relates generally to molecular design and more specifically to machine learning based techniques for predicting molecular structures and properties.

INTRODUCTION

A molecule is a group of two more atoms held together by chemical bonds. Molecules form the smallest identifiable unit into which a pure substance can be divided while still retaining the composition and chemical properties of that substance. One example of a molecule is a protein molecule while examples of non-protein molecules include small molecules, ions, nucleic acids, polysaccharides, glycolipids, and/or the like. The function and properties of a molecule may be contingent upon its three-dimensional structure. For example, proteins are responsible for many essential cellular functions including, for example, enzymatic reactions, transport of molecules, regulation and execution of a number of biological pathways, cell growth, proliferation, nutrient uptake, morphology, motility, intercellular communication, and/or the like. A protein structure may include one or more polypeptides, which are chains of amino acid residues linked together by peptide bonds. The sequence of amino acid residues in the polypeptide chains forming the protein structure determines the protein's three-dimensional structure (e.g., the protein's tertiary structure). Moreover, the sequence of amino acids in the polypeptide chains forming the protein determines the protein's underlying functions. As such, one objective of de novo protein design includes constructing one or more sequences of amino acid residues that exhibit desirable properties and not undesirable ones. For instance, in the case of large molecule drug discovery, de novo protein design will often seek to identify sequences of amino acid residues (e.g., antibodies and/or the like) capable of binding to an antigen such as a viral antigen, a tumor antigen, and/or the like.

SUMMARY

Systems, methods, and articles of manufacture, including computer program products, are provided for molecular structure and property prediction. In one aspect, there is provided a system for molecular structure and property prediction. The system may include at least one processor and at least one memory. The at least one memory may include program code that provides operations when executed by the at least one processor. The operations may include: receiving a molecular structure file specifying an initial three-dimensional structure of a protein molecule comprising a first sequence of amino acid residues; determining, based at least on the molecular structure file, a representation of the protein molecule that includes a plurality of frames for each amino acid residue in the first sequence of amino acid residues, the plurality of frames for each amino acid residue including a first set of frames specifying a geometric state a backbone of the amino acid residue, and the plurality of frames of each amino acid residue further including a second set of frames specifying one or more torsion angles in a sidechain of the amino acid residue; and generating a first three-dimensional structure of the protein molecule by at least applying a design computation model to modify the representation of the protein molecule.

In another aspect, there is provided a method for molecular structure and property prediction. The method may include: receiving a molecular structure file specifying an initial three-dimensional structure of a protein molecule comprising a first sequence of amino acid residues; determining, based at least on the molecular structure file, a representation of the protein molecule that includes a plurality of frames for each amino acid residue in the first sequence of amino acid residues, the plurality of frames for each amino acid residue including a first set of frames specifying a geometric state a backbone of the amino acid residue, and the plurality of frames of each amino acid residue further including a second set of frames specifying one or more torsion angles in a sidechain of the amino acid residue; and generating a first three-dimensional structure of the protein molecule by at least applying a design computation model to modify the representation of the protein molecule.

In another aspect, there is provided a computer program product for molecular structure and property prediction. The computer program product may include a non-transitory computer readable medium storing instructions that cause operations when executed by at least one data processor. The operations may include: receiving a molecular structure file specifying an initial three-dimensional structure of a protein molecule comprising a first sequence of amino acid residues; determining, based at least on the molecular structure file, a representation of the protein molecule that includes a plurality of frames for each amino acid residue in the first sequence of amino acid residues, the plurality of frames for each amino acid residue including a first set of frames specifying a geometric state a backbone of the amino acid residue, and the plurality of frames of each amino acid residue further including a second set of frames specifying one or more torsion angles in a sidechain of the amino acid residue; and generating a first three-dimensional structure of the protein molecule by at least applying a design computation model to modify the representation of the protein molecule.

In some variations of the methods, systems, and non-transitory computer readable media, one or more of the following features can optionally be included in any feasible combination.

In some variations, each frame of the plurality of frames may correspond to a degree-of-freedom for the design computation model to update the initial three-dimensional structure of the protein molecule.

In some variations, the first set of frames may include a first frame comprising an affine transformation matrix specifying a rotation and a translation of the backbone of the amino acid residue. The first set of frames may further include a second frame specifying a torsion angle in the backbone of the amino acid residue.

In some variations, the first set of frames may include a first frame specifying a first torsion angle in the backbone of the amino acid residue. The first set of frames may further include a second frame specifying a second torsion angle in the backbone of the amino acid residue.

In some variations, wherein the first torsion angle may be associated with a first rotatable bond between an alpha carbon (Ca) atom and a carbon (C) atom in the backbone in the backbone of the amino acid residue. The second torsion angle may be associated with a second rotatable bond between the alpha carbon (Ca) atom and a nitrogen (N) atom in the backbone of the of the amino acid residue.

In some variations, the first set of frames may further include a third frame specifying a third torsion angle present in the backbone of the amino acid residue. The third torsion angle may be associated with a third rotatable bond between the carbon (C) atom and the nitrogen (N) atom in the backbone of the amino acid residue.

In some variations, one or more coordinates of a plurality of backbone atoms in the protein molecule may be determined based at least on the plurality of frames associated with each amino acid residue included in the modified representation of the protein molecule. One or more coordinates of a plurality of sidechain atoms in the protein molecule may be determined based on the one or more coordinates of the plurality of backbone atoms in the protein molecule.

In some variations, the design computation model may include a machine learning model trained to generate the first three-dimensional structure of the protein molecule by at least to denoising the initial three-dimensional structure of the protein molecule.

In some variations, the machine learning model may denoise the initial three-dimensional structure of the protein molecule by at least performing a sequence of updates to the representation of the protein molecule.

In some variations, the machine learning model may be trained to reduce a loss function and/or an energy function associated with each successive update to the initial three-dimensional structure of the protein molecule.

In some variations, the machine learning model may be a diffusion model that removes, at each timestep of a plurality of successive timesteps, a portion of noise present in the initial three-dimensional structure of the protein molecule.

In some variations, the diffusion model may perform a first update to the representation of the protein molecule in order to remove a first quantity of noise present in the initial three-dimensional structure of the protein molecule. The diffusion model may further perform a second update to the representation of the protein molecule in order to remove a second quantity of noise present in the initial three-dimensional structure of the protein molecule.

In some variations, the diffusion model may further add a third quantity of noise prior to performing the second update to remove the second quantity of noise and a fourth quantity of noise subsequent to performing the second update to remove the second quantity of noise. The third quantity of noise and the fourth quantity of noise may be determined based on a noise schedule defining a distribution of noise levels that is added across the plurality of successive timesteps.

In some variations, the distribution of noise levels may correspond to a degree-of-freedom present in the representation of the protein molecule for the computation model to modify the initial three-dimensional structure of the protein molecule.

In some variations, each update performed by the diffusion model may generate an output that is equivariant to special Euclidean group SE(3) transformations.

In some variations, the modifying of the representation of the protein molecule may include updating the first set of frames to alter the geometric state of the backbone of one or more amino acid residues in the protein molecule.

In some variations, the modifying of the representation of the protein molecule may include updating the second set of frames to alter the one or more torsion angles in the sidechain of one or more amino acid residues in the protein molecule.

In some variations, the first three-dimensional structure of the protein molecule may be associated with one or more desirable properties.

In some variations, the first three-dimensional structure of the protein molecule may be configured for one or more downstream tasks.

In some variations, the first sequence of amino acid residues may be determined to exhibit a desirable three-dimensional structure and/or a desirable property based at least on the first three-dimensional structure of the protein molecule. In response to determining that the first sequence of amino acid residues exhibits the desirable three-dimensional structure and/or the desirable property, a second sequence of amino acid residues for a different protein molecule may be generated based at least on the first sequence of amino acid residues.

In some variations, the representation of the protein molecule may further include, for each position in a sequence of amino acid residue forming the protein molecule, a logic vector indicating an identity of an amino acid residue occupying the position by at least enumerating a probability distribution across a set of possible amino acid residues occupying the position.

In some variations, the design computation model may further generate the first three-dimensional structure of the protein molecule by modifying an identity of at least one amino acid residue in the first sequence of residues while modifying the first set of frames and/or the second set of frames associated with the at least one amino acid residue.

In some variations, the initial three-dimensional structure of the protein molecule may include noise in an identity of each amino acid residue and/or a spatial arrangement of a plurality of atoms forming each amino acid. The noise may be removed by the design computation model modifying the representation of the protein molecule.

In some variations, the representation of the protein molecule may be further generated to include a plurality of polymer chains. Each polymer chain may include one or more amino acid residues from the first sequence of amino acid residues. The representation of the protein molecule may be modified by the protein design computation model modifying a position of the one or more amino acid in each polymer chain as a group.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a non-transitory computer-readable or machine-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including, for example, to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to protein design, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 2A depicts an example of a coarse-node representation of a protein sequence from which hydrogen (H) atoms are excluded, in accordance with some example embodiments;

FIG. 2B depicts another example of a coarse-node representation of a protein sequence including hydrogen (H) atoms, in accordance with some example embodiments;

When practical, similar reference numbers denote similar structures, features, or elements.

DETAILED DESCRIPTION

Figure 1A:
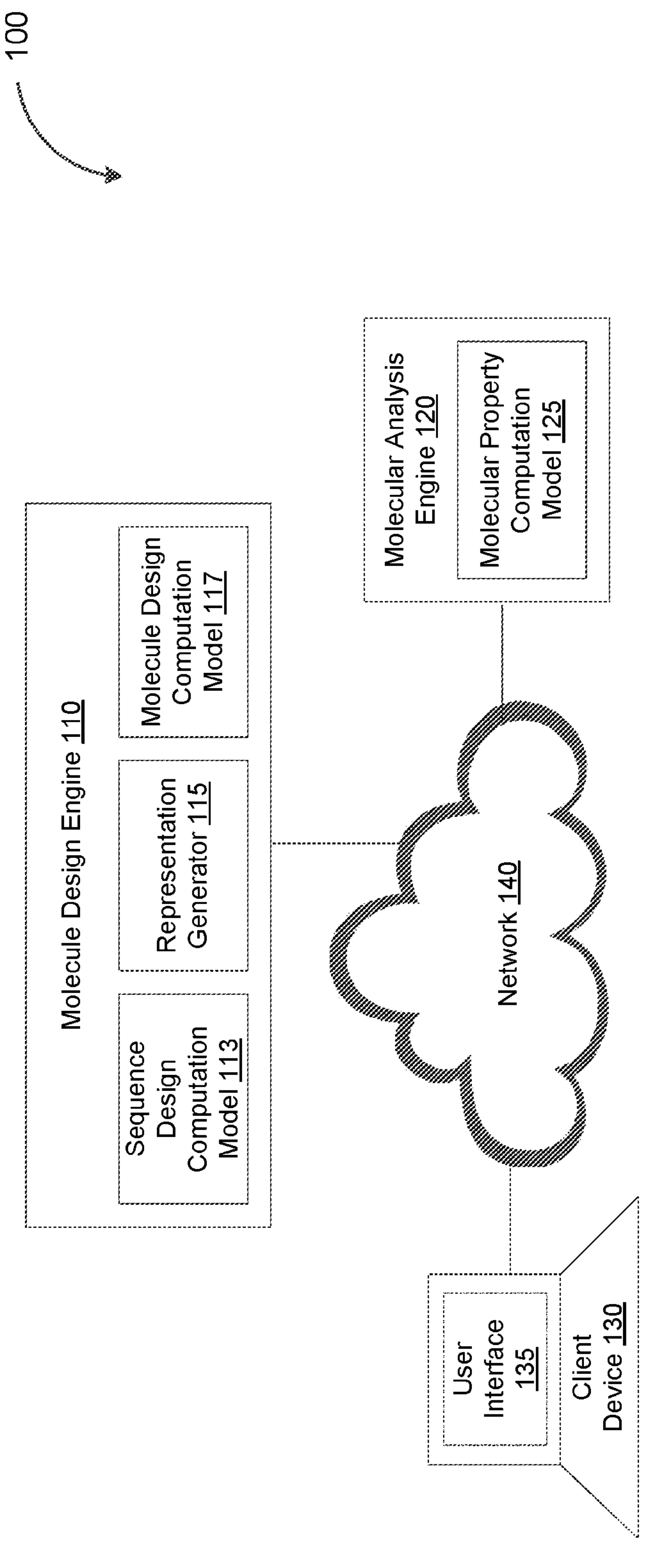
FIG. 1A depicts a system diagram illustrating an example of a molecule design system, in accordance with some example embodiments.

The properties of a molecule may be contingent upon its composition as well as structure. For example, the properties of a small molecule, including its safety and efficacy as a therapeutic, may depend on the quantity of atoms of each constituent element (e.g., molecular or empirical formula) as well as the bonding arrangement between these atoms (e.g., structural formula). Meanwhile, the properties of a large molecule, such as a the binding affinity and developability of a protein molecule, may be determined by the sequence of amino acid residues forming the large molecule and the three-dimensional structure adopted by that sequence of amino acid residues. Accordingly, the development of small and large molecule therapeutics contemplates the composition and structure of each candidate molecule.

In the case of protein design, where a key objective includes identifying protein sequences (e.g., sequences of amino acid residues) that exhibit certain desirable properties, insights into the properties of a protein molecule may be limited without first determining its three-dimensional structure. As such, the task of protein structure prediction, which includes inferring the three-dimensional structure of a protein molecule based on the sequence of amino acid sequence forming protein molecule, may be a critical component of protein design. Contrastingly, structurally agnostic prediction of protein sequences may yield many protein sequences that are unable to adopt a three-dimensional structure capable of binding with a target molecule. In this context, the sequence of amino acid residues forming a protein molecule may also be known as the primary structure of the protein molecule. The three-dimensional structure of the protein molecule includes the one or more secondary structures that are formed when individual amino acid residues are linked by hydrogen bonds as well as the tertiary structure that is formed when the secondary structures are disposed along a single polypeptide chain known as the backbone of the protein molecule.

While an integrated design approach that combines sequence and structure design may yield protein molecules that are more likely to exhibit desirable properties such as binding affinity and developability, innumerable variations exist in the sequence and three-dimensional structure of protein molecules. For example, the solution space occupied by every possible permutation of amino acid residues that can form a protein molecule is vast (e.g., approximately $20^N$ for a protein sequence of N amino acid residues) even though few of those possible permutations actually correspond to functional protein sequences. Meanwhile, a single sequence of amino acid residues may fold into numerous different three-dimensional structures. In some cases, due to its flexible nature, the three-dimensional structure of a protein molecule may even evolve over time, particularly as the protein molecule comes into close proximity to and interacts with another molecule. Each three-dimensional structure or conformation of the protein molecule may include a different spatial arrangement of the atoms in each constituent amino acid residue. As such, the solution space populated by every possible three-dimensional structure that can be formed by just single sequence of amino acid residues is already incredibly immense even when confined to several discrete (instead of continuous) structural variations. For instance, a protein sequence of N amino acid residues may have approximately $3^N$ possible conformations even if each amino acid residue is limited to assuming one of three discrete geometric states (e.g., rotamers). For protein sequences of a meaningful length, a brute force search of the solution space for every possible permutation of amino acid residues combined with the solution space for every possible three-dimensional structure is computationally intractable. The strain on computational resources is further exacerbated by conventional approaches to structural bioinformatics, which are painstakingly slow due to various computational inefficiencies. For at least the foregoing reasons, current efforts to engineer protein sequences capable of adopting a certain three-dimensional structure are constrained by a challenging tradeoff between functional output protein designs and computational burden.

The present disclosure eliminates the tradeoff between generating functional protein designs and computational burden by strategically reducing the joint solution space of integrated sequence and structural design. For example, in some cases, the design of a molecule, such as a protein molecule, may be performed on a representation of the molecule that enhances the performance of various design computation models. In this context, the representation of a molecule may include a structural representation of the three-dimensional structure of the molecule, which indicates the spatial arrangement of the atoms forming the molecule. For instance, where the molecule is a protein molecule, the structural representation of the molecule may indicate the spatial arrangement of the atoms forming each amino acid residue in the molecule. In instances where the molecule is a protein molecule, the representation of the molecule may also include a sequence representation indicating the identity of each amino acid residue forming the molecule.

As described in more detail below, the sequence (e.g., the primary structure) and the three-dimensional structure (e.g., the secondary structure and tertiary structure) of a protein molecule may be determined by applying a computation model to a representation of the protein molecule. For example, in some cases, the sequence and the three-dimensional structure of the protein molecule may be determined by the computation model applying a succession of modifications to the representation of the protein molecule. In some cases, the representation of the protein molecule may impose certain limitations on the individual modifications that may be made by the computation model to the sequence and three-dimensional structure of the protein molecule. For instance, in some cases, the structural representation of the protein molecule may prevent arbitrary and unviable modifications to the position of individual atoms in three-dimensional space. Thus, the computation model operating on the representation of the protein molecule may strategically reduce the joint solution space searched by the computation model to generate the sequence and structure of the protein molecule with minimal detriment to the accuracy of the design outcomes.

Figure 3A:
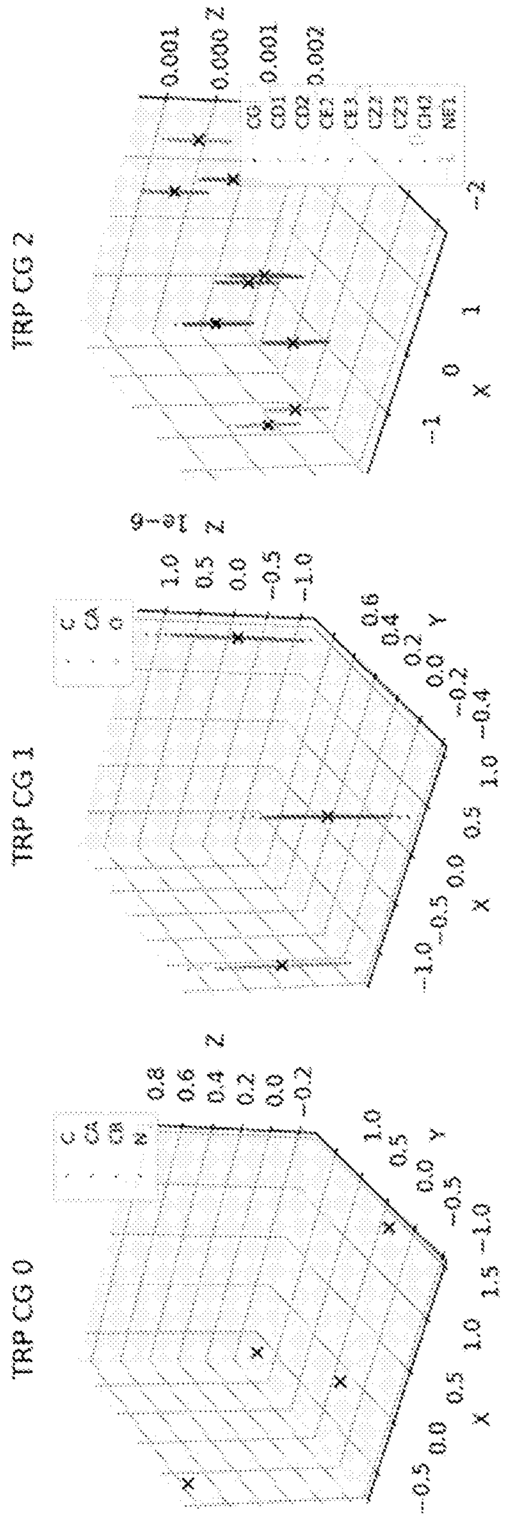
FIG. 3A depicts a visualization of the relative positions of the atoms in the coarse-grained nodes associated with the amino acid residue tryptophan (Trp), in accordance with some example embodiments.
Figure 3B:
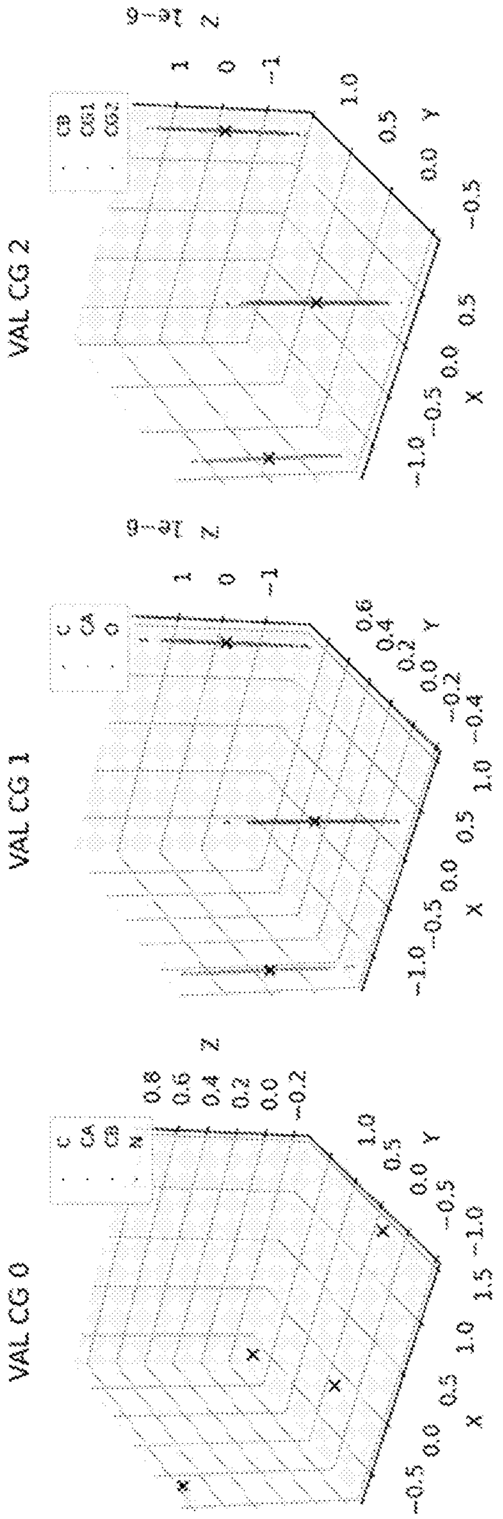
FIG. 3B depicts a visualization of the relative positions of the atoms in the coarse-grained nodes associated with the amino acid residue valine (Val), in accordance with some example embodiments.

In some example embodiments, the structural representation of a molecule, such as a protein molecule, may be a coarse-grained (CG) node representation (as illustrated at FIGS. 3A and 3B). That is, in some cases, the three-dimensional structure of a molecule, including the positions (e.g., three-dimensional coordinates) of every atom included in the molecule, may be represented as a collection of coarse-grained (CG) nodes. Although the molecule may be a protein molecule, it should be appreciated that the molecule may also be a non-protein molecule (e.g., a small molecule, a nucleic acid, a polysaccharide, a glycolipid, and/or the like). In the case of a protein molecule, each amino acid residue included in the protein molecule may include one or more representative structural bodies including, for example, rigid bodies, flexible or variable bodies, and/or the like. Moreover, each amino acid residue in the protein molecule may be represented by a set of coarse-grained nodes, each of which corresponding to one of the structural bodies forming the amino acid residue. As a rigid body, a single structural body may include a group of two or more atoms whose locations are fixed with respect to the coordinates of the structural body. As a flexible or variable body, a single structural body may include a group of two or more atoms whose locations are flexible to a certain degree relative to the coordinates of the structural body. As such, each coarse-grained node associated with an amino acid residue may include the atoms included in a corresponding structural body. In some cases, a single atom may be a part of multiple structural bodies of the amino acid residue and thus be included in multiple corresponding coarse-grained nodes. Moreover, the positions of the constituent atoms in an amino acid residue may be specified by a rotation R and/or a translation T of the corresponding coarse-grained node.

In some example embodiments, the structure of the molecule, such as a protein molecule, may be represented by the coordinate transformations (e.g., Euclidean transformations) and the geometric tensor embedding of each coarse-grained node associated with the molecule. For example, in some cases, the rotation R and/or the translation T of each coarse-grained node associated with the molecule may be represented as a set of geometric tensors (or geometric tensor embeddings) with each geometric tensor having a configurable maximum degree L. As used herein, the term "geometric tensor" may refer to an object (e.g., a scalar, a vector, and/or the like) that transforms when subjected to one or more coordinate transformations (e.g., Euclidean transformations) such as rotation, translation, and/or the like. In some instances, the set of geometric tensors associated with a coarse-grained node may be subjected to coordinate transformations corresponding to one or more group elements of the three-dimensional rotation group. The aforementioned three-dimensional rotation group may describe the possible rotational symmetries and orientations of the structural body in a multi-dimensional space (e.g., a three-dimensional space and/or the like). In this context, each group element of the three-dimensional rotation group may be represented as one or more irreducible representations that cannot undergo further decomposition. Accordingly, the geometric tensor embedding of the coarse grained node may include the set of geometric tensors, each of which being steered according to one or more group elements from the three-dimensional rotation group to describe the current translation and rotation of the corresponding structural body. The coarse-grained (CG) node representation of a molecule, such as a protein molecule, may reduce the joint solution space searched by a computational model by at least avoiding modifications to the position of each individual atom within the molecule. Instead, while a computation model is operating on a coarse-grained (CG) node representation of a molecule, the computation model may apply Euclidean transformations (e.g., translations and rotations) to groups of two or more atoms that are more likely to move as a collective whole.

Figure 6A:
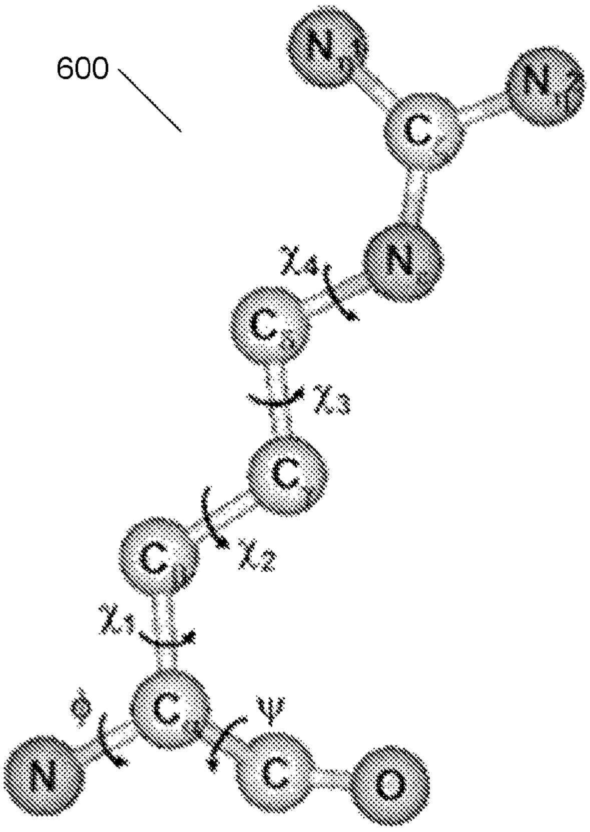
FIG. 6A depicts a schematic diagram illustrating an atomic structure of an example of an amino acid residue, in accordance with some example embodiments.

In some example embodiments, the structural representation of a molecule, such as a protein molecule, may be a backbone torsion (BBT) representation (as illustrated at FIG. 6A). For example, in the case of a protein molecule, the backbone torsion (BBT) representation of the protein molecule may include, for each constituent amino acid residue of the protein molecule, a plurality of frames defining the positions of the atoms forming the amino acid residue by at least specifying the geometric states the backbone and sidechains of the amino acid residue. In some cases, the plurality of frames may include a first set of frames specifying a geometric state of the backbone of the corresponding amino acid residue. As used herein, the "backbone" of an amino acid residue may include the atoms that are common to every amino acid residue (e.g., a nitrogen (N) atom, an alpha carbon (Ca), and a carboxyl carbon (C) atom). Furthermore, the plurality of frames may include a second set of frames specifying one or more torsion angles present in a sidechain of the amino acid residue. As used herein, the term "torsion angle," which may be used interchangeably with the term "dihedral angle," may refer to an angle describing the rotation of around the center bond of a fragment of a polypeptide chain that includes four atoms coupled by three consecutive bonds.

For a single amino acid residue containing a plurality of atoms, each frame may define a mapping between the position of the atoms in three-dimensional space (e.g., the three-dimensional coordinates of each atom) to one or more internal degrees of freedom (DoF). In this context, an internal degree-of-freedom (DoF) may refer to a constraint on the type and/or extent of the modifications that may be made to the amino acid residue, for example, by a computation model, when determining the sequence and/or three-dimensional structure of a protein molecule containing the amino acid residue. For example, in some cases, some degrees of freedom (DoF) may limit the changes to the identity of the amino acid residue to one of the 20 canonical amino acid residues. Alternatively and/or additionally, some degrees of freedom (DoF), such as backbone translation, backbone rotation, and torsion angles, may impose constraints upon the spatial range within which each atom in the amino acid residue is able to move as a part of the overall three-dimensional structure of the amino acid residue. That is, some frames may limit the manner and extent to which each atom can be rearranged in three-dimensional space, for example, relative to other atoms in the amino acid residue, thus preventing the atoms from being able to move freely to any arbitrary location (e.g., coordinates) in three-dimensional space. In the case of backbone translation and rotation, for example, the corresponding degrees of freedom (DoF) may require the backbone atoms of the amino acid residue to be translated and rotated as a group, thus preventing the individual backbone atoms from being moved to change the relative spatial arrangement therebetween. For the torsion angle between two sidechain atoms connected by a bond, the corresponding degree of freedom (DoF) may require one atom to rotate about the other atom without any changes to the distance (or bond length) therebetween. As described in more detail below, each frame may correspond to a degree-of-freedom (DoF) for a computation model to update a protein sequence (e.g., the identities of the constituent amino acid residues) and/or the three-dimensional structure of the protein sequence.

In some example embodiments, the backbone torsion (BBT) representation of the protein molecule may specify the geometric state of the backbone of each amino acid residue in a variety of different ways. For example, in some cases, the geometric state of the backbone of an amino acid residue may be specified based on its translation and rotation as well as a second torsion angle of a rotatable bond between an alpha carbon (Ca) atom and a carbonyl group in the backbone of the amino acid residue. Accordingly, in some cases, the first set of frames may include a first frame specifying a rotation and a translation of the backbone of the amino acid residue. For instance, in some cases, the first frame may include an affine transformation matrix that includes a rotation matrix specifying the rotation of the backbone of the amino acid residue as well as a displacement vector specifying the translation of the backbone of the amino acid residue. In instances where the first frame specifies the rotation and the translation of the backbone of the amino acid residue, the first set of frames may further include a second frame specifying a torsion angle (e.g., of the rotatable bond between the alpha carbon (Ca) atom and the carbonyl group) in the backbone of the amino acid residue.

In some example embodiments, instead of the geometric state of the backbone of an amino acid residue being specified based a combination of torsion angle and its translation and rotation, the geometric state of the backbone of the amino acid residue may also be specified based on the torsion angles present in the backbone of the amino acid residue. Accordingly, in some cases, the first set of frames may include a first frame specifying a torsion angle of the rotatable bond between the alpha carbon (Ca) atom and the carbonyl group in the backbone of the amino acid residue. Moreover, in those instances, the first set of frames may further include a third frame and a fourth frame. The third frame may specify the third torsion angle of the rotatable bond between the alpha carbon (Ca) atom and the nitrogen (N) atom in the backbone of the of the amino acid residue. Meanwhile, the fourth frame may specify the fourth torsion angle of the rotatable bond between the carbon (C) atom and the nitrogen (N) atom in the backbone of the amino acid residue.

In some example embodiments, the three-dimensional structure of a molecule, such as a protein molecule, may be determined by at least applying a computation model to modify the representation of an initial three-dimensional structure of the molecule. For example, in some cases, the computation model may modify the structural representation (e.g., the coarse-grained (CG) node representation, the backbone torsion (BBT) representation, and/or the like) of the molecule to determine the three-dimensional structure of the molecule. Alternatively and/or additionally, in the case of protein design, the computation model may, along with modifying the structural representation of the molecule, also modify the sequence representation of the molecule to determine the identities of the amino acid residues forming the molecule. It should be appreciated that the initial three-dimensional structure of the molecule may include varying degrees of entropy, which decreases as the molecule undergo modification by the computation model. For instance, in some cases, the initial three-dimensional structure of the molecule may include at least some noise (e.g., Gaussian noise and/or the like) in the positions (e.g., the three-dimensional coordinates) of the constituent atoms. In instances where the molecule is a protein molecule, the initial three-dimensional structure of the molecule may include one or more groupings of amino acid residues corresponding to one or more polymer chains present in the molecule.

In some cases, the three-dimensional structure of the molecule may be determined by at least determining, based at least on the modified representation of the molecule output by the computation model, one or more coordinates of each atom in the three-dimensional structure of the molecule. For example, in instances where the molecule is a protein molecule whose three-dimensional structure is rendered in a backbone torsion (BBT) representation, the one or more coordinates of each atom in the three-dimensional structure of the molecule may be determined based at least on the plurality of frames associated with each amino acid residue included in the modified representation of the molecule output by the computation model. In some cases, the one or more coordinates of each atom in the three-dimensional structure of the molecule may be determined by at least determining the one or more coordinates of a plurality of backbone atoms in the molecule. Moreover, in some cases, the one or more coordinates of each atom in the three-dimensional structure of the molecule may be further determined by at least determining, based on the one or more coordinates of the plurality of backbone atoms in the molecule, the one or more coordinates of a plurality of sidechain atoms in the molecule.

In some example embodiments, where the three-dimensional structure of a protein molecule is rendered in a coarse-grained (CG) node representation, the three-dimensional structure of the protein molecule may be determined by applying the computation model to the tensors associated with each coarse-grained node in the molecule. For example, the structure computation model may receive an input that includes, for each coarse-grained (CG) node in the protein molecule, a set of geometric tensors representative of the rotation R and/or the translation T of the coarse-grained (CG) node in the initial three-dimensional structure of the protein molecule. Furthermore, the computation model may perform successive updates on the rotation R and/or translation T of one or more of the coarse-grained nodes in an initial three-dimensional structure in order to derive the three-dimensional structure of the molecule. Alternatively, as noted, the computation model may generate the three-dimensional structure of the molecule by at least modifying one or more frames in the backbone torsion (BBT) representation of the molecule. For instance, in the case of protein design, the computation model may ingest an input that includes, for each amino acid residue in a protein sequence, a representation of the identity of the amino acid residue, a translation of the backbone atoms, a rotation of the backbone atoms, and one or more torsion angles. In some cases, the computation model may, along with modifying the structural representation of the molecule (e.g., the coarse-grained (CG) node or backbone torsion (BBT) representation of the molecule) to determine the three-dimensional structure of the molecule, also modify the sequence representation of the molecule in order to determine the sequence of amino acid residues forming the molecule (e.g., the primary structure of the molecule). In some cases, the computation model may generate the three-dimensional structure of the molecule to exhibit one or more desirable properties, such as binding affinity towards another molecule (e.g., a viral antigen, a tumor antigen, and/or the like), specificity towards another molecule, lack of nonspecificity, stability (e.g., conformation stability, thermodynamic stability, robustness to different environmental stresses such as protease resistance, and/or the like), non-immunogenicity, human-ness, absence of self-association (or non-aggregation), lack of chemical liabilities (e.g., aspartate isomerization, oxidation, deamidation), developability, and/or the like. Alternatively and/or additionally, the three-dimensional structure of the molecule may be one that is suitable or configured for one or more downstream tasks such as a predictive analysis of the various properties exhibited by the molecule.

In some example embodiments, the computation model may be a machine learning model capable of recognizing the same three-dimensional structure regardless of the orientation of the three-dimensional structure ingested as input. For example, in some cases, the computation model may be implemented as a geometric deep learning model such as an equivariant neural network (ENN), a multi-body higher order equivariant message passing neural network, and/or the like. In instances where the computation model operates on a coarse-grained (CG) node representation of a molecule, the three dimensional structure of the molecule may be modified by changing the rotation R and/or translation T of one or more of the coarse-grained nodes associated with the molecule, thus altering relative positions of the coarse-grained nodes within the molecule. Alternatively, in cases where the computation model operates on a backbone torsion (BBT) representation of the molecule, the three-dimensional structure of the molecule may be modified by at least updating the frames of one or more amino acid residues in the molecule. For instance, the backbone torsion (BBT) representation of the molecule may be modifying by at least modifying the first set of frames to alter the geometric state of the backbone of the one or more amino acid residues and/or the second set of frames to alter the torsion angles in the sidechain of the one or more amino acid residues. However, a change in the orientation of the entire three-dimensional structure of the molecule, whether through rotating or translating the three-dimensional structure in its entirety, does not constitute a change in the three-dimensional structure of the molecule absent any changes to the relative positions of the atoms (or groups of atoms) contained therein. Accordingly, the computation model may be capable of recognizing when two three-dimensional structures have different orientations in space but are otherwise identical. In doing so, the computation model may be capable of generating a correct three-dimensional structure regardless of the orientation of the initial three-dimensional structure ingested as input.

In some example embodiments, the computation model may include a machine learning model trained to determine the three-dimension structure of a molecule, such as a protein molecule, by at least denoising an initial three-dimensional structure of the molecule. In some cases, the denoising may be performed on a structural representation of the initial three-dimensional structure of the molecule including, for example, a coarse-grained (CG) node representation, a backbone torsion (BBT) representation, and/or the like. Furthermore, in the case of protein design, the denoising may be performed on a sequence representation of the initial sequence of amino acid residues forming the molecule. The machine learning model may denoise the initial three-dimensional structure and/or sequence of the molecule by at least performing a sequence of updates to the structural representation and/or sequence representation of the molecule. For example, in some cases, the machine learning model may be a diffusion model that removes, at each timepoint over a succession of timepoints, a portion of the noise present in the initial three-dimensional structure and/or sequence of the molecule. In some cases, the denoising that is performed at each timepoint may include an incremental update to the structural representation and/or sequence representation of the molecule. Moreover, in some cases, upon removing a portion of noise from the representation of the molecule at a first timepoint, a second quantity of noise may be added back to the representation of the molecule before the diffusion model performs its next update at a second timepoint. The second quantity of noise added by the diffusion model may be determined by a noise schedule, which defines the distribution of noise levels across the successive updates performed by the diffusion model. In some cases, the distribution of noise levels may correspond to the degree-of-freedom (DoF) available for the computation model to modify the initial three-dimensional structure of the molecule. For example, in some cases, more noise may be added to degrees-of-freedom (DoF) where more entropy may be present than to those degrees-of-freedom (DoF) where less entropy is present. The addition of the second quantity of noise may compensate for the errors that may be introduced by the denoising of the representation of the molecule.

FIG. 1A depicts a system diagram illustrating an example of a molecule design system 100, in accordance with some example embodiments. Referring to FIG. 1A, the molecule design system 100 may include a molecule design engine 110, a molecular analysis engine 120, and a client device 130 with a user interface (UI) 145. As shown in FIG. 1A, the molecule design engine 110, the molecular analysis engine 120, and the client device 130 may be communicatively coupled via a network 140. The client device 130 may be a processor-based device including, for example, a workstation, a desktop computer, a laptop computer, a smartphone, a tablet computer, a wearable apparatus, and/or the like. The network 140 may be a wired network and/or a wireless network including, for example, a local area network (LAN), a virtual local area network (VLAN), a wide area network (WAN), a public land mobile network (PLMN), the Internet, and/or the like.

In some example embodiments, the molecule design engine 110 may generate a molecule by at least determining sequence (or the molecular formula) and the corresponding three-dimensional structure of the molecule. As shown in FIG. 1A, the molecule design engine 110 may include a sequence design computation model 113, a representation generator 115, and a molecule design computation model 117. In some instances where the molecule design engine 110 is deployed to perform protein design, the molecule design computation model 117 may determine, based at least on a protein sequence generated by the sequence design computation model 113, the corresponding three-dimensional structure of the output protein sequence. For example, in some cases, the sequence design computation model 113 may generate, based on an input protein sequence (e.g., a seed sequence), the protein sequence. Moreover, in some cases, the molecule design computation model 117 may operate on a structural representation (e.g., a coarse-grained (CG) node representation, a backbone torsion (BBT) representation, and/or the like) of the protein sequence when generating the corresponding three-dimensional structure. Accordingly, in some cases, the output of the sequence design model 115 that is ingested by the representation generator 115 may include a molecular structure file (e.g., a protein structure file) describing the initial three-dimensional structure of the protein sequence. The representation generator 115 may generate a corresponding structural representation of the initial three-dimensional structure of the protein sequence for further manipulation by the molecule design computation model 117.

In some cases, the sequence design computation model 115 may be implemented using one or more machine learning models trained to generate the protein sequence by sampling, based on the input protein sequence (e.g., a seed sequence), a data distribution learned by the one or more machine learning models during training. The one or more machine learning models may be trained based on a variety of known (or observed) protein sequences, including protein sequences known to exhibit certain functions and protein sequences without any known functions. In doing so, the one or more machine learning models may learn a data distribution corresponding to a reduced dimension representation of the sequences of amino acid residues forming the known protein sequences.

Alternatively, the molecule design computation model 117 may determine the sequence as well as the three-dimensional structure of a protein molecule. For example, in some cases, instead of ingesting the structural representation of the initial three-dimensional structure of the protein sequence generated by the sequence design computation model 113, the molecule design computation model 117 may generate the sequence and the three-dimensional structure of the protein molecule by at least modifying a hybrid representation of the protein molecule that includes a sequence representation of an initial sequence of amino acid residues forming the protein molecule and a structural representation of an initial three-dimensional structure of the protein molecule. Moreover, while the molecule design computation model 117 operates on the sequence representation of the protein molecule to modify the sequence of amino acid residues forming the protein molecule, the molecule design computation model 117 may simultaneously operate on the structural representation of the protein molecule to determine the corresponding three-dimensional structure. In doing so, the molecule design computation model 117 may generate a protein molecule whose sequence and three-dimensional structure are more likely to be associated with certain desirable properties.

In some cases, the molecule design computation model 117 may include one or more machine learning models that determines the three-dimensional structure of the protein sequence generated by the sequence design computation model 113 by performing successive modifications to the corresponding structural representation of the protein sequence generated by the representation generator 115. For example, in some cases, the one or more machine learning models implementing the molecule design computation model 115 may be an equivariant neural network, a multi-body higher order equivariant message passing neural network, and/or the like. As described in more detail below, the one or more machine learning models implementing the molecule design computation model 115 may be cognizant of or accounting for the rotational symmetries present in a three dimensional structure. That is, the one or more machine learning models implementing the molecule design computation model 115 may recognize that a three-dimensional structure rotated x degrees about its axis of rotation is the same as the three-dimensional structure rotated y degrees about its axis of rotation. As such, the molecule design computation model 117 may be capable of generating a correct three-dimensional structure regardless of the orientation (e.g., the degrees of rotation) of the initial three-dimensional structure ingested as input.

In some example embodiments, the molecule design computation model 117 may be implemented as a machine learning model that is cognizant of the rotational symmetries present in a three-dimensional structure. For example, the molecule design computation model 117 may be implemented as a geometric deep learning model such as an equivariant neural network and/or the like. The awareness of the rotational symmetries present in a three-dimensional structure may enable the molecule design computation model 117 to recognize when two three-dimensional structures are identical but have different orientations in space. That is, the molecule design computation model 125 may capable of recognizing when two three-dimensional structures are structurally identical (or exhibit an above-threshold structural similarity), which is the case when the constituent coarse-grained nodes of two three-dimensional structures have the same relative positions, even when the overall three-dimensional structures have different orientation in space. As such, the molecule design computation model 117 may generate a correct final three-dimensional structure regardless of the orientation of the initial three-dimensional structure ingested as input.

In some example embodiments, the molecule design computation model 117 may be trained to reduce or minimize one or more loss functions including, for example, a frame aligned point error (FAPE) loss function, a structure violation loss function, and/or the like. Alternatively and/or additionally, the molecule design computation model 117 may be trained to reduce or minimize one or more energy functions quantifying an energy of the three-dimensional structure of a molecule (e.g., a protein molecule, small molecule, ion, nucleic acid, polysaccharide, glycolipid, and/or the like). In instances where the molecule computation model 117 is implemented as an equivariant neural network (ENN), the loss and/or energy of the three-dimensional structure undergoing successive updates by the molecule design computation model 117 may be computed based on the coarse-grained node coordinate transformations and the reverse coarse-grained mapped structures output from each individual block of the equivariant neural network (ENN).

In some example embodiments, the protein molecule generated by the molecule design engine 110 may undergo property analysis by the molecular analysis engine 120. As shown in FIG. 1A, the molecular analysis engine 120 may apply a molecular property computation model 125, which may determine one or more properties of the protein molecule based on the sequence and/or three-dimensional structure of the protein molecule determined by the molecule design engine 110. For example, in some cases, the molecular property computation model 125 may determine, based at least on the sequence and/or three-dimensional structure of the protein molecule, whether the protein molecule exhibits binding affinity towards another molecule (e.g., a viral antigen, a tumor antigen, and/or the like), specificity towards another molecule, lack of nonspecificity, stability (e.g., conformation stability, thermodynamic stability, robustness to different environmental stresses such as protease resistance, and/or the like), non-immunogenicity, human-ness, absence of self-association (or non-aggregation), lack of chemical liabilities (e.g., aspartate isomerization, oxidation, deamidation), developability, and/or the like.

In some example embodiments, the molecule design computation model 125 may be trained to generate the three-dimensional structure of the protein sequence to exhibit one or more desirable properties, such as a particular energy range, a binding affinity and/or binding specificity toward another molecule (e.g., a viral antigen, a tumor antigen, and/or the like), and/or the like. Alternatively and/or additionally, the molecule design computation model 117 may generate the three-dimensional structure of the protein sequence to be suitable and/or configured for one or more downstream tasks such as a predictive analysis of the various properties exhibited by the protein sequence.

As noted, in some cases, the molecule design computation model 117 may generate the sequence and/or three-dimensional structure of the protein molecule such that the protein molecule is more likely to exhibit certain desirable properties. Alternatively and/or additionally, the molecule design computation model 117 may generate the sequence and/or three-dimensional structure of the protein molecule to be more suitable or configured for one or more downstream tasks, such as the property analysis performed by the molecular analysis engine 120.

In the example shown in FIG. 1A, the properties of the protein sequence may be determined by the molecular analysis engine 120 at least applying the molecular property analysis computation model 125, for example. For example, in some cases, the molecular property computation model 125 may determine, based at least on the second protein sequence and/or the three-dimensional structure of the second protein sequence determined by the molecule design computation model 117, one or more properties of the protein sequence (e.g., expression, affinity, and/or the like) 120. Furthermore, the three-dimensional structure of the second protein sequence determined by the molecule design computation model 117 and/or the properties of the second protein sequence determined by the molecular property computation model 125 may be used by the molecule design engine 110 (e.g., the sequence design computation model 113) when generating subsequent additional protein sequences. For example, in cases where the second protein sequence is determined to exhibits a desirable three-dimensional structure and/or a desirable property, the molecular design engine 110 may apply the sequence design computation model 113 to generate, based on at least the second protein sequence (e.g., as a seed sequence), a third one or more additional protein sequences. Alternatively, in cases where the second protein sequence fails to exhibit a desirable three-dimensional structure and/or a desirable property, the molecule design engine 110 may apply the molecule design computation model 113 to generate the third one or more additional protein sequences based on a fourth different protein sequence (e.g., as the seed sequence) instead.

Figure 1B:
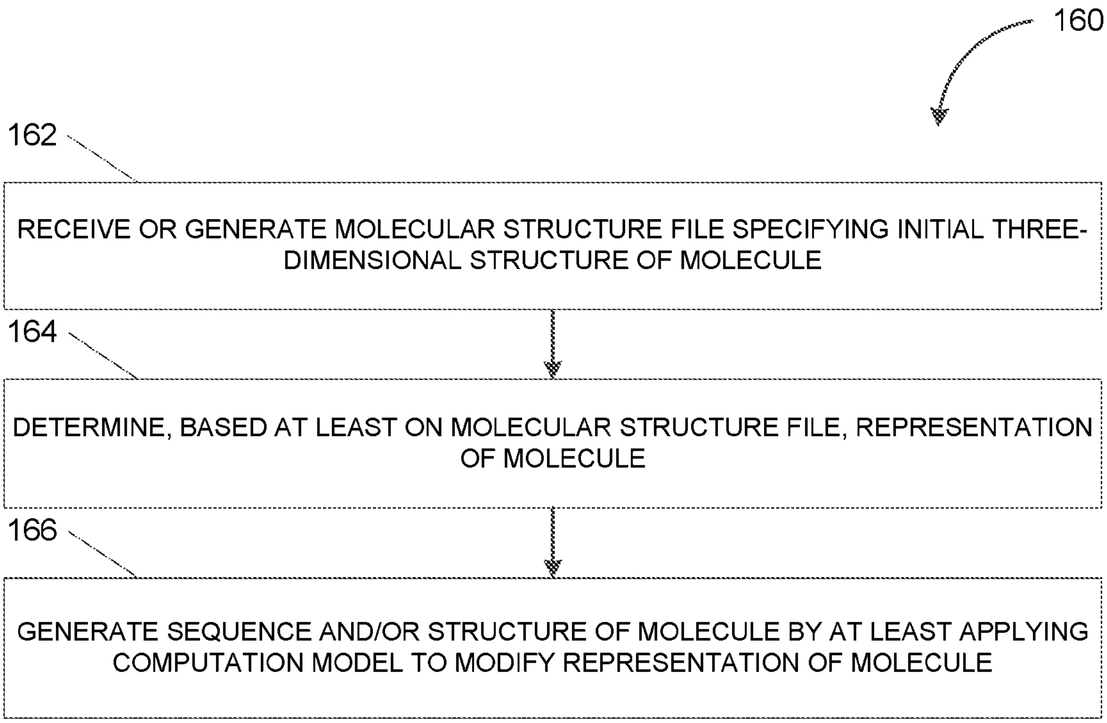
FIG. 1B depicts a flowchart illustrating an example of a process 160 for protein structure and property prediction, in accordance with some example embodiments.

FIG. 1B depicts a flowchart illustrating an example of a process 160 for protein structure and property prediction, in accordance with some example embodiments. Referring to FIGS. 1A-1B, the process 160 may be performed by the design system 100, for example, by the molecule design engine 110. In some cases, the process 160 may implement a generative design process in which the molecule design computation model 117 operates on a structural representation, such as a coarse-grained (CG) node representation or a backbone torsion (BBT) representation, of a protein molecule having a known protein sequence in order to determine the three-dimensional structure of the protein molecule. Alternatively, in some cases, the process 1600 may implement a generative design process in which the molecule design computation model 117 operates on a hybrid representation of a molecule, such as a protein molecule, which includes a sequence representation (e.g., logit representation, one-hot-encoded representation, and/or the like) and a structural representation of the protein molecule (e.g., a coarse-grained (CG) node representation, a backbone torsion (BBT) representation, and/or the like), to determine the sequence as well as the three-dimensional structure of the protein molecule.

At 162, the molecule design engine 110 may receive or generate a molecular structure file specifying an initial three-dimensional structure of a molecule. For example, in some cases, the molecule design engine 120 may apply the sequence design computation model 113 to generate a protein sequence (or sequence of amino acid residues), in which case the output of the sequence design computation model 113 may be a molecular structure file. Alternatively, in some cases, the molecular design engine 110 may receive the molecular structure file from another source such as another sequence design platform. In some cases, the molecular structure file may specify an initial three-dimensional structure of a molecule, which may be a protein molecule or a non-protein molecule (e.g., a small molecule, a nucleic acid, a polysaccharide, a glycolipid, and/or the like). The molecular structure file may specify the initial three-dimensional structure of the molecule by at least enumerating the constituent atoms. In cases where the molecule is a protein molecule, the molecular structure file may specify the initial three-dimensional structure of the protein molecule by at least enumerating the individual atoms (e.g., heavy atoms) forming each of the amino acid residues in the protein molecule.

In some example embodiments, the initial three-dimensional structure of the molecule may include varying degrees of entropy, or randomness in the spatial arrangement of the constituent atoms, which are subsequently removed by the molecule design computation model 117 in order to determine the actual three-dimensional structure of the molecule. For example, in some cases, the initial three-dimensional structure of the molecule may include at least some noise (e.g., Gaussian noise and/or the like), meaning that the positions of the constituent atoms in the initial three-dimensional structure of the molecule may be inconsistent with the positions of those atoms in the actual three-dimensional structure of the molecule. In some cases, the molecule design computation model 117 may perform successive modifications to correct the positions of the atoms in the initial-three dimensional structure of the molecule. Alternatively and/or additionally, in instances where the molecule is a protein molecule, the initial three-dimensional structure of the molecule may include one or more groupings of amino acid residues that correspond to the polymer chains present in the molecule. Such groupings may impose at least some limitations on the modifications made by the molecule design computation model 117. For instance, in some cases, the molecule design computation model 117 may avoid modifications that move two or more amino acid residues in a single polymer chain more than a threshold distance apart.

At 164, the molecule design engine 110 may determine, based at least on the molecular structure file, a representation of the molecule. In some example embodiments, the representation generator 115 of the molecule design engine 120 may determine, based at least on the molecular structure file, a representation of the molecule. In some cases, the representation of the molecule may include a structural representation of the molecule. As described in more details below, the structural representation of the molecule may be a coarse-grained (CG) node representation including a collection of coarse-grained (CG) nodes, each of which corresponding to a structural body formed by one or more constituent atoms in the molecule. Alternatively, where the molecule is a protein molecule having a sequence of amino acid residues, the representation of the molecule may be a backbone torsion (BBT) representation including, for each amino acid residue in the protein molecule, a corresponding plurality of frames specifying the geometric state of the backbone and the sidechain of the amino acid residue. In cases where the molecule is a protein molecule, the representation of the molecule may further include, in addition to the structural representation of the molecule, a sequence representation of the molecule. In some cases, the sequence representation of the protein molecule may be a logit representation in which each position in the sequence forming the protein molecule may be a logit vector that represents the identity of the amino acid residue occupying the position by at least enumerating a probability distribution (e.g., categorical distribution) across the set of possible amino acid residues. Alternatively, the sequence representation of the protein molecule may be a one-hot-encoded representation in which each position in the sequence forming the protein molecule may be a one-hot-encoded vector where the value “1” occupies the position in the one-hot-encoded vector corresponding to the identity of the amino acid residue occupying the position in the sequence and the value “0” occupies the other positions in the one-hot-encoded vector.

As noted, in some example embodiments, the identity of the amino acid residue occupying each position in the protein sequence may constitute one of the degrees of freedom (DoF) associated with the amino acid residue. This particular degree-of-freedom may limit changes to the identity of the amino acid residue occupying each position to, for example, one of the 20 canonical amino acid residues. Accordingly, in some cases, the degree-of-freedom (DoF) associated with the amino acid residue identity may be represented as categorical probabilities. Where there are an N quantity of amino acid residues in the protein sequence, the logit representation of the protein sequence may be a sequence of probability vectors ($p_1, \ldots, P_N$), with each probability vector $p_i$ enumerating the probability distribution of the identity of the amino acid residue occupying the i-th position across the set of possible amino acid residues (e.g., the 20 canonical amino acid residues). For example, the probability vector $p_1$ for the first position in the protein sequence may include a first probability of the first position being occupied by alanine (Ala), a second probability of the first position being occupied y arginine (Arg), a third probability of the first position being occupied by asparagine (Asn), and/or the like.

In some cases, each probability vector $p_i \in \text{Simplex}(D)$, meaning that the constituent probabilities across the set of possible amino acid residues sum to 1. For example, the probability that the amino acid residue occupying a particular position in the protein sequence is each one of the 20 canonical amino acid residues adds up to 1. The probability simplex Simplex(D) may be a mathematical space in which each point represents a probability distribution between a finite number of mutually exclusive events, or categories, which in this case correspond to the set of possible amino acid residues (e.g., the 20 canonical amino acid residues). It should be appreciated that the probability simplex Simplex (D) is a (D−1) dimensional object. That is, the points forming the probability simplex Simplex(D) occupy a (D−1) dimensional space, with D corresponding to the quantity of possible amino acid residues (e.g., 20 canonical amino acid residues). The requirement that the probabilities across the D quantity of possible amino acid residues (e.g., 20 canonical amino acid residues) sum up to 1 reduces the dimensions of the probability simplex Simplex(D) by 1. As described in more detail below, the molecule design computation model 125 applied to the sequence representation of the protein sequence may be a diffusion model that adds noise during the forward diffusion process and removes noise during the corresponding reverse diffusion process. Defining the forward diffusion process on the probability simplex Simplex (D) is nontrivial at least because adding noise (e.g., Gaussian noise) in a naïve manner to each probability vector $p_i$ may result in the sum of the constituent probabilities across the D quantity of possible amino acid residues (e.g., 20 canonical amino acid residues) no longer summing up to 1. In other words, noise may be added in a principled manner during forward diffusion in order to maintain the (D−1) dimensionality of the probability simplex Simplex(D). For instance, to maintain a one-to-one mapping from the probability simplex Simplex(D) to the logit space $p_i \in \text{Simplex}(D) \rightarrow l_i \in R^D$, where the addition of noise (e.g., Gaussian noise) to the logits $l_i$ keeps the logits $l_i$ in the same space $R^D$, may require the logit space to be constrained from having D dimensions to D−1 dimensions. This constraint is achieved by projecting the logits $l_i$ onto the zero-identity component subspace by subtracting its mean $l_i \rightarrow l_i - \bar{l}_i$. A unique mapping from the logit subspace to probabilities may be established, without any degeneracy, by applying the softmax function.

In some cases, instead of the aforementioned logit representation, the identities of each amino acid residue in the protein sequence may be rendered in a one-hot-encoding representation. Accordingly, each position in the protein sequence may be associated with a one-hot-encoded vector in which the value "1" occupies the position in the one-hot-encoded vector corresponding to the amino acid residue occupying the position in the protein sequence while the value "0" occupies every remaining position in the one-hot-encoded vector. For example, if a position in the protein sequence is occupied by Alanine (Ala/A), the one-hot-encoded vector for that position may include the value "1" in the position corresponding to Alanine (Ala/A) and the value "0" in the positions corresponding to the other amino acid residues.

It should be appreciated that the logit representation of the amino acid residues forming the protein sequence may be used instead of other representations, such as one-hot-encoding, in order to enhance the learning of the molecule design computation model 117. One-hot-encoding, for example, does not provide a probabilistic representation of the identities of each amino acid residue in the protein sequence. Instead, the identity of the amino acid residue occupying a position in the protein sequence is denoted by the value "1" in the corresponding position in a one-hot-encoded vector while the remaining positions in the one-hot-encoded vectors are occupied by the value "0". The addition of noise as part of the forward diffusion process does not make binary-valued changes to the one-hot-encoded vector. The resulting values may no longer be consistent with the one-hot-encoding scheme, with a single value of "1" in the one-hot-encoded vector identifying the identity of the amino acid residue in the protein sequence. Instead, a range of different values can result but those values will still correspond to the same physical state. For example, the one-hot-encoded vector [1.0,0.0] can signify the same physical state as the one-hot-encoded vector [0.5, 0.0], meaning that the molecule design computation model 117 may be constructed to learn to generate the same output for some one-hot-encoded vectors with different values. As such, the performance of the molecule design computation model 117 may deteriorate when operating on one-hot-encoded representations of the identities of the amino acid residues in the protein sequence.

At 166, the molecule design engine 110 may determine the sequence and/or three-dimensional structure of the molecule by at least applying the molecule design computation model 125 to modify the representation of the molecule. In some example embodiments, the molecule design engine 110 may determine the three-dimensional structure and, in some cases, also the sequence of the molecule by at least applying the molecule computation model 125 to modify the representation of the molecule. In some cases, the molecule design computation model 125 may perform successive updates to the representation of the molecule in order to determine the sequence and/or the three-dimensional structure of the molecule. For example, where the molecule is represented as a collection of coarse-grained (CG) nodes, the molecule design computation model 125 may perform successive updates, each of which modifying one or more coarse-grained (CG) nodes forming the structural representation of the molecule. Alternatively, where the molecule design computation model 117 operates on the backbone torsion (BBT) representation of the molecule, each successive update may modify one or more frames forming the structural representation of the molecule.

In some cases, the molecule design computation model 117 may simultaneously determine the sequence and the three-dimensional structure of the molecule, for example, by performing successive updates to the sequence representation and the structural representation of the molecule. As described in more details below, the sequence and/or the three-dimensional structure of the molecule determined by the molecule design computation model 117 may be used for one or more downstream tasks including, for example, conformer generation, molecular docking, property prediction, and/or the like.

In cases where the structural representation of the three-dimensional structure of the protein sequence generated by the sequence design computation model 113 is a coarse-grained (CG) node representation, the structural representation of the protein sequence may include a collection of coarse-grained nodes, with each amino acid residue included in the protein sequence being associated with a corresponding set of coarse-grained (CG) nodes. For instance, each amino acid residue included in the protein sequence may include one or more structural bodies with each structural body being a group of two or more atoms. In the case of a rigid structural body, the locations of the two or more atoms may be fixed with respect to the coordinates of the structural body. Contrastingly, as a flexible or variable structural body, the locations of the two or more atoms may exhibit at least some degree of flexibility with respect to the coordinates of the structural body.

As such, each amino acid residue in the protein sequence may be associated with at least one coarse-grained (CG) node corresponding to a structural body (e.g., rigid body, flexible or variable body, and/or the like) included in the amino acid residue. In instances where a single atom is a part of multiple structural bodies included in the amino acid residue, that atom may be included in multiple corresponding coarse-grained nodes. In some cases, the coarse-grained (CG) node representation of the protein sequence may include or exclude certain elements such as hydrogen (H) and/or the like. For example, in some cases, the coarse-grained (CG) node representation of the protein sequence may include the hydrogen atoms found in the amino acid residues forming the protein sequence. However, in other instances, the coarse-grained (CG) node representation of the protein sequence may exclude the hydrogen atoms found in the amino acid residues forming the protein sequence.

To further illustrate, given the protein sequence $a=a_1a_2 \ldots a_n$ of length N where $a_i$ is an amino acid residue (e.g., one of 20 canonical amino acids), the three-dimensional structure formed by the protein sequence may be specified by the three-dimensional coordinates of its constituent atoms grouped by amino acids, $$X = \{X_i^{a_i} \mid X_i^{a_i} \in R^{n_{a_i} \times 3}\}_{i=1}^{N}$$

wherein $n_{a_i}$ denotes the quantity of atoms in the amino acid residue $a_i$. Accordingly, in the coarse-grained node representation of the protein sequence, each amino acid $a_i$ may be represented by a set of coarse-grained nodes $$\{c_j^{a_i}\}_{j=1}^{n_{CG}^{a_i}}$$

in which each coarse-grained node $$c_j^{a_i}$$

is representative of a subset $$\sigma_j^{a_i}$$

of the atoms (e.g., heavy atoms) forming the amino acid $a_i$.

In some example embodiments, the representation generator 115 may generate the coarse-grained (CG) node representation of the protein sequence by at least grouping the atoms enumerated in the molecular structure file into one or more coarse-grained (CG) nodes. The coarse-grained node representation of the protein sequence may be generated to satisfy certain properties. For example, the representation generator 115 may generate each coarse-grained node included in the coarse-grained node representation of the protein sequence such that the union of the every coarse-grained (CG) node representative of an amino acid residue in the protein sequence includes all of that amino acid residue's constituent atoms. In this context, the union of two or more coarse-grained (CG) nodes includes the atoms that are present in every coarse-grained nodes. For instance, the union of a first coarse-grained node and a second coarse-grained node includes a first plurality of atoms that are present in the first coarse-grained node but not the second coarse-grained node, a second plurality of atoms that are present in the second coarse-grained node, and a third plurality of atoms that are present in both the first coarse-grained node and the second coarse-grained node. As such, every atom in an amino acid residue in the protein sequence may be included in at least one coarse-grained (CG) node associated with that amino acid residue. Moreover, when generating the coarse-grained (CG) nodes included in the coarse-grained node representation of the protein sequence, the atoms enumerated in the molecular structure file may be grouped such that each member atom of a coarse-grained node shares at least one covalent bond with another member of the same coarse-grained node. In some cases, the representation generator 115 may generate the coarse-grained node representation of the protein sequence such that each coarse-grained node includes a threshold quantity of atoms (e.g., a minimum quantity and/or a maximum quantity of atoms) and its constituent atoms collectively form at least one structural body as described above.

In some cases, upon grouping the atoms enumerated in the molecular structure file into one or more coarse-grained (CG) nodes, the representation generator 115 may further generate the coarse-grained (CG) node representation of the protein sequence by mapping the coordinates of the atoms (e.g., heavy atoms) forming each coarse-grained node to a corresponding Euclidean transformation (e.g., translation, rotation, and/or the like). Since each coarse-grained node associated with the protein sequence is generated to include a threshold quantity of atoms (e.g., heavy atoms) forming at least one structural body, a forward mapping F of the three-dimensional coordinates $$X_i^{a_i}$$

of an amino acid residue $a_i$ included in the protein sequence into its corresponding coarse-grained node representation may include or be defined as $$F\colon X_i^{a_i} \mapsto \{(T_j^{a_i}, c_j^{a_i})\}_{j=1}^{n_{CG}^{a_i}}$$

wherein each tuple in the set includes a coarse-grained node identity $$c_j^{a_i}$$

and a Euclidean transformation $$T_j^{a_i} = \left(\vec{t}_j^{a_i}, R_j^{a_i}\right) \in SE(3)$$

mapping the predefined template coordinates of the subset of atoms $$\sigma_j^{a_i}$$

in the amino acid $a_i$ to the corresponding input atom coordinates. As used herein, the template coordinates of each coarse-grained (CG) node may correspond to the initial translations and/or rotations applied to the coarse-grained of node. That is, the template coordinates of a coarse-grained (CG) node may determine the initial positions of the constituent atoms in the coarse-grained (CG) node representation of the initial three-dimensional structure of protein sequence. Meanwhile, a reverse mapping G of an amino acid $a_i$ from its coarse-grained (CG) node representation to the corresponding three-dimensional coordinates $$X_i^{a_i}$$

may include or be defined as an average of the three-dimensional coordinates of the atom as specified by any of the coarse-grained nodes containing the atom.

To further illustrate, FIG. 2A depicts an example of a coarse-grained node representation 200 of the protein sequence that excludes the hydrogen (H) atoms in each constituent amino acid residue while FIG. 2B depicts another example of a coarse-grained node representation 250 of the protein sequence including hydrogen (H) atoms. For instance, in the example of the coarse-grained node representation 200 shown in FIG. 2A, the coarse-grained node representation of the amino acid residue tryptophan (Trp) includes the first coarse-grained node CG0 (“C”, “CA”, “CB”, “N”), the second coarse-grained node CG1 (“C”, “CA”, “O”), and the third coarse-grained node CG2 (“CG”, “CD1”, “CD2”, “CE2”, “CE3”, “CZ2”, “CZ3”, “CH2”, “NE1”). Meanwhile, the coarse-grained node representation of the amino acid residue valine (Val) may include the first coarse-grained node CG0 (“C”, “CA”, “CB”, “N”), the second coarse-grained node CG1 (“C”, “CA”, “O”), and the third coarse-grained node CG2 (“CB”, “CG1”, “CG2”). A coarse-grained node may specify the three-dimensional positions of its constituent atoms by the rotation R and/or translation T of the coarse-grained node as a whole. For example, the positions of the carbon I atom, alpha carbon ($C_\alpha$) atom, beta carbon ($C_\beta$) atom, and nitrogen (N) in the first coarse-grained node CG0 associated with the amino acid residue tryptophan (Trp) may be specified by the rotation R and/or translation T of the first coarse-grained node CG0.

As noted, in some example embodiments, the representation generator 115 may determine the Euclidean transformations, such as the rotation R and/or translation T, of each coarse-grained node representative of the initial three-dimensional structure of the protein sequence. For example, the representation generator 115 may determine the rotation R and/or translation T required to transform each coarse-grained node from its current position to a template position (e.g., template coordinates) of the coarse-grained node in order to determine the initial three-dimensional structure of the protein sequence. In some cases, the representation generator 115 may determine the rotation R and/or translation T by at least computing a rotation matrix with a minimal root mean squared deviation (RMSD) between the template position of the coarse-grained node and the current position of the coarse-grained node. For instance, in some cases, the representation generator 115 may apply a Kabsch algorithm in order to compute a rotation matrix and a translation with a minimal root mean squared deviation (RMSD) between the template position of the coarse-grained node and the current position of the coarse-grained node.

To further illustrate the computation of template coordinates of each coarse grained in the protein sequence, consider a protein structure dataset D associated with the protein sequence. The coordinate transformations (e.g., Euclidean transformations) $T_q$ of each coarse-grained node q in the protein structure dataset D may be computed by applying, for example, a Gram-Schmidt process shown in Table 2 below, to the three-dimensional coordinates of the first three atoms of the coarse-grained node q's atom group.

TABLE 2

| | |
|---|---|
| def rigidFrom3Points($\vec{x}_1, \vec{x}_2, \vec{x}_3$): | $\vec{x}_1, \vec{x}_2, \vec{x}_3 \in \mathbb{R}^3$ |
| $\vec{v}_1 = \vec{x}_3 - \vec{x}_2$ | |
| $\vec{v}_2 = \vec{x}_1 - \vec{x}_2$ | |
| $\vec{e}_1 = \vec{v}_1 / \lVert\vec{v}_1\rVert$ | |
| $\vec{u}_2 = \vec{v}_2 - \vec{e}_1 \left(\vec{e}_1^T \vec{v}_2\right)$ | |
| $\vec{e}_2 = \vec{u}_2 / \lVert\vec{u}_2\rVert$ | |
| $\vec{e}_3 = \vec{e}_1 \times \vec{e}_2$ | |
| R = concat($\vec{e}_1, \vec{e}_2, \vec{e}_3$) | $R \in \mathbb{R}^{3\times3}$ |
| $\vec{t} = \vec{x}_2$ | |
| return (R, $\vec{t}$) | |

An inverse coordinate transformation (e.g., Euclidean transformation)

$$T_q^{-1}$$

then be applied to the three-dimensional coordinates of all atoms in the coarse-grained node q to transform these three-dimensional coordinates into the corresponding local frame. In this context, the term “frame” may refer to the transformations (e.g., Euclidean transformations) that defines coordinates (e.g., three-dimensional coordinates) of at least a portion of the atoms in the protein molecule. Whereas the aforementioned local frame may define the position of the atoms included in a single coarse-grained node, such as the coarse-grained node q, a global frame may define the position of the protein molecule as a whole (e.g., by specifying the rotations and translations applied to a center of mass of the molecule). In some cases, to determine the template coordinates, the three-dimensional coordinates observed in the local frames across all instances in the protein structure dataset D grouped by the coarse-grained node types set forth in Table 2 below may be averaged. That is, where the protein structure dataset D include multiple coarse-grained nodes representative of the same amino acid residue, the computation of template coordinates may include determining an average of the three-dimensional coordinates observed across the local frames of these coarse-grained nodes.

TABLE 2

| AA | CG1 | CG2 | CG3 | CG4 |
|---|---|---|---|---|
| ALA | C, $C_\alpha$, $C_\beta$, N | C, $C_\alpha$, O | — | — |
| ARG | C, $C_\alpha$, $C_\beta$, N | C, $C_\alpha$, O | $C_\beta$, $C_\gamma$, $C_\delta$ | $N_\epsilon$, $N_{\eta1}$, $N_{\eta2}$, $C_\zeta$ |
| ASN | C, $C_\alpha$, $C_\beta$, N | C, $C_\alpha$, O | $C_\gamma$, $N_{\delta2}$, $O_{\delta1}$ | — |
| ASP | C, $C_\alpha$, $C_\beta$, N | C, $C_\alpha$, O | $C_\gamma$, $O_{\delta1}$, $O_{\delta2}$ | — |
| CYS | C, $C_\alpha$, $C_\beta$, N | C, $C_\alpha$, O | $C_\alpha$, $C_\beta$, $S_\gamma$ | — |
| GLN | C, $C_\alpha$, $C_\beta$, N | C, $C_\alpha$, O | $C_\gamma$, $C_\delta$, $O_\epsilon$, $N_{\epsilon2}$ | — |
| GLU | C, $C_\alpha$, $C_\beta$, N | C, $C_\alpha$, O | $C_\gamma$, $C_\delta$, $O_{\epsilon1}$, $O_{\epsilon2}$ | — |
| GLY | C, $C_\alpha$, N | C, $C_\alpha$, O | — | — |
| HIS | C, $C_\alpha$, $C_\beta$, N | C, $C_\alpha$, O | $C_\gamma$, $C_{\delta2}$, $C_{\epsilon1}$, $N_{\delta1}$, $N_{\epsilon2}$ | — |
| ILE | C, $C_\alpha$, $C_\beta$, N | C, $C_\alpha$, O | $C_\beta$, $C_{\gamma1}$, $C_{\gamma2}$ | $C_\beta$, $C_{\gamma1}$, $C_{\delta1}$ |
| LEU | C, $C_\alpha$, $C_\beta$, N | C, $C_\alpha$, O | $C_\gamma$, $C_{\delta1}$, $C_{\delta2}$ | — |
| LYS | C, $C_\alpha$, $C_\beta$, N | C, $C_\alpha$, O | $C_\beta$, $C_\gamma$, $C_\delta$ | $C_\delta$, $C_\epsilon$, $N_\zeta$ |
| MET | C, $C_\alpha$, $C_\beta$, N | C, $C_\alpha$, O | $C_\gamma$, $C_\epsilon$, $S_\delta$ | — |
| PHE | C, $C_\alpha$, $C_\beta$, N | C, $C_\alpha$, O | $C_\gamma$, $C_{\delta1}$, $C_{\delta2}$, $C_{\epsilon1}$, $C_{\epsilon2}$, $C_\zeta$ | — |
| PRO | C, $C_\alpha$, $C_\beta$, N | C, $C_\alpha$, O | $C_\beta$, $C_\gamma$, $C_\delta$ | — |
| SER | C, $C_\alpha$, $C_\beta$, N | C, $C_\alpha$, O | $C_\alpha$, $C_\beta$, $O_\gamma$ | — |
| THR | C, $C_\alpha$, $C_\beta$, N | C, $C_\alpha$, O | $C_\beta$, $C_{\gamma2}$, $C_{\gamma1}$ | — |
| TRP | C, $C_\alpha$, $C_\beta$, N | C, $C_\alpha$, O | $C_\gamma$, $C_{\delta1}$, $C_{\delta2}$, $C_{\epsilon2}$, $C_{\epsilon3}$, $C_{\zeta2}$, $C_{\zeta3}$, $C_{\eta2}$, $N_{\epsilon1}$ | — |
| TYR | C, $C_\alpha$, $C_\beta$, N | C, $C_\alpha$, O | $C_\gamma$, $C_{\delta1}$, $C_{\delta2}$, $C_{\epsilon1}$, $C_{\epsilon2}$, $C_\zeta$, $O_\eta$ | — |
| VAL | C, $C_\alpha$, $C_\beta$, N | C, $C_\alpha$, O | $C_\beta$, $C_{\gamma1}$, $C_{\gamma2}$ | — |

To compute the ground truth coordinate transformations (e.g., Euclidean transformations) for a given coarse-grained node to be used in the loss function of the molecule design computation model 117 (e.g., a frame aligned point error (FAPE) loss function), Kabsch algorithm may be applied to determine a transformation from the template coordinates to the observed coordinates that reduces or minimizes the root mean square error (RMSE) of each coarse-grained node's constituent atoms. For example, for the j-th coarse-grained node $$c_j^{a_j}$$

containing M atoms of the i-th amino acid residue $a_i$, Kabsch algorithm may be applied to the template coordinates $$W = \left[\vec{w}_1^{c_j^{a_i}}, \ldots, \vec{w}_M^{c_j^{a_i}}\right] \in R^{3\times M}$$

and the corresponding input coordinates $$X = \left[\vec{x}_1^{c_j^{a_i}}, \ldots, \vec{x}_M^{c_j^{a_i}}\right] \in R^{3\times M}.$$

The Kabsch algorithm factorizes the covariance matrix $$H = W_c X_c^T$$

into eigenvectors and values using singular vector decomposing as shown in Equation (1) below.

$$H = USV^T \tag{1}$$

wherein $W_c$ denotes the mean centered template coordinates and $X_c$ denotes the mean centered input coordinates.

The resulting rotation and translations may be expressed Equations (2) below.

$$R_j^{a_i} = VU^T,\ \vec{t}_j^{a_i} = \vec{x}_\mu^{c_j^{a_i}} - R_j^{a_i} w_\mu^{c_j^{a_i}}, \tag{2}$$

wherein $$w_\mu^{c_j^{a_i}} \in R^3 \text{ and } \vec{x}_\mu^{c_j^{a_i}} \in R^{3\times M}$$

are the mean coordinates of W and X respectively.

FIG. 3A depicts a visualization of the positions of the atoms in the first coarse-grained node CG0, the second coarse-grained node CG1, and the third coarse-grained node CG2 of the amino acid residue tryptophan (Trp) in the local frame of the template coordinates after the individual atoms are fitted to the template coordinates to show their relative position to one another. FIG. 3B depicts a visualization of the positions of the atoms in each coarse-grained node of the amino acid valine (Val) in the local frame of the template coordinates after the individual atoms are fitted to the a local reference frame template coordinates to show their relative position to one another. The bars shown in FIG. 3A-3B provide a visual indication of the error associated with the position of each atom. As shown in FIG. 3A-3B, the error is small.

In some example embodiments, the transformations (e.g., the Euclidean transformations) applied to each coarse-grained (CG) node may be further represented numerically as a set of geometric tensors having a configurable maximum degree L. In some cases, the rotation and/or translation of each geometric tensor associated with a coarse-grained (CG) node may be determined by applying one or more elements from the three-dimensional rotation group. For example, the numerical representation of the first coarse-grained node CG0 of the amino acid residue tryptophan (Trp) may include one or more geometric tensor steered by one or more elements from the three-dimensional rotation group to describe the current translation T and/or rotation R of the first coarse-grained node CG0 in three-dimensional space.

To further illustrate, each coarse-grained node associated with the protein sequence may be assigned a set of geometric tensor features of degree $l=0, \ldots, l_{max}$ with $n_c$ channels per degree. Given there are 2l+1 features associated with an l-degree tensor, there are then $n_c \times (l_{max}+1)^2$ geometric tensor features per coarse-grained node. The initial embedding for the coarse-grained nodes $E{:}C\times S0(3) \rightarrow R^{n_c\times(l_{max}+1)^2}$, in which C denotes the predetermined set of coarse-grained node types, may include or be defined as $$E{:}\ \left(c_j^{a_i}, R_j^{a_i}\right) \mapsto e_j^{a_i} i = D\left(R_j^{a_i}\right) \cdot LookUp\left(c_j^{a_i}\right)$$

wherein LookUp:C→$R^{n_c\times(l_{max}+1)^2}$ denotes an embedding function and $$D(R_j^{a_i})$$

denotes the direct sum of the Wigner D-matrices $D_l$ corresponding to the geometric tensor features of various degrees l expressed as follows:

$$D(R_j^{a_i}) = \bigoplus_{l=0}^{l_{max}}\left[\bigoplus_{c=1}^{n_c} D_l(R_j^{a_i})\right]$$

Representing each amino acid residue in the initial three-dimensional structure of the protein sequence as a collection of coarse-grained (CG) nodes, in particular as geometric tensor embeddings, may reduce the computational complexity associated with subsequent manipulations of the initial three-dimensional structure to determine the three-dimensional structure of the protein sequence. The coarse-grained node representation of the protein sequence may omit overly granular details such as chemical variations and variations in bond angles and bond lengths. As such, the molecule design computation model 117 may be able to operate with greater computational efficiency on coarse-grained nodes as discrete semantic units than on individual atoms. Moreover, the molecule design computation model 117 may be capable of determining the three-dimensional structure of the protein sequence without additional information such as the co-occurrence frequency of certain amino acid residues at various positions.

In some example embodiments, the molecule design engine 110 may apply the molecule design computation model 117 to determine, based at least on the geometric tensor embeddings of the coarse-grained (CG) node representation of the initial three-dimensional structure of the protein sequence, the three-dimensional structure of the protein sequence. In some cases, the molecule design computation model 117 may be implemented as a machine learning model (e.g., an equivariant neural network and/or the like) having a sequence of blocks, each of which being a sub-unit of the machine learning model that includes one or more layers of the machine learning model. Each block of the machine learning model may be trained to determine an update to the transformations (e.g., Euclidean transformations such as rotation R and/or translation T) that define the positions of one or more of the coarse-grained nodes included in the initial three-dimensional structure of the protein sequence. Accordingly, the molecule design computation model 117 may perform successive updates on the transformations (e.g., Euclidean transformations such as rotation R and/or translation T) that are applied to define the positions of one or more of the coarse-grained nodes within the initial three-dimensional structure in order to derive the actual three-dimensional structure of the protein sequence.

As noted, the coarse-grained (CG) node representation of the protein sequence may be instantiated with coordinate transformations are defined by one or more elements sampled from the three-dimensional rotation group. For example, in some cases, the coarse-grained node representation of the protein sequence may be instantiated with Euclidean transformations whose translations and rotations are sampled from a normal distribution with zero mean and unit variance and a uniform distribution over the three-dimensional rotation group SO(3). The final three-dimensional structure determined by the molecule design engine 110 may be generated via iterative refinement performed by the molecule design computation model 117 implemented, for example, as an equivariant neural network having an $N_{blocks}$ quantity of blocks, each of which having a same architecture of an $N_{sub}$ quantity of sub-blocks. Accordingly, each block of the equivariant neural network may ingest, as input, either the initial coarse-grained node representation of the protein sequence or an updated coarse-grained node representation of the protein sequence output by a previous block. Moreover, each block may output two l=1 geometric tensors for each coarse-grained node associated with the protein sequence, with the first geometric tensor used as the vector part of a non-unit quaternion to compute an update R' to the previous rotation $R_{in}$ of the coarse-grained node and the second geometric tensor used as an update $\vec{t}'$ to the previous translation $\vec{t}$ of the coarse-grained node.

As such, the initial coordinate transformation ($R_{in}$, $\vec{t}_{in}$) applied to the initial template coordinates of the protein sequence may undergo successive updates by the equivariant neural network (ENN) in accordance with the following:

$$R_{new} = R' R_{in} \vec{t}_{new} = \vec{t}' + \vec{t}_{in}$$

Each block of the equivariant neural network may either transform or simply copy the input embedding of each coarse-grained node. Nevertheless, in either instance, the input embeddings of the coarse-grained nodes may be multiplied by the direct sum of the Wigner D-matrices corresponding to the update rotation R'.

For example, in some cases, each block of the equivariant neural network may include an $N_{sub}$ quantity of sub-blocks sharing the same architecture (e.g., a transformer architecture). Given the input set of coarse-grained nodes and their corresponding coordinate transformations (e.g., into template coordinates), the block initially computes pairwise distances $r_{ij}$ and normalized distance vectors $\hat{r}_{ij}$, where i and j index the coarse-grained nodes. The pairwise distances $r_{ij}$ may be projected onto $d_{bessel}$ radial Bessel basis with learnable weights and a cutoff distance of $r_c$, which are used in radial functions that parameterize tensor products in the Equivariant Graph Attention module. Instead of a polynomial envelope function, a soft unit step may be applied with $$\frac{10(1-r_{ij})}{r_c}$$

as input. The normalized distance vectors $\hat{i}_{i,j}$ may be used to compute spherical harmonics SH($\hat{r}_{ij}$) input to tensor products. When training the equivariant neural network, it may be the case that gradients do not propagate through the pairwise distances $r_{ij}$ and normalized distance vectors $\hat{r}_{ij}$.

Upon the application of the initial linear layers to the embeddings of the input coarse-grained nodes, instead of pairwise summation, channel-wise fully connected tensor products may be applied to the embeddings of every coarse-grained node pair ij before another linear layer is applied to produce output tensors $x_{ij}$ with the same number of channels as the input. Thereafter, a depth-wise tensor product (DTP) may be applied to the output tensors $x_{ij}$ and the spherical harmonics SH($\hat{r}_{ij}$) with a radial function that ingests, as input, the aforementioned Bessel basis as well as a scalar edge embedding vector corresponding to the amino acid sequence distance for the coarse-grained node pair ij, clamped at a certain distance (e.g., 32). In some cases, the edge embedding may be implemented as a lookup table with learnable weights and with the same dimension as the number of channels in the input tensors. The output of the depth-wise tensor product layer may be uniformly shuffled and grouped by an $N_{head}$ quantity of attention heads. A linear layer may be applied to produce tensors of various degrees with appropriate channel numbers for the remainder of the module. The output of each sub-block except for the last sub-block may be updated geometric tensors representative of the transformations applied to the corresponding coarse-grained nodes in the three-dimensional structure of the molecule. The last sub-block may output two l=1 tensors for each coarse-grained node. Edge embeddings may be shared across the sub-blocks of a given block.

Figure 4:
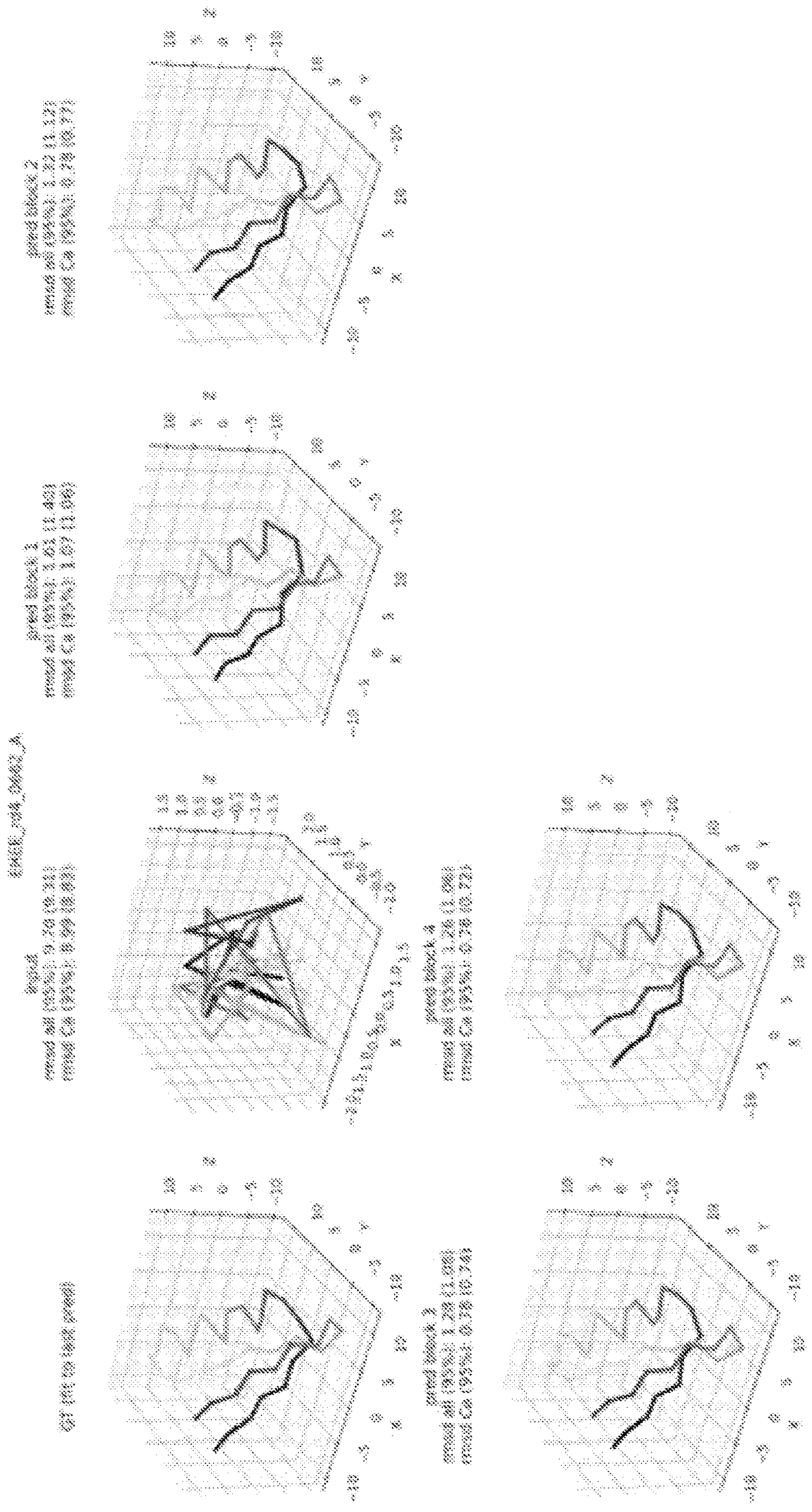
FIG. 4 depicts a visualization of the iterative updates made by a computation model to determine the three-dimensional structure of a protein molecule, in accordance with some example embodiments.

To further illustrate, FIG. 4 depicts a visualization of iterative updates made by the molecule design computation model 117 to generate the three-dimensional structure of the molecule, in accordance with some example embodiments. In the example shown in FIG. 4, the molecule design computation model 117 is a machine learning model having a sequence of four blocks, with each block updating transformations (e.g., Euclidean transformations such as rotation R and/or translation T) of one or more of the coarse-grained nodes in the initial three-dimensional structure of the molecule (shown in block 0) to derive the three-dimensional structure of the molecule (shown in block 4). As shown in FIG. 4, each update to the transformations (e.g., Euclidean transformations such as rotation R and/or translation T) applied to one or more of the coarse-grained nodes in the initial three-dimensional structure (shown in block 0) may progressively reduce or minimize a loss representative of a deviation between the initial three-dimensional structure of the molecule and a ground truth three-dimensional structure of the molecule. In the example shown in FIG. 4, the initial three-dimensional structure (shown in block 0) may be associated with a loss of 0.8906, which decreases substantially over subsequent updates such that the final three-dimensional structure of the molecule (shown in block 4) is associated with a loss of 0.1797.

Figure 5A:
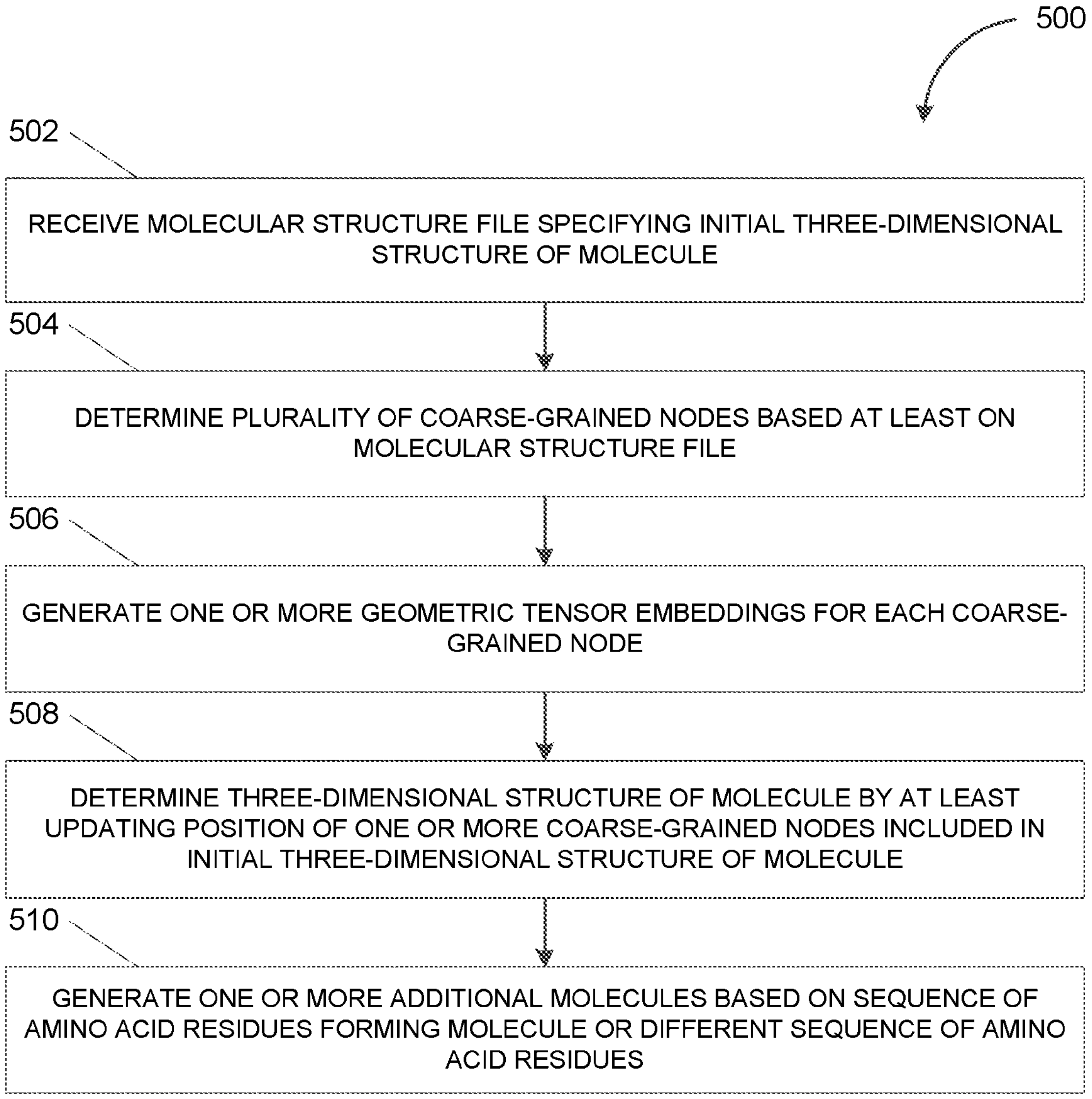
FIG. 5A depicts a flowchart illustrating an example of a process for protein structure and property prediction, in accordance with some example embodiments.
Figure 5B:
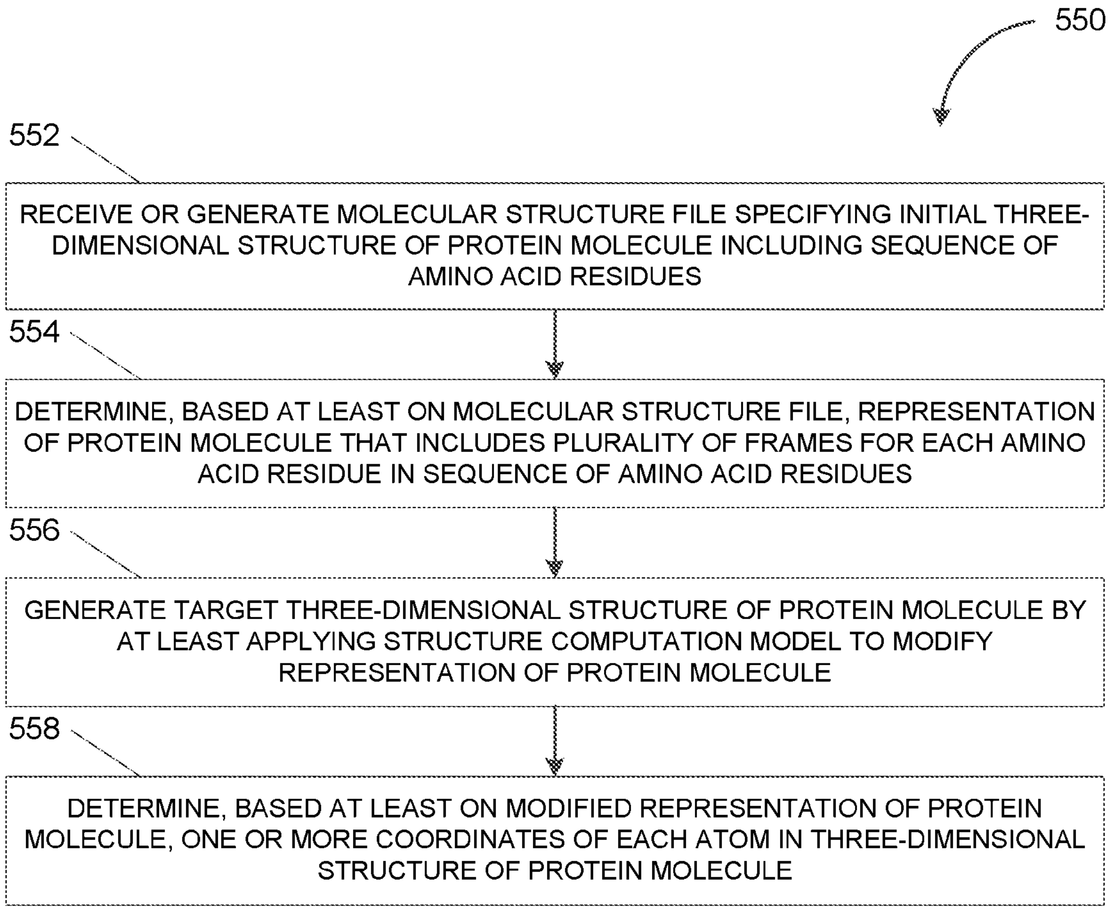
FIG. 5B depicts a flowchart illustrating another example of a process for protein structure and property prediction, in accordance with some example embodiments.
Figure 5C:
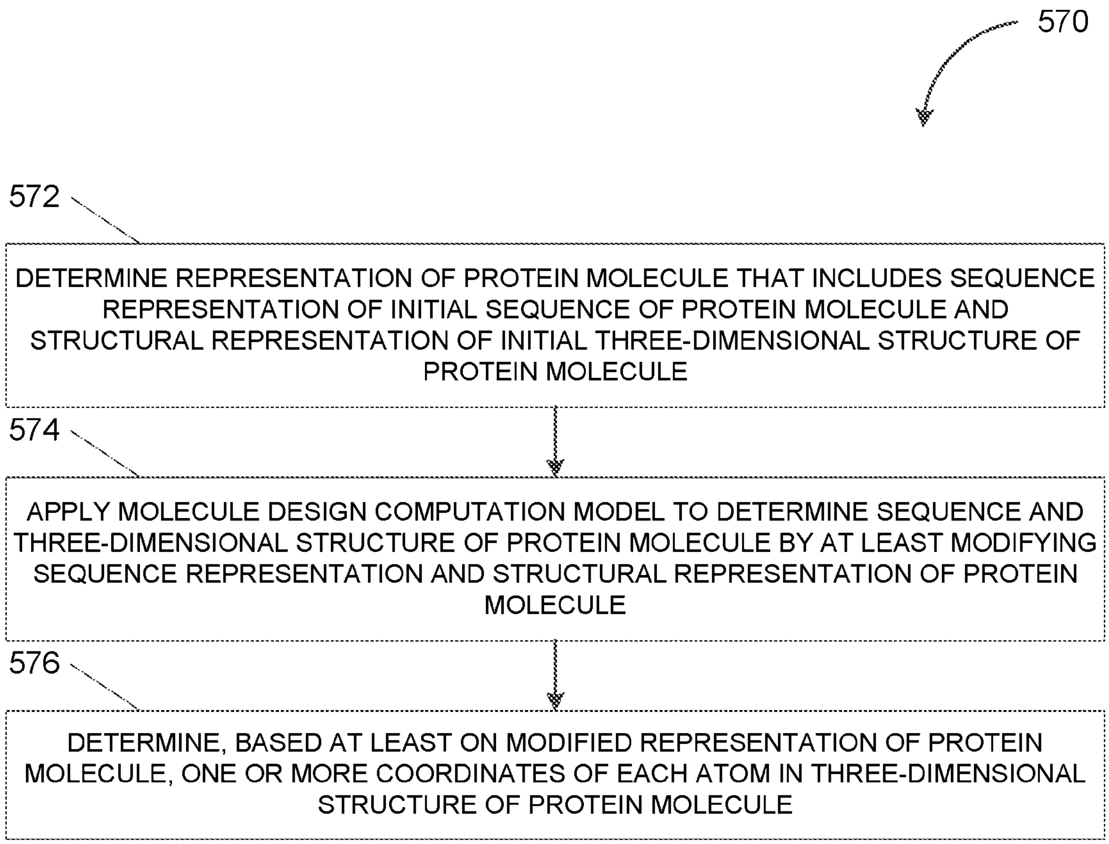
FIG. 5C depicts a flowchart illustrating another example of a process for protein structure and property prediction, in accordance with some example embodiments.

As noted previously, the protein design engine 110 may implement a generative design process that integrates sequence and structure design in a variety of different ways. FIG. 5A-5B illustrate examples in which the protein design engine 110 applies the sequence design computation model 113 to generate the protein sequence before applying the molecule design computation model 117 to determine, based at least on a representation of the protein sequence, the three-dimensional structure of the protein sequence. In each of these cases, the molecule design computation model 117 may operate on a different structural representation of the initial three-dimensional structure of the protein sequence (e.g., coarse-grained (CG) node representation in FIG. 5A and backbone torsion (BBT) representation in FIG. 5B). Alternatively, FIG. 5C illustrates another example in which the protein design engine 110 applies the molecule design computation model 117 to simultaneously determine the identities of the amino acid residues in the protein sequence and the corresponding three-dimensional structure. That is, in some cases, the molecule design computation model 117 may operate on a sequence representation (e.g., a logit representation, a one-hot-encoded representation, and/or the like) of an initial sequence of amino acid residues forming the protein sequence as well as a structural representation (e.g., a coarse-grained (CG) node representation or a backbone torsion (BBT) representation) of an initial three-dimensional structure of the protein sequence to determine the identities of the amino acid residues in the protein sequence as well as the three-dimensional structure of the protein sequence.

To further illustrate, the ontological relationship between the representation of a molecule (e.g., a protein molecule and/or the like), which can include a structural representation of the three-dimensional structure of the molecule and, in some cases, a sequence representation of the amino acid residues forming the molecule, are shown in Table 1 below.

TABLE 1

| REPRESENTATION OF A MOLECULE | |
|---|---|
| SEQUENCE REPRESENTATION | STRUCTURAL REPRESENTATION |
| One-Hot-Encoded Representation: the identity of each amino acid residue in a protein sequence is represented by a one-hot-encoded vector having a value of "1" at the position in the one-hot-encoded vector corresponding to the amino acid residue occupying the position in the protein sequence and a value of "0" at the other positions in the one-hot-encoded vector.<br>OR<br>Logit Representation: the identity of each amino acid residue in a protein sequence is represented by a logit vector enumerating a probability distribution (e.g., categorical distribution) across the set of possible amino acid residues (e.g., 20 canonical amino acid residues). | Coarse-Grained (CG) Node: the atoms in each amino acid residue are grouped into one or more coarse-grained (CG) nodes, each of which being a structural body (e.g., rigid bodies, flexible bodies, and/or the like) that moves as a collective whole.<br>OR<br>Backbone Torsion (BBT): the spatial arrangement of the atoms in each amino acid residue are determined by the translation of the backbone atoms, the rotation of the backbone atoms, and one or more torsion angles formed by the sidechain atoms |

FIG. 5A depicts a flowchart illustrating an example of a process 500 for molecular structure and property prediction, in accordance with some example embodiments. Referring to FIGS. 1A-1B, 2A-2B, 3A-3B, 4, and 5A, the process 500 may be performed by the design system 100, for example, by the molecule design engine 110, and the molecular analysis engine 120. In some cases, the process 500 may implement a generative design process in which the molecule design engine 110 operates on a coarse-grained (CG) node representation of a molecule. Moreover, the process 500 may implement a generative design process that integrates structural and property prediction as a part of a pipeline for generating various molecules including, for example, protein molecules, small molecules, nucleic acids, polysaccharides, glycolipids, and/or the like.

At 502, a molecular structure file specifying an initial three-dimensional structure of a molecule may be received. In some example embodiments, the molecule design engine 110 may apply the sequence design computation model 113 to generate a protein sequence (e.g., a sequence of amino acid residues) for a protein molecule, for example, based on another sequence of amino acid residues (e.g., a seed sequence). In some cases, the sequence design computation model 113 generates the protein sequence by at least determining the identities of each amino acid residue in the protein sequence. Moreover, in some cases, the sequence design computation model 113 may include one or more machine learning models trained to generate the first sequence of amino acid residues by sampling, based on the second sequence of amino acid residues, a data distribution learned by the one or more machine learning models during training. Alternatively, the molecule design engine 110 may receive, from a different source, such as a different sequence design platform, the protein sequence or the corresponding molecular structure file (e.g., a protein structure file) specifying the initial three-dimensional structure of the protein sequence. In some cases, upon receiving or generating the protein sequence, the molecule design engine 110 may generate a molecular structure file (e.g., a protein structure file) specifying the initial three-dimensional structure of the protein sequence including by enumerating the individual atoms (e.g., heavy atoms) forming each of the amino acid residues in the protein sequence.

At 504, a plurality of coarse-grained nodes may be determined based at least on the molecular structure file. In some example embodiments, the representation generator 115 may generate, based at least on the molecular structure file, a coarse-grained (CG) node representation of the initial three-dimensional structure of the protein sequence. To generate the coarse-grained node representation of the protein sequence, the representation generator 115 may start by grouping, into one or more coarse-grained nodes, the atoms (e.g., heavy atoms) forming each of the amino acid residues in the protein sequence. As such, each coarse-grained node may correspond to a structural body (e.g., a rigid body, a flexible or variable body, and/or the like) of two or more of the atoms (e.g., heavy atoms) forming an amino acid residue in the protein sequence. In some cases, the structural body may be a rigid structural body that includes a group of two or more atoms whose locations are fixed with respect to the coordinates of the structural body. In other words, each coarse-grained node operates as a solitary semantic unit such that the relative positions of the constituent atoms remain fixed. A change in the position and/or orientation of a coarse-grained node does not change the relative position of the atoms included in the coarse-grained node.

At 506, one or more geometric tensor embeddings may be generated for each coarse-grained node. In some example embodiments, the representation generator 115 may further generate a numerical representation of each coarse-grained node associated with the protein sequence. In particular, the representation generator 115 may generate, for each coarse-grained node, a numerical representation that describes the rotation of the coarse grained node in three-dimensional space. For example, in some cases, the structural analysis engine 110 may determine, for each coarse-grained node, a numerical representation in the form of a set of one or more geometric tensors having a configurable maximum degree L. In this context, each geometric tensor may be steered by applying one or more elements from the three-dimensional rotation group (e.g., irreducible representations of SO(3) group). For instance, the rotation R of a coarse-grained node in three-dimensional space may be represented by one or more geometric tensors that have been subjected to coordinate transformations defined by one or more elements from the three-dimensional rotation group.

At 508, the three-dimensional structure of the molecule may be generated by at least updating a position of one or more coarse-grained nodes in the initial three-dimensional structure of the molecule. In some example embodiments, the molecule design engine 110 may apply the molecule design computation model 117 to determine, based at least on the geometric tensor embeddings of the coarse-grained (CG) nodes representative of the initial three-dimensional structure of the protein sequence, the three-dimensional structure of the protein sequence. The molecule design computation model 117 may determine the three-dimensional structure of the protein sequence by performing successive updates to the position of one or more coarse-grained nodes in the initial three-dimensional structure of the protein sequence. For example, in some cases, the molecule design computation model 117 may update the position of one or more coarse-grained nodes by at least translating and/or rotating the one or more coarse-grained nodes (e.g., updating to the rotation R and/or translation T of the one or more of the coarse-grained nodes). Moreover, in some instances, the molecule computation model 117 may include a sequence of blocks, with each block performing a separate and incremental update to the position of one or more coarse-grained nodes in the initial three-dimensional structure of the protein sequence. For instance, the molecule design computation model 125 may include a first block that performs a first update to the position of one or more coarse-grained nodes in the initial three-dimensional structure of the protein sequence followed by a second block that performs a second update to the position of one or more coarse-grained nodes in the initial three-dimensional structure of the protein sequence.

At 510, one or more additional molecules may be generated based on a sequence of amino acid residues forming the molecule or a different sequence of amino acid residues. In some example embodiments, the molecule design computation model 117 may be applied to determine the three-dimensional structure of the protein sequence to be associated with one or more desirable properties, such as a particular energy range, a binding affinity and/or binding specificity toward another molecule (e.g., a viral antigen, a tumor antigen, and/or the like), and/or the like. Alternatively and/or additionally, the molecule design computation model 117 may be applied to determine the three-dimensional structure of the protein sequence to be suitable or configured for one or more downstream tasks. For example, in some cases, the molecular analysis engine 120 may apply the molecular property computation model 125 to determine, based at least on the three-dimensional structure of the protein sequence determined by the molecule design computation model 117, one or more properties of the protein sequence including, for example, binding affinity towards another molecule (e.g., a viral antigen, a tumor antigen, and/or the like), specificity towards another molecule, nonspecificity, stability (e.g., conformation stability, thermodynamic stability, robustness to different environmental stresses such as protease resistance, and/or the like), nonimmunogenicity, human-ness, self-association (or non-aggregation), chemical liabilities (e.g., aspartate isomerization, oxidation, deamidation), developability, and/or the like.

In some example embodiments, the three-dimensional structure of the protein sequence may be used as a part of a generative design process that integrates structural and property prediction as a part of a pipeline for generating protein sequences. For example, in instances where the protein sequence is determined to exhibit a desirable three-dimensional structure and/or a desirable property (e.g., the three-dimensional structure of the protein sequence corresponds to the desirable three-dimensional structure and/or a three-dimensional structure associated with the desirable property), the molecule design engine 110 may generate one or more additional protein sequences (e.g., sequences of amino acid residues) based on the protein sequence (e.g., as a seed sequence). Alternatively, in cases where the protein sequence is determined to lack a desirable three-dimensional structure and/or a desirable property, the design engine 110 may generate the one or more additional protein sequences (e.g., sequences of amino acid residues) based on a different sequence of amino acid residues (e.g., as a seed sequence) instead of the protein sequence.

In some cases, the three-dimensional structure of the protein sequence may be generated as a part of constructing a design library of protein sequences, such as antibodies or nanobodies, having a certain three-dimensional structure and/or desirable properties. For example, the design library may be a combinatorial library enumerating, for each position of a protein sequence, a probability distribution of the different amino acid residues that may occupy the position such that the resulting protein sequence has an above-threshold probability of exhibiting the three-dimensional structure and/or the desirable properties associated with the three-dimensional structure.

Alternatively, instead of a coarse-grained (CG) node representation of the three-dimensional structure of the protein sequence, the molecule design engine 110 may generate and operate on a backbone torsion (BBT) representation of the three-dimensional structure of the protein sequence. In some example embodiments, the backbone torsion (BBT) representation of the protein sequence may include, for each constituent amino acid residue in the protein sequence, a plurality of frames. Each frame may correspond to a degree-of-freedom (DoF) for the molecule design computation model 117 to update the initial three-dimensional structure of the protein sequence. For example, in some cases, the plurality of frames for a single amino acid residue in the protein sequence may include a first set of frames specifying a geometric state of the backbone of the amino acid residue. Moreover, the plurality of frames for the amino acid residue may include a second set of frames specifying one or more torsion angles present in a sidechain of the amino acid residue.

FIG. 5B depicts a flowchart illustrating an example of a process 550 for molecular structure and property prediction, in accordance with some example embodiments. Referring to FIGS. 1A-1B, 2A-2B, 3A-3B, 4, and 5B, the process 550 may be performed by the design system 100, for example, by the molecule design engine 110. The example of the process 550 shown in FIG. 5B may implement a generative design process in which the molecule design engine 110, for example, the molecule design computation model 117, operates on a backbone torsion (BBT) representation of a molecule, such as a protein molecule, in order to determine the three-dimensional structure of the molecule.

At 552, the molecule design engine 110 may receive or generate a molecular structure file specifying an initial three-dimensional structure of a protein molecule including a sequence of amino acid residues. For example, in some cases, the molecule design engine 110 may apply the sequence design computation model 113 to generate a protein sequence for a protein molecule based on another protein sequence (e.g., a seed sequence) including by determining the identities of each amino acid residue in the protein sequence. In some cases, the molecule design engine 110 may receive, from a different source such as a difference sequence design platform, the protein sequence or a corresponding molecular structure file specifying the initial three-dimensional structure of the protein sequence. In some cases, upon receiving or generating the protein sequence, the molecule design engine 110 may generate a molecular structure file (e.g., a protein structure file) specifying the initial three-dimensional structure of the protein sequence including by enumerating the individual atoms (e.g., heavy atoms) forming each of the amino acid residues in the protein sequence. The molecular structure file may be a protein structure file specifying the initial three-dimensional structure of the protein sequence by at least enumerating the atoms (e.g., heavy atoms) forming each amino acid residue in the protein sequence.

At 554, the molecule design engine 110 may determine, based at least on the molecular structure file, a representation of the protein molecule that includes a plurality of frames for each amino acid residue in the sequence of amino acid residues. In some example embodiments, the representation generator 115 may determine the backbone torsion (BBT) representation of the protein molecule to include, for each amino acid residue, a plurality of frames specifying the geometric state of the backbone and the sidechain of the amino acid residue. In some cases, each frame may correspond to a degree-of-freedom (DoF) for the molecule design computation model 117 to update the three-dimensional structure of the protein molecule. For example, the plurality of frames associated with an amino acid residue may include a first set of frames specifying the geometric state of the backbone of the amino acid residue and a second set of frames specifying the torsions angles in the sidechain of the amino acid residue. In some cases, the first set of frames may include a first frame specifying the translation and rotation of the backbone as well as a second frame specifying a torsion angle present therein. Alternatively, in some cases, the first set of frames may include, for each torsion angle present in the backbone of the amino acid residue, a corresponding frame. As described in more details below, the second set of frames may include a frame for each torsion angle present in the sidechain of the amino acid residue.

To further illustrate, consider a protein molecule with an N quantity of amino acid residues. In some cases, the representation generator 115 may determine the backbone torsion (BBT) representation of the protein molecule by at least assigning each residue i=1, . . . , N degrees of freedom (DoF) in backbone translation $x_i$=$R^3$, backbone rotation $r_i$=SO(3), and five torsion angles (one for oxygen (O) and four for the side chain angles):

$$(\theta^q)_{q=0}^4 = (\psi_O, \chi_1, \ldots, \chi_4)$$

and $\theta^q \in$ SO(2). The aforementioned degrees of freedom (DoF) may be applicable when the three-dimensional structure of the protein molecule is modified by the molecule design computation model 117. That is, to determine the three-dimensional structure of the protein molecule, the molecule design computation model 117 may be limited to modifying the initial three-dimensional structure of the protein molecule within one or more the aforementioned degrees of freedom. For example, to determine the three-dimensional structure of the protein molecule, the molecule design computation model 117 may modify translate and/or rotate the backbone of one or more of the N quantity of amino acid residues in the protein molecule. Alternatively and/or additionally, to determine the three-dimensional structure of the protein molecule, the molecule design computation model 117 may modify the torsion angle of the oxygen (O) atom in the backbone and/or the side chain torsion angles in one or more of the N quantity of amino acid residues in the protein molecule.

In some cases, the backbone atoms and torsion angles that are present in each type of amino acid residue are shown in Table 3 below.

TABLE 3

| aatype | bb | ψ | $X_1$ | $X_2$ | $X_3$ | $X_4$ |
|---|---|---|---|---|---|---|
| ALA | N, $C^{\alpha}$, C, $C^{\beta}$ | O | — | — | — | — |
| ARG | N, $C^{\alpha}$, C, $C^{\beta}$ | O | $C^{\gamma}$ | $C^{\delta}$ | $N^{\epsilon}$ | $N^{\eta 1}$, $N^{\eta 2}$, $C^{\zeta}$ |
| ASN | N, $C^{\alpha}$, C, $^{\beta}$ | O | $C^{\gamma}$ | $N^{\delta 2}$, $O^{\delta 1}$ | — | — |
| ASP | N, $C^{\alpha}$, C, $C^{\beta}$ | O | $C^{\gamma}$ | $O^{\delta 1}$, $O^{\delta 2}$ | — | — |
| CYS | N, $C^{\alpha}$, C, $C^{\beta}$ | O | $S^{\gamma}$ | — | — | — |
| GLN | N, $C^{\alpha}$, C, $C^{\beta}$ | O | $C^{\gamma}$ | $C^{\delta}$ | $N^{\epsilon 2}$, $O^{\epsilon 1}$ | — |
| GLU | N, $C^{\alpha}$, C, $C^{\beta}$ | O | $C^{\gamma}$ | $C^{\delta}$ | $O^{\epsilon 1}$, $O^{\epsilon 2}$ | — |
| GLY | N, $C^{\alpha}$, C | O | — | — | — | — |
| HIS | N, $C^{\alpha}$, C, $C^{\beta}$ | O | $C^{\gamma}$ | $C^{\delta 2}$, $N^{\delta 1}$, $C^{\epsilon 1}$, $N^{\epsilon 2}$ | — | — |
| ILE | N, $C^{\alpha}$, C, $C^{\beta}$ | O | $C^{\gamma 1}$, $C^{\gamma 2}$ | $C^{\delta}$ | — | — |
| LEU | N, $C^{\alpha}$, C, $C^{\beta}$ | O | $C^{\gamma}$ | $C^{\delta 1}$, $C^{\delta 2}$ | — | — |
| LYS | N, $C^{\alpha}$, C, $C^{\beta}$ | O | $C^{\gamma}$ | $C^{\delta}$ | $C^{\epsilon}$ | $N^{\zeta}$ |
| MET | N, $C^{\alpha}$, C, $C^{\beta}$ | O | $C^{\gamma}$ | $S^{\delta}$ | $C^{\epsilon}$ | — |
| PHE | N, $C^{\alpha}$, C, $C^{\beta}$ | O | $C^{\gamma}$ | $C^{\delta 1}$, $C^{\delta 2}$, $C^{\epsilon 1}$, $C^{\epsilon 2}$, $C^{\zeta}$ | — | — |
| PRO | N, $C^{\alpha}$, C, $C^{\beta}$ | O | $C^{\gamma}$ | $C^{\delta}$ | — | — |
| SER | N, $C^{\alpha}$, C, $C^{\beta}$ | O | $O^{\gamma}$ | — | — | — |
| THR | N, $C^{\alpha}$, C, $C^{\beta}$ | O | $C^{\gamma 2}$, $O^{\gamma 1}$ | — | — | — |
| TRP | N, $C^{\alpha}$, C, $C^{\beta}$ | O | $C^{\gamma}$ | $C^{\delta 1}$, $C^{\delta 2}$, $C^{\epsilon 2}$, $C^{\epsilon 3}$, $N^{\epsilon 1}$, $C^{\eta 2}$, $C^{\zeta 2}$, $C^{\zeta 3}$ | — | — |
| TYR | N, $C^{\alpha}$, C, $C^{\beta}$ | O | $C^{\gamma}$ | $C^{\delta 1}$, $C^{\delta 2}$, $C^{\epsilon 1}$, $C^{\epsilon 2}$, $C^{\eta}$, $C^{\zeta}$ | — | — |
| VAL | N, $C^{\alpha}$, C, $C^{\beta}$ | O | $C^{\gamma 1}$, $C^{\gamma 2}$ | — | — | — |

Further illustration is provided at FIG. 6A, which depicts an exemplary atomic structure of an amino acid residue.

Figure 7A:
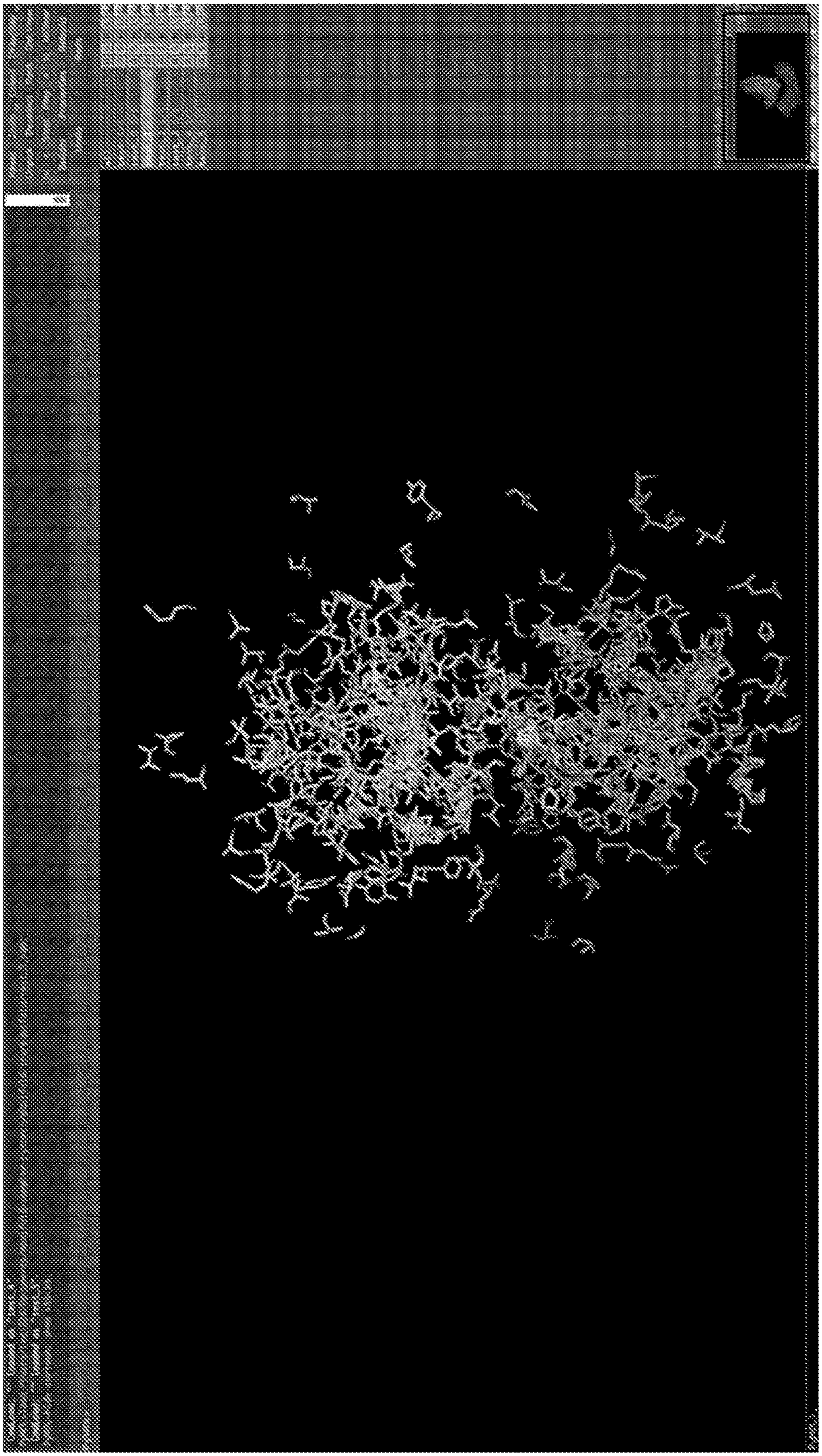
FIG. 7A depicts a screenshot illustrating an example of a protein molecule undergoing backbone translations, in accordance with some example embodiments.
Figure 7B:
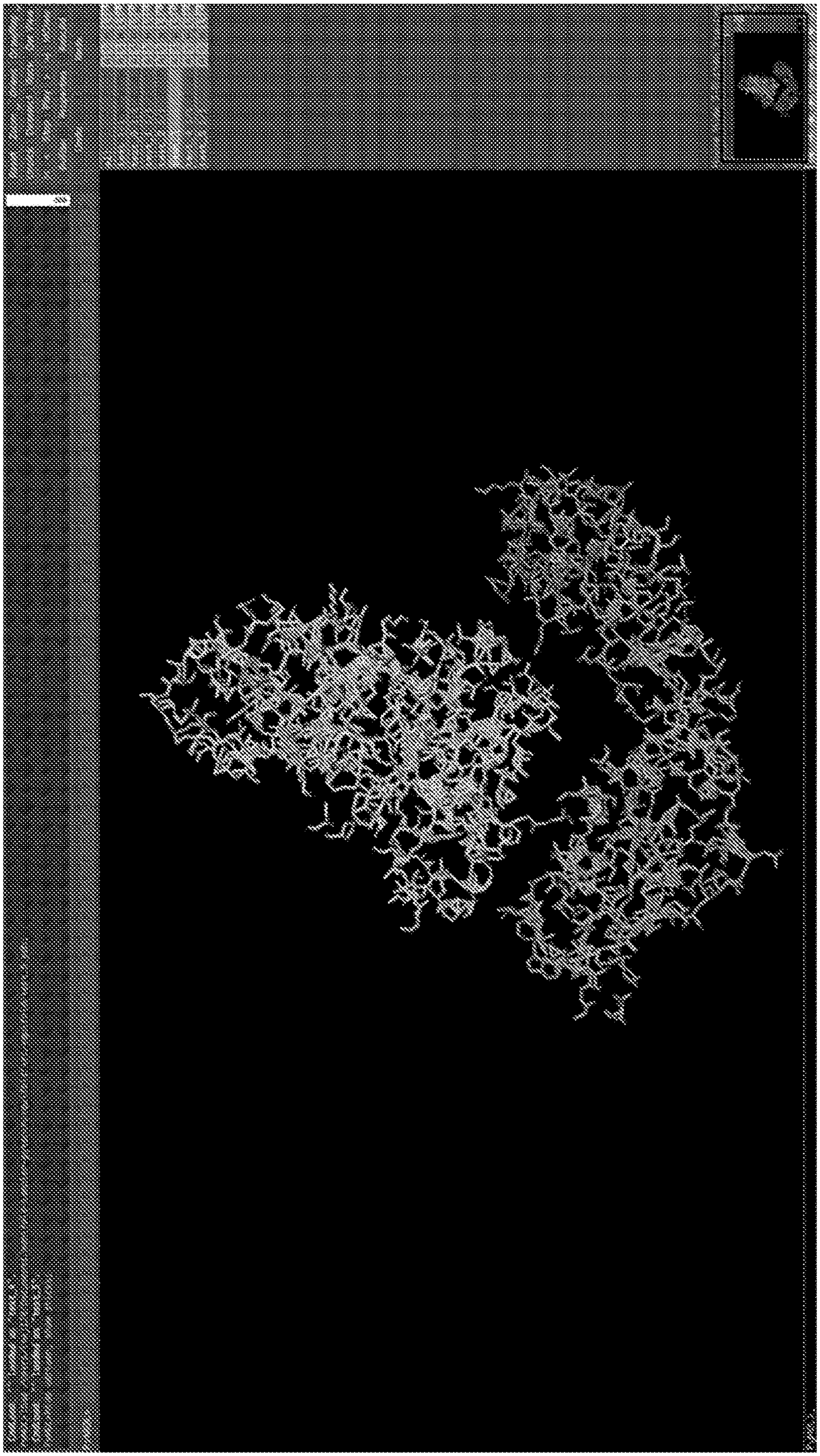
FIG. 7B depicts a screenshot illustrating an example of a protein molecule undergoing backbone rotations, in accordance with some example embodiments.
Figure 7C:
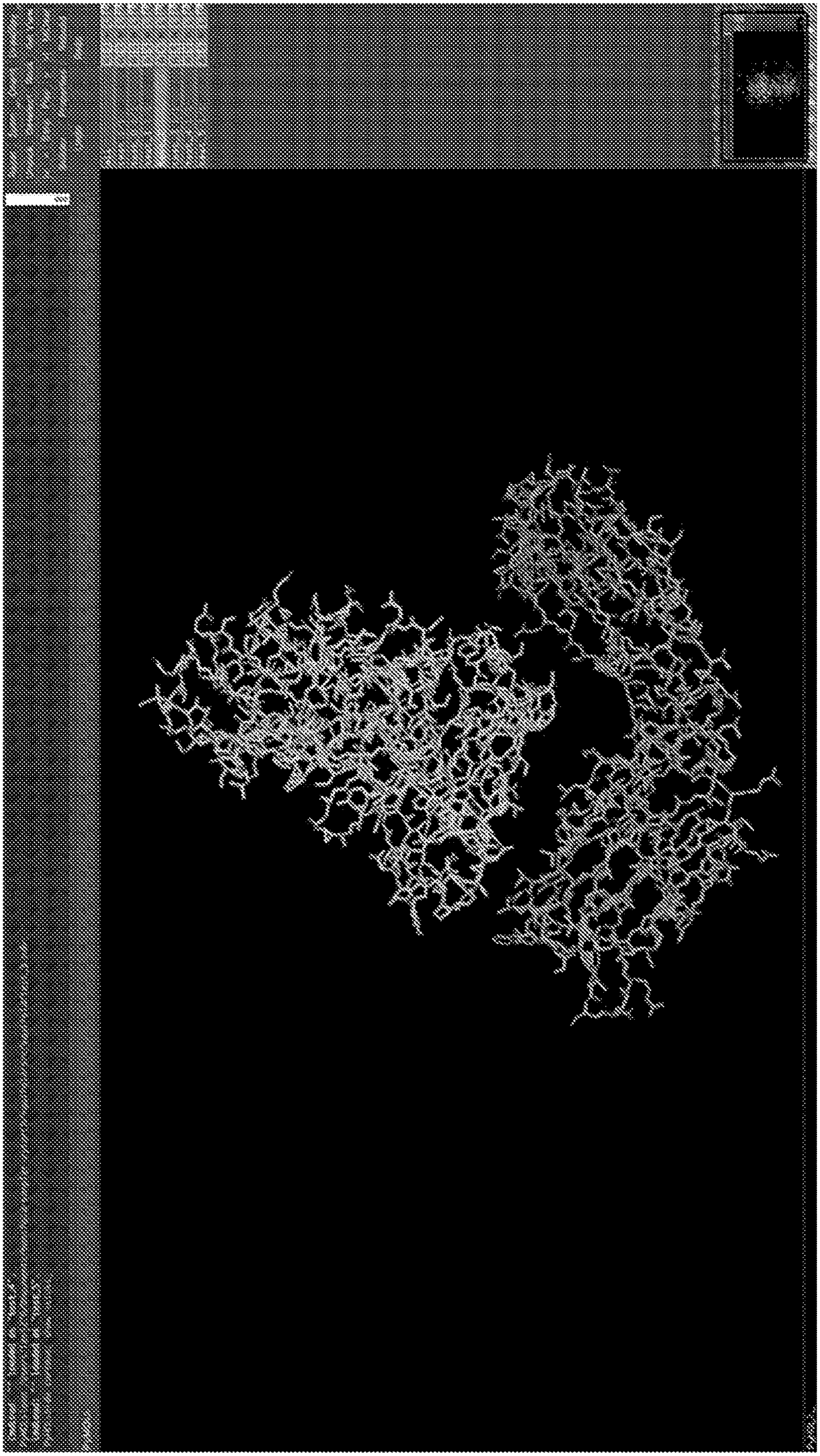
FIG. 7C depicts a screenshot illustrating another example of a protein molecule undergoing changes in sidechain torsion angle, in accordance with some example embodiments.
Figure 8A:
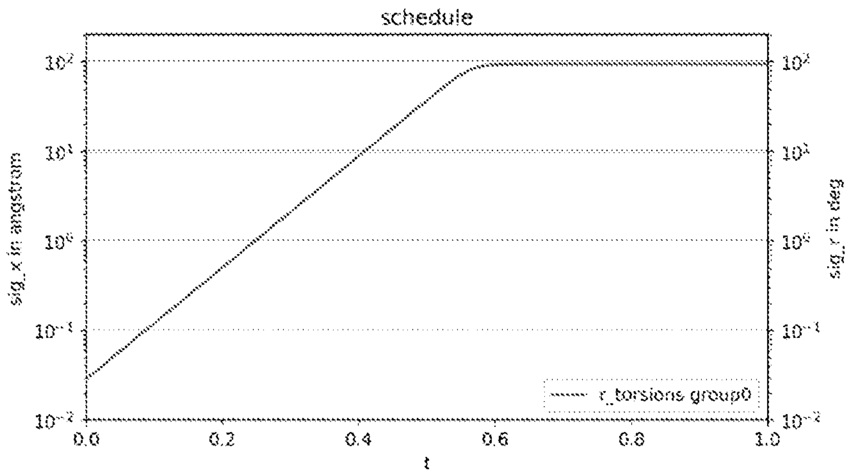
FIG. 8A depicts a graph illustrating an example of a noise schedule for a diffusion model modifying the torsion angles of a protein structure, in accordance with some example embodiments.
Figure 8B:
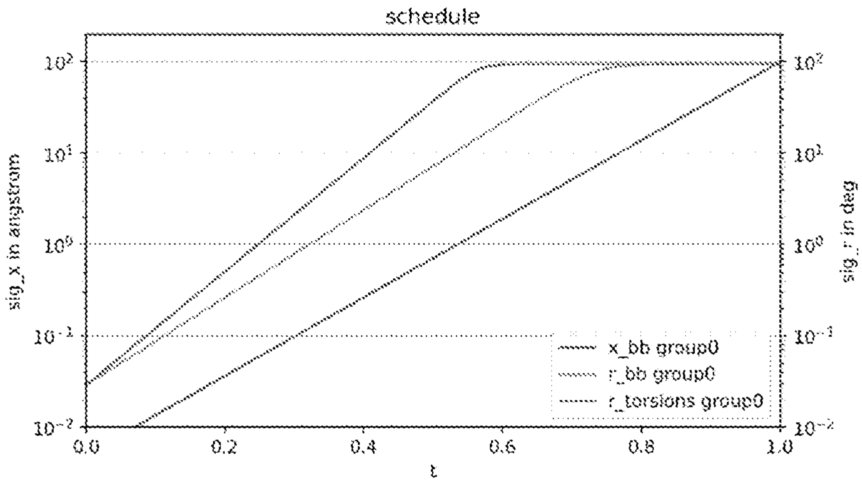
FIG. 8B depicts a graph illustrating another example of a noise schedule for a diffusion model modifying all degrees of freedom of a protein structure except center of mass, in accordance with some example embodiments.
Figure 8C:
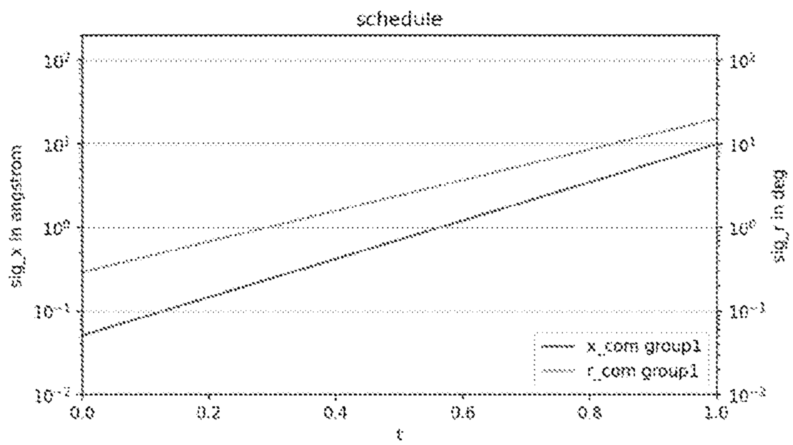
FIG. 8C depicts a graph illustrating another example of a noise schedule for a diffusion model performing molecular docking between two molecules by modifying a respective center of mass of the two molecules, in accordance with some example embodiments.
Figure 8D:
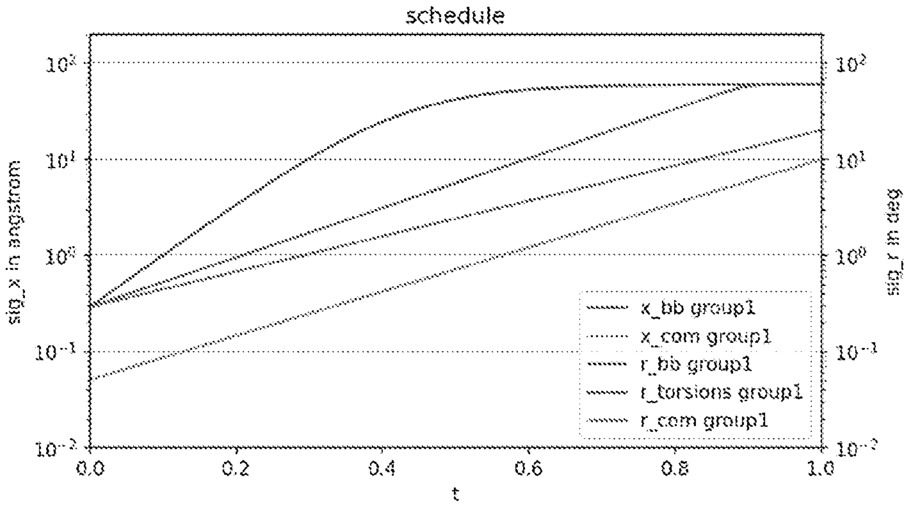
FIG. 8D depicts a graph illustrating another example of a noise schedule for a diffusion model performing molecular docking between two molecules by modifying a center of mass.

At 556, the molecule design engine 110 may determine the three-dimensional structure of the protein molecule by at least applying the molecule design computation model 117 to modify the representation of the protein molecule. In some example embodiments, the molecule design computation model 117 may modify the backbone torsion (BBT) representation of the protein molecule by at least updating the first set of frames to alter the geometric state of the backbone of one or more amino acid residues. For example, in some cases, the molecule design computation model 117 may update the first set of frames to alter the translation and rotation of the backbone and/or one or more torsion angles present in the backbone. Alternatively and/or additionally, the molecule design computation model 117 may modify the backbone torsion (BBT) representation of the protein molecule by at least updating the second set of frames to alter one or more of the torsion angles present in the sidechain of the amino acid residue. To illustrate, FIG. 7A depicts a screenshot illustrating an example of a protein molecule in which the backbones of its constituent amino acid residues are translated to determine the three-dimensional structure of the protein molecule. FIG. 7B depicts a screenshot illustrating an example of a protein molecule in which the backbones of its constituent amino acid residues are rotated to determine the three-dimensional structure of the protein molecule. FIG. 7C depicts a screenshot illustrating an example of a protein molecule in which the sidechain torsion angles of its constituent amino acid residues are altered to determine the three dimensional structure of the protein molecule.

In some example embodiments, the molecule design computation model 117 may include a machine learning model trained to determine the three-dimensional structure of the protein molecule by at least to denoising the initial three-dimensional structure of the protein molecule. In some cases, the machine learning model may denoise the initial three-dimensional structure of the protein molecule by at least performing a sequence of updates to the backbone torsion (BBT) representation of the protein molecule. In some cases, the machine learning model may be trained to reduce or minimize a loss function, such as a frame aligned point error (FAPE) loss function, a structure violation loss function, and/or the like, associated with each successive update to the initial three-dimensional structure of the protein molecule. Alternatively and/or additionally, the machine learning model may be trained to reduce or minimize an energy function associated with each successive update successive update to the initial three-dimensional structure of the protein molecule.

In some example embodiments, the molecule design computation model 117 may include a diffusion model that performs a sequence of modifications to the initial three-dimensional structure of the protein molecule, each of which removing a portion of noise present in the initial three-dimensional structure of the protein molecule. An exemplary diffusion model is described at FIG. 6B. Moreover, in some cases, each successive update made by the diffusion model may generate an output that is equivariant to special Euclidean group SE(3) transformations. For example, in some cases, the diffusion model may perform, at a first timepoint, a first update to the backbone torsion (BBT) representation of the protein molecule in order to remove a first quantity of noise present in the initial three-dimensional structure of the protein molecule, Furthermore, the diffusion model may, at a second timepoint, perform a second update to the backbone torsion (BBT) representation of the protein molecule in order to remove a second quantity of noise present in the initial three-dimensional structure of the protein molecule.

In some cases, the diffusion model may denoise the initial three-dimensional structure of the protein molecule over a large quantity of successive updates (e.g., 2000 successive denoising operations). In doing so, the diffusion model may be capable of performing highly nuanced modifications to refine the three-dimensional structure of the protein molecule. Contrastingly, the geometric deep learning model described above, which includes far fewer blocks (e.g., 8 blocks in an equivariant neural network (ENN)), may update the initial three-dimensional structure of the protein molecule over far fewer and much less subtle updates.

At 558, the molecule design engine 110 may determine, based at least on the modified representation of the protein molecule, one or more coordinates of each atom in the three-dimensional structure of the protein molecule. In some example embodiments, the molecule design engine 110 may determine, based at least on the plurality of frames of each amino acid residue in the modified backbone torsion (BBT) representation of the protein molecule, one or more coordinates (e.g., three-dimensional coordinates) of each atom in the three-dimensional structure of the protein molecule. For example, in some cases, the molecule design engine 110 may determine, based at least on the modified backbone torsion (BBT) representation of the protein molecule, one or more coordinates of the backbone atoms in the protein molecule. Thereafter, the molecule design engine 110 may determine, based at least on the coordinates of the backbone atoms in the protein molecule, one or more coordinates of the sidechain atoms in the protein molecule. An example of the algorithm for computing the coordinates of each atom in the three-dimensional structure of the protein molecule is shown in Table 4 below.

TABLE 4

| | |
|---|---|
| *def computeAllAtomCoordinates*$\left(T_i, \vec{\alpha}_i^f, F_i^{aatype}\right)$: | |
| 1: | $\hat{\vec{a}}_i^f = \vec{a}_i^f / \left\| \vec{a}_i^f \right\|$ |
| 2: | $\left(\vec{\omega}_i, \vec{\phi}_i, \vec{\psi}_i, \vec{\chi}_{1_i}, \vec{\chi}_{2_i}, \vec{\chi}_{3_i}, \vec{\chi}_{4_i}\right) = \hat{\vec{a}}_i^f$ |
| # Make extra backbone frames. | |
| 3: | $r_i = F_i^{aatype}$ |
| 4: | $T_{i1} = T_i \circ T^{lit}_{r_i,(\omega \to bb)} \circ makeRotX(\vec{\omega}_i)$ |
| 5: | $T_{i2} = T_i \circ T^{lit}_{r_i,(\phi \to bb)} \circ makeRotX(\vec{\phi}_i)$ |
| 6: | $T_{i3} = T_i \circ T^{lit}_{r_i,(\psi \to bb)} \circ makeRotX(\vec{\psi}_i)$ |
| # Make side chain frames (chain them up along the side chain). | |
| 7: | $T_{i4} = T_i \circ T^{lit}_{r_i,(\chi_1 \to bb)} \circ makeRotX\left(\vec{\chi}_{1_i}\right)$ |
| 8: | $T_{i5} = T_{i4} \circ T^{lit}_{r_i,(\chi_2 \to \chi_1)} \circ makeRotX\left(\vec{\chi}_{2_i}\right)$ |
| 9: | $T_{i6} = T_{i5} \circ T^{lit}_{r_i,(\chi_3 \to \chi_2)} \circ makeRotX\left(\vec{\chi}_{3_i}\right)$ |
| 10: | $T_{i7} = T_{i6} \circ T^{lit}_{r_i,(\chi_4 \to \chi_3)} \circ makeRotX\left(\vec{\chi}_{4_i}\right)$ |
| # Map atom literature positions to the global frame. | |
| 11: | $\vec{x}_i^a = concat_{f,a'}\left(\left\{T_i^f \circ \vec{x}^{lit}_{r_i,f,a'}\right\}\right)$ |
| 12: | return $T_i^f, \vec{x}_i^a$ |

In some example embodiments, instead of merely determining the three-dimensional structure of a fixed sequence of amino acid residues, such as a protein sequence generated by the sequence design computation model 113 (or another sequence design platform), the molecule design computation model 117 may be applied to determine the sequence and structure of a protein molecule. That is, in the example of the process 570 shown in FIG. 5C, the molecule design computation model 117 may be applied to determine the identity of every amino acid residue forming a protein molecule as well as the spatial arrangement of the constituent atoms. As described in more detail below, the molecule design computation model 117 may determine the sequence and three-dimensional structure of the protein molecule by simultaneously modifying the corresponding sequence representation and structural representation (e.g., coarse-grained (CG) node representation, backbone torsion (BBT) representation, and/or the like).

FIG. 5C depicts a flowchart illustrating an example of a process 570 for molecular structure and property prediction, in accordance with some example embodiments. Referring to FIGS. 1A-1B, 2A-2B, 3A-3B, 4, and 5C, the process 570 may be performed by the design system 100, for example, by the molecule design engine 120. The example of the process 570 shown in FIG. 5C may implement a generative design process in which the molecule design engine 110, for example, the molecule design computation model 117, operates on a sequence representation and a structural representation (e.g., a coarse-grained (CG) node representation, a backbone torsion (BBT) representation, and/or the like) of a protein molecule in order to determine sequence as well as the three-dimensional structure of the protein molecule.

At 572, the molecule design engine 110 may determine a representation of a protein molecule that includes a sequence representation of an initial sequence of the protein molecule and a structural representation of an initial three-dimensional structure of the protein molecule. In some example embodiments, the representation generator 115 may generate a representation of a protein molecule that includes a sequence representation of the initial sequence of the protein molecule and a structural representation of the initial three-dimensional structure of the protein molecule. In some cases, the structural representation of the initial three-dimensional structure may be a coarse-grained (CG) node representation in which the atoms (e.g., heavy atoms) forming the constituent amino acid residues are represented as a collection of coarse-grained (CG) nodes. Alternatively, the structural representation of the initial three-dimensional structure may be a backbone torsion (BBT) representation that includes, for each amino acid residue in the protein molecule, a plurality of frames specifying the geometric state of the backbone atoms and the sidechain atoms.

In some example embodiments, the sequence representation of the protein molecule may be a logit representation having a plurality of logit vectors, each of which corresponding to a position in the initial sequence of the protein molecule and indicating the identity of the amino acid residue occupying the position by at least enumerating a probability distribution across the set of possible amino acid residues occupying the position. That is, the logit vector for a position in the initial sequence of the protein molecule may include, for each possible amino acid residue, a corresponding probability that the position is occupied by that amino acid residue. Alternatively, the sequence representation of the protein molecule may be a one-hot-encoded representation having a plurality of one-hot-encoded vectors, each of which corresponding to a position in the initial sequence of the protein molecule and having a position corresponding to each amino acid residue in the set of possible amino acid residues. The one-hot-encoded vector for a particular position in the protein sequence may indicate the identity of the amino acid residue occupying that position by at least having the value "1" at a position in the one-hot-encoded vector corresponding to the amino acid residue occupying the position in the protein sequence and the value "0" elsewhere (e.g., [0,0,0, 0, 1, 0, . . . , 0]). The set of amino acid residues may include, in some cases, a "ghost residue" representative of the gap in the sequence of amino acid residues. As such, a position in the sequence of amino acid residues include a gap that is not occupied by any amino acid residue in cases where the probability of the position being occupied by a ghost residue satisfies one or more thresholds. The inclusion of the ghost residues may accommodate length changes as a part of the subsequent generative diffusion process performed, for example, by the molecule design computation model 117.

As noted, in some example embodiments, the representation generator 115 may generate the representation of the protein molecule to include the sequence representation if the initial sequence as well as the structural representation of the initial three-dimensional structure of the protein molecule. Accordingly, in some cases, the representation of the protein molecule may include, for each position within the sequence of amino acid residues forming the protein molecule, a representation (e.g., a logit representation, a one-hot-encoded representation, and/or the like) of the identity of the amino acid residue occupying that position. Furthermore, the representation of the protein molecule may include, for each position within the sequence of amino acid residues forming the protein molecule, a representation (e.g., a coarse-grained (CG) node representation, a backbone torsion (BBT) representation, and/or the like) of the spatial arrangement of the atoms (e.g., heavy atoms) forming the amino acid residue occupying that position. For example, for a single position within the sequence of amino acid residues forming the protein molecule, the representation of the protein molecule may include a logit vector enumerating the probability distribution (e.g., categorical distribution) across the set of possible amino acid residues occupying the position (e.g., a first probability that the position is occupied by Alanine (Ala/A), a second probability that the position is occupied by Arginine (Arg/R), a third probability that the position is occupied by Asparagine (Asn/N), and/or the like). The representation of the protein molecule may further include, for the same position, a representation of the spatial arrangements of the atoms (e.g., heavy atoms) forming the amino acid residue occupying the position. In the case of a coarse-grained (CG) node representation, the representation may include a collection of coarse-grained (CG) nodes, each of which including two or more of the atoms in the amino acid residue. Alternatively, in the case of a backbone torsion (BBT) representation, the representation may include the backbone translation, the backbone rotation, and the torsion angles formed by the atoms in the amino acid residue.

To further illustrate, consider a protein molecule formed by a sequence of N amino acid residues. Each residue $i=1, \ldots, N$ may be associated with the following degrees of freedom, meaning that the molecule design computation model 117 may perform the following modifications when operating on the representation of the protein molecule: (i) residue identity $c_i \in C$ wherein C denotes the set of possible amino acid residues, (ii) backbone translation $x_i = R^3$, (iii) backbone rotation $r_i = SO(3)$, and (iv) torsion angles (e.g., one for backbone oxygen (O) and four for the side chain angles):

$$(\theta^q)_{q=0}^4 = (\psi_O, \chi_1, \ldots, \chi_4)$$

and $\theta^q \in SO(2)$. Collectively, the aforementioned degrees of freedom may be denoted as $$Z = \{Z_i\}_{i=1}^N, \text{ wherein } Z_i = (c_i, x_i, r_i, \theta_i^{q=0}, \ldots, \theta_i^{q=4}).$$

Moreover, in some cases, each of the aforementioned degrees of freedom may correspond to frames, which are modified by the molecule design computation model 117 when performing a generative process (e.g., a generative diffusion process) to determine the sequence and three-dimensional structure of the protein molecule.

At 574, the molecule design engine 110 may apply the molecule design computation model 117 to determine the sequence and the three-dimensional structure of the protein molecule by at least modifying the sequence representation and the structural representation of the protein molecule. In some example embodiments, the molecule design computation model 117 may determine the three-dimensional structure of the protein molecule by at least modifying the sequence representation of the initial sequence of the protein molecule along with the structural representation of the three-dimensional structure of the protein molecule. In some cases, the structural representation may be a coarse-grained (CG) node representation or a backbone torsion (BBT) representation of the initial three-dimensional structure of the protein molecule. Moreover, in some cases, the molecule design computation model 117 may be a diffusion model that determines the sequence and the three-dimensional structure of the protein molecule by at least denoising, over a succession of timepoints, the initial sequence and the initial three-dimensional structure of the protein molecule. For example, the denoising of the initial sequence may include operating on the sequence representation of the initial sequence in order to modify the identity of one or more amino acid residues included in the initial sequence. Meanwhile, the denoising of the initial three-dimensional structure may include the molecule design computation model 117 operating on the structural representation of the initial three-dimensional structure to modify the spatial arrangements of the atoms (e.g., heavy atoms) forming the amino acid residues in the protein molecule.

In some example embodiments, where the molecule design computation model 117 determines the sequence and the three-dimensional structure of the protein molecule, the molecule design computation model 117 may perform a diffusion process in which the identity of the amino acid residues are modified as another degree-of-freedom (DoF) in addition to those associated with the spatial arrangements of the constituent atoms. Accordingly, in some cases, the molecule design computation model 117 may be a diffusion model that includes a first diffusion kernel modifying the identity of individual amino acid residues, a second diffusion kernel modifying the backbone translation of each amino acid residue, a third diffusion kernel modifying the backbone rotation of each amino acid residue, and a fourth diffusion kernel modifying the torsion angles in the backbone and sidechain of each amino acid residue. In some cases, the first diffusion kernel, the second diffusion kernel, the third diffusion kernel, and the fourth diffusion kernel may each be parameterized as a neural network including, for example, an equivariant neural network (ENN) that is cognizant of or accounting for the rotational symmetries present in the three dimensional structure of the protein molecule.

In some example embodiments, the molecule design computation model 117 may perform a generative diffusion process in order to determine the sequence and the three-dimensional structure of the protein molecule. In some cases, the molecule design computation model 117 may be a diffusion model that determines the sequence and three-dimensional structure of the protein molecule by at least denoising, over successive timesteps, the initial sequence and the initial three-dimensional structure of the protein molecule. For example, in some cases, the molecule design computation model 117 may remove a first quantity of noise from the representation of the protein molecule before removing a second quantity of noise from the representation of the protein molecule. It should be appreciated that the generative diffusion process may correspond to a reverse diffusion process in which the molecule design computation model 117 removes, from the representation of the protein molecule, noise in accordance to a decreasing noise scale such that less noise is present in the sequence and the three-dimensional structure of the protein molecule at each successive timestep. However, the training of the molecule design computation model 117 may also include a forward diffusion process in which noise is added in accordance to an increasing noise scale such that more noise is present in the three-dimensional structure of a protein molecule at each successive timestep. The training of the molecule design computation model 117 may thus include learning the reverse diffusion process to restore the correct sequence and three-dimensional structure of a protein molecule from a noisy representation of the protein molecule in which the identity of the amino acid residues forming the protein molecule is uncertain and the three-dimensional structure of the protein molecule is random.

In some example embodiments, the training of the molecule design computation model 117 may include learning the score function of each diffusion kernel (e.g., parameterized by a neural network) included in the molecule design computation model 117. For example, in some cases, the molecule design computation model 117 may be implemented with a stochastic differential equation (SDE) score matching framework in which a stochastic differential equation (SDE) is applied to smoothly transform a sample from a complex data distribution, which in this case may be populated by the ground truth sequence and three-dimensional structures of various known protein molecules, to a corresponding sample in a noise distribution by the injection of noise. A corresponding reverse-time stochastic differential equation (SDE) may be applied to restore the sample from the original complex data distribution (e.g., the original sequence and three-dimensional structure of a protein molecule) by the removal of noise. Equations (2) and (3) above are examples of the aforementioned forward stochastic differential equation (SDE) and reverse stochastic differential equation (SDE).

With reference to Equations (2) and (3), the training of the diffusion model in a stochastic differential equation (SDE) score matching framework may include learning a score-based model $s_\theta(x)$ that approximates, for each possible degree-of-freedom (DoF), the corresponding score function $\nabla_x \log p_t(x)$. For example, in some cases, the score function for the first diffusion kernel modifying the identity of individual amino acid residues may represent the change in log data density of the complex data distribution associated with known protein sequences. Learning the score function of the first diffusion kernel may enable samples to be drawn, over successive timesteps during the reverse diffusion process (e.g., by applying Markov chain Monte Carlo sampling with Langevin dynamics), from areas in the original complex data distribution that are more densely populated by known protein sequences. Similarly, the score function of the second diffusion kernel modifying the backbone translation of each amino acid residue may represent the change in log data density of the complex data distribution associated with the backbone translation of known three-dimensional protein structure. Learning the score function of the second diffusion kernel may enable samples to be drawn, over successive timesteps during the reverse diffusion process (e.g., by applying Markov chain Monte Carlo sampling with Langevin dynamics), from areas in the original complex data distribution that are more densely populated by the backbone torsion of known three-dimensional protein structures. The score function of each diffusion kernel may ingest the other degrees of freedom as input. For instance, the score function for the first diffusion kernel modifying the identity of individual amino acid residues may ingest, as input, the backbone translation, the backbone rotation, and the torsion angles of the amino acid residue determined by the corresponding diffusion kernels, thus enabling the score functions of multiple diffusion kernels to be learned simultaneously for the same protein molecule.

In some example embodiments, each diffusion stage may include adding, subsequent to the noise removal, some noise back in the modified representation of the initial sequence and initial three-dimensional structure of the protein molecule. For example, in some cases, upon removing the first quantity of noise from the representation of the protein molecule, the molecule design computation model 117 may add a third quantity of noise back into the backbone torsion (BBT) representation of the protein molecule before the second quantity of noise is removed from the representation of the protein molecule. After the second quantity of noise is removed from the representation of the protein molecule, a fourth quantity of noise may be added back before the representation of the protein molecule is further denoised by the diffusion model. The third quantity and fourth quantity of noise that is added to the backbone torsion (BBT) representation of the protein molecule may be determined based on a noise schedule defining a distribution of noise levels across the sequence of diffusion operations performed by the diffusion model. The addition of noise may compensate for at least some of the errors that may be present in the denoising performed at each timepoint by the diffusion model.

FIG. 6A depicts a schematic diagram illustrating an atomic structure of an example of an amino acid residue 600, in accordance with some example embodiments. In some cases, the backbone torsion (BBT) representation of the amino acid residue 600 may specify the geometric state of the backbone of the amino acid residue 600 in a variety of different ways. In the example of the amino acid residue 600 shown in FIG. 6A, the backbone of the amino acid residue 600 may include a nitrogen (N), an alpha carbon ($C_\alpha$) atom, and a carbonyl group formed by a carbon atom coupled with an oxygen atom. Accordingly, in some cases, the plurality of frames associated with the amino acid residue 600 may include a first frame defining the geometric state of the backbone of the amino acid residue 600 may specify a rotation and a translation of the backbone of the amino acid residue 600. For example, in some cases, the first frame may include an affine transformation matrix that includes a rotation matrix specifying the rotation of the backbone of the amino acid residue 600 as well as a displacement vector specifying the translation of the backbone of the amino acid residue 600. In some cases, along with the first frame specifying the translation and rotation of the backbone of the amino acid residue 600, the plurality of frames associated with the amino acid residue 600 may include a second frame specifying the torsion angle $\psi$ of the rotatable bond between the alpha carbon ($C_\alpha$) atom and the carbonyl group in the backbone of the amino acid residue.

In some cases, instead of the translation and rotation of the backbone of the amino acid residue 600, the geometric state of the backbone of the amino acid residue may be specified by the torsion angles present therein. Accordingly, in some cases, the plurality of frames associated with the amino acid residue 600 may include a first frame specifying the torsion angle $\psi$ of the rotatable bond between the alpha carbon ($C_\alpha$) atom and the carbonyl group in the backbone of the amino acid residue 600, a second frame specifying the torsion angle $\phi$ of the rotatable bond between the alpha carbon ($C_\alpha$) atom and the nitrogen (N) atom, and a third frame specifying the torsion angle $\omega$ of the rotatable bond between the carbon (C) atom and the nitrogen (N) atom in the backbone of the amino acid residue.

Referring again to FIG. 6A, in addition to the frames specifying the geometric state of the backbone of the amino acid residue 600, the plurality of frames associated with the amino acid residue 600 may further include one or more additional frames specifying the torsion angles present in the sidechain of the amino acid residue 600. In the example shown in FIG. 6A, the plurality of frames associated with the amino acid residue 600 may include a frame for each of the torsion angle $\chi_1$ of the rotatable bond between the alpha carbon ($C_\alpha$) atom and the beta carbon ($C_\beta$) atom, the torsion angle $\chi_2$ of the rotatable bond between the beta carbon ($C_\beta$) atom and the gamma carbon ($C_\gamma$) atom, the torsion angle $\chi_3$ of the rotatable bond between the gamma carbon ($C_\gamma$) atom and the delta carbon ($C_\delta$) atom, and the torsion angle $\chi_3$ of the rotatable bond between the delta carbon ($C_\delta$) atom and the nitrogen (N) atom.

In some cases, the backbone torsion (BBT) representation of the protein molecule may be further generated to include a plurality of polymer chains, each of which including one or more amino acid residues in the protein molecule. For example, in some cases, the residues included in each polymer chain may be treated as a single rigid body. Accordingly, in some cases, the residues in a polymer chain (including its constituent atoms) may be translated and rotated as a group about a center of mass. That is, the residues in the polymer chain may share of a center of mass degree-of-freedom (DoF) as a group.

Figure 6B:
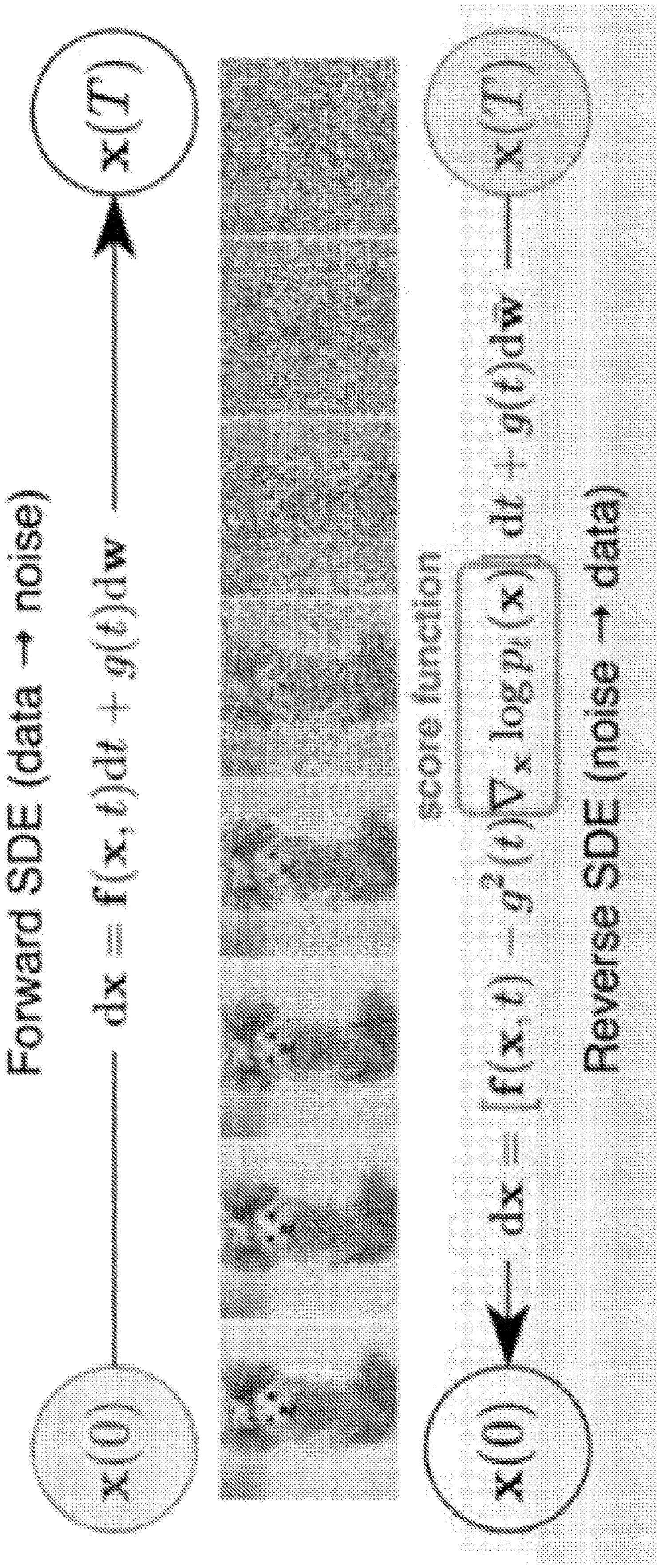
FIG. 6B depicts a schematic diagram illustrating an example of a diffusion framework, in accordance with some example embodiments.

FIG. 6B depicts a schematic diagram illustrating an example of a diffusion framework, in accordance with some example embodiments. In some cases, when implemented as the aforementioned diffusion model, the molecule design computation model 117 may perform a reverse diffusion process when denoising the initial three-dimensional structure of the protein molecule. Contrastingly, the forward diffusion process shown in FIG. 6B may be performed during the training of the diffusion model wherein noise is added successively to a ground-truth three-dimensional structure to generate a corrupted three-dimensional structure before the diffusion model is trained to perform a reverse diffusion to successively remove noise from the corrupted three-dimensional structure and restore the ground-truth three-dimensional structure.

Referring again to FIG. 6B, in some cases, the forward diffusion process may include the addition of noise (to perturb or corrupt the original data) in accordance to an increasing noise scale such that more noise is present in the three-dimensional structure of a protein molecule at each successive timestep. Contrastingly, the reverse diffusion process may include the removal of noise (to restore the original data) in accordance to a decreasing noise scale such that less noise is present in the three-dimensional structure of the protein molecule at each successive timestep. In some cases, the three-dimensional structure of a molecule, such as a protein molecule, may be generated by performing the reverse diffusion process on an initial three-dimensional structure of the molecule in which every constituent atom occupies a random position in three-dimensional space. As noted, the diffusion model may gradually, over a succession of timepoints, remove noise from the initial three-dimensional structure of the molecule. In instances where the initial three-dimensional structure of the molecule is rendered in a backbone torsion (BBT) representation, the initial three-dimensional structure of the molecule may include noise in the spatial arrangement of atoms in the sidechain and the backbone of the molecule. For instance, noise may be present in various degrees of freedom (DoF) along which an atom is able to move within the three-dimensional structure of the molecule. As such, the denoising of the initial three-dimensional structure, which includes modifying the positions of these atoms, may be limited to certain degrees of freedom including, for example, backbone translation $x_i=R^3$, backbone rotation $r_i=SO(3)$, and five torsion angles (one for oxygen (O) and four for the side chain angles):

$$(\theta^q)_{q=0}^4 = (\psi_O, \chi_1, \ldots, \chi_4)$$

and $\theta^q \in SO(2)$. Moreover, in some cases, the diffusion model may include multiple diffusion kernels, each of which modifying the initial three-dimensional structure of the molecule along a corresponding degree-of-freedom (DoF). In some cases, each diffusion kernel may be parameterized as a neural network. Furthermore, in some instances, each diffusion kernel may be parameterized as an equivariant neural network capable of generating a correct three-dimensional structure regardless of the orientation of the initial three-dimensional structure ingested as input.

FIG. 6B shows an example in which the diffusion model is implemented with a stochastic differential equation (SDE) score matching framework in which a stochastic differential equation (SDE) is applied to smoothly transform a sample from a complex data distribution, which in this case may be populated by the ground truth three-dimensional structures of various known protein molecules, to a corresponding sample in a noise distribution by the injection of noise. Meanwhile, a corresponding reverse-time stochastic differential equation (SDE) may be applied to restore the sample from the original complex data distribution (e.g., the original three-dimensional structure of a protein molecule) by the removal of noise. As a score-based generative model, the reverse stochastic differential equation (SDE), which governs the generative process of determining the three-dimensional structure of a protein molecule, may be learned by learning the score function (or the gradient of the log probability density function) of the data distribution. In this context, the score of the data distribution at each timepoint of the diffusion process, as determined by the score function, may correspond to a change in log data density. Learning the score function not only enables the approximation of the original complex data distribution but also the process to return a sample from a noise distribution to a corresponding sample in the complex data distribution. Unlike the probability density function of the data distribution, the score function can be computed without a normalizing constant, which requires determining the entire set of possible values and is oftentimes an intractable calculation. As described in more detail below, the score function may be estimated, for example, during the training of the stochastic differential equation (SDE) based diffusion model, by score matching. Moreover, it should be appreciated that a separate score function may exist for each degree-of-freedom (DoF). The score functions of the multiple degrees of freedoms (DoF) may be determined simultaneously during the training of the stochastic differential equation (SDE) based diffusion model.

Equation (2) below is an example of a forward stochastic differential equation (SDE) that transforms the complex data distribution from the original distribution x(0) to the noise distribution x(T). Equation (3) is an example of the corresponding reverse stochastic differential equation (SDE) that restores the original complex data distribution x(0) from the pure noise that is the known prior distribution x(T).

$$dx = f(x, t)dt + g(t)dw \tag{2}$$

$$d\bar{x} = \left[f(x, t) - g^2(t)\nabla_x \log p_t(x)\right]d\bar{t} + g(t)d\bar{w} \tag{3}$$

wherein f(·, t) is a vector-valued function called the drift coefficient of x(t) and g(t) is a scalar function known as the diffusion coefficient of x(t).

In some example embodiments, the training of the diffusion model in a stochastic differential equation (SDE) score matching framework may include learning a score-based model $s_\theta(x)$ that approximates, for each possible degree-of-freedom (DoF), the corresponding score function log $p_t$. In some cases, the score function $\nabla_x$ log $p_t(x)$ for each degree-of-freedom (DoF) may be approximated through score matching, which includes reducing or minimizing the difference (e.g., the Fisher divergence or the squared $l_2$ distance) between the score of the data distribution associated with the score-based model $s_\theta(x)$ and the ground-truth score of the data distribution, which in this case is the original distribution x(0). As noted, the score function log $p_t$ may define the changes in log data density across the original data distribution x(0). Accordingly, once the estimates of the score functions are computed, the three-dimensional structure of a molecule (e.g., a protein molecule) may be generated by sampling (e.g., Markov chain Monte Carlo sampling with Langevin dynamics) from the original data distribution x(0), as guided by the score functions. In doing so, the three-dimensional structure of a molecule may be generated by sampling from progressively higher density regions of the data distribution x(0), which are occupied by three-dimensional structures that are more consistent with ground truth three-dimensional molecular structures.

FIGS. 8A-8D depict graphs illustrating various examples of noise schedules, in accordance with some example embodiments. In some cases, the distribution of noise levels may correspond to a degree-of-freedom present in the representation of the protein molecule for the molecule design computation model 117 to modify the initial three-dimensional structure of the protein molecule. For example, in some cases, the proportion of torsion angles and residue identities in the protein molecule that are uncertain may decrease over time. Accordingly, at a starting timepoint (e.g., t=1), nearly every torsion angle in the protein molecule may be randomly oriented while the identity of almost every residue is ambiguous. At a second timepoint (e.g., t=0.5), after the representation of the protein molecule has undergone at least some denoising by the molecule design computation model 117, the identity of at least some residues may become more certain, thus decreasing the randomness of at least some torsion angles. At a third timepoint (e.g., t=0), the identity of nearly all residues may be certain, at which point the corresponding torsion angles are also known.

At 576, the molecule design engine 110 may determine, based at least on a modified representation of the protein molecule, one or more coordinates of each atom in the three-dimensional structure of the protein molecule. In some example embodiments, the molecule design engine 110 may determine, based at least on the plurality of frames of each amino acid residue in the modified backbone torsion (BBT) representation of the protein molecule, one or more coordinates (e.g., three-dimensional coordinates) of each atom in the three-dimensional structure of the protein molecule. For example, in some cases, the molecule design engine 110 may determine, based at least on the modified backbone torsion (BBT) representation of the protein molecule, one or more coordinates of the backbone atoms in the protein molecule. Thereafter, the molecule design engine 110 may determine, based at least on the coordinates of the backbone atoms in the protein molecule, one or more coordinates of the sidechain atoms in the protein molecule. An example of the algorithm for computing the coordinates of each atom in the three-dimensional structure of the protein molecule is shown in Table 4 above.

In view of the above-described implementations of subject matter this application discloses the following list of examples, wherein one feature of an example in isolation or more than one feature of said example taken in combination and, optionally, in combination with one or more features of one or more further examples are further examples also falling within the disclosure of this application:

Item 1: A computer-implemented method, comprising: receiving a molecular structure file specifying an initial three-dimensional structure of a molecule; determining, based at least on the molecular structure file, a plurality of coarse-grained nodes, each coarse-grained node corresponding to a structural body of two or more atoms (e.g., heavy atoms) forming an amino acid residue in the molecule; and determining, using a design computation model, a three-dimensional structure of the molecule, the design computation model determining the three-dimensional structure of the molecule by at least updating a position of one or more coarse-grained nodes in the initial three-dimensional structure of the molecule.

Item 2: The method of Item 1, wherein the structural body of two or more atoms excludes one or more elements forming the amino acid residue in the molecule.

Item 3: The method of any of Items 1 to 2, wherein the structural body of two or more atoms excludes one or more heavy atoms forming the amino acid residue in the molecule.

Item 4: The method of any of Items 1 to 3, further comprising: generating, for each coarse-grained node of the plurality of coarse-grained nodes, a geometric tensor embedding corresponding to a numerical representation of a rotation and/or a translation of the coarse-grained node.

Item 5: The method of Item 4, wherein the geometric tensor embedding includes a set of geometric tensors subjected to one or more rotations and/or translations.

Item 6: The method of Item 5, wherein the one or more rotations and/or translations correspond to one or more elements from a three-dimensional rotation group enumerating every possible nontrivial rotation within a three-dimensional space that cannot be further decomposed into a combination of two or more other rotations.

Item 7: The method of any of Items 1 to 6, wherein the design computation model comprises a machine learning model trained to perform successive updates to the position of the one or more coarse-grained nodes in the initial three-dimensional structure of the molecule.

Item 8: The method of Item 7, wherein the machine learning model includes a sequence of blocks, and wherein each block in the sequence of blocks performs an update to the position of the one or more coarse-grained nodes in the initial three-dimensional structure of the molecule.

Item 9: The method of any of Items 7 to 8, wherein the machine learning model includes a first block performing a first update to the position of the one or more coarse-grained nodes in the initial three-dimensional structure of the molecule, and wherein the machine learning model includes a second block performing a second update to the position of the one or more coarse-grained nodes in the initial three-dimensional structure of the molecule.

Item 10: The method of any of Items 7 to 9, wherein the machine learning model is a geometric deep learning model.

Item 11: The method of any of Items 7 to 10, wherein the machine learning model is an equivariant neural network.

Item 12: The method of any of Items 7 to 11, wherein the machine learning model is trained to reduce a loss function associated with each successive update to the position of the one or more coarse-grained nodes in the initial three-dimensional structure of the molecule.

Item 13: The method of Item 12, wherein the loss function is a frame aligned point error (FAPE) loss function and/or a structure violation loss function.

Item 14: The method of any of Items 7 to 13, wherein the machine learning model is trained to reduce an energy function associated with each successive update to the position of the one or more coarse-grained nodes in the initial three-dimensional structure of the protein sequence.

Item 15: The method of any of Items 7 to 14, wherein the machine learning model identifies when two or more three-dimensional structures with different orientations in three-dimensional space are identical.

Item 16: The method of any of Items 1 to 15, wherein the position of the one or more coarse-grained nodes in the initial three-dimensional structure of the protein is updated by at least rotating and/or translating the one or more coarse-grained nodes.

Item 17: The method of any of Items 1 to 16, wherein the position of the one or more coarse-grained nodes in the initial three-dimensional structure of the protein is updated without modifying a relative position of the two or more atoms included in the structural body corresponding to each coarse-grained node.

Item 18: The method of any of Items 1 to 17, wherein the plurality of coarse-grained nodes are determined such that a union of the plurality of coarse-grained nodes includes every atom included in the molecule.

Item 19: The method of any of Items 1 to 18, wherein the plurality of coarse-grained nodes are determined by at least grouping a plurality of atoms included in the molecule such that each atom in a coarse-grained node shares at least one covalent bond with another atom in a same coarse-grained node.

Item 20: The method of any of Items 1 to 19, wherein the plurality of coarse-grained nodes are determined such that each coarse-grained node includes a threshold quantity of atoms (e.g., heavy atoms) forming at least one structural body.

Item 21: The method of any of Items 1 to 20, wherein the three-dimensional structure of the protein is associated with one or more desirable properties.

Item 22: The method of any of Items 1 to 21, further comprising: determining, based at least on the three-dimensional structure of the protein, one or more properties of the molecule.

Item 23: The method of any of Items 1 to 22, further comprising: generating, based at least on a first sequence of amino acid residues, a second sequence of amino acid residues comprising the molecule; and generating, based at least on the second sequence of amino acid residues or a third sequence of amino acid residues, a fourth sequence of amino acid residues.

Item 24: The method of Item 23, further comprising: determining, based at least on the three-dimensional structure of the molecule, that the second sequence of amino acid residues exhibits a desirable three-dimensional structure and/or a desirable property; and in response to determining that the second sequence of amino acid residues exhibits the desirable three-dimensional structure and/or the desirable property, generating, based at least on the second sequence of amino acid residues, the fourth sequence of amino acid residues.

Item 25: The method of Item 24, further comprising: determining, based at least on the three-dimensional structure of the molecule, that the second sequence of amino acid residues lacks a desirable three-dimensional structure or a desirable property; and in response to determining that the second sequence of amino acid residues lacks the desirable three-dimensional structure or the desirable property, generating, based at least on the third sequence of amino acid residues, the fourth sequence of amino acid residues.

Item 26: The method of any of Items 1 to 25, wherein the molecule is a protein molecule, a small molecule, an ion, a nucleic acid, a polysaccharide, or a glycolipid.

Item 27: The method of any of Items 1 to 26, wherein the structural body is a rigid body or a flexible body of the two or more atoms forming the amino acid residue in the molecule.

Item 28: A system, comprising: at least one data processor; and at least one memory storing instructions, which when executed by the at least one data processor, result in operations comprising the method of any of Items 1 to 27.

Item 29: A non-transitory computer readable medium storing instructions, which when executed by at least one data processor, result in operations comprising the method of any of Items 1 to 27.

Item 30: A computer-implemented method, comprising: receiving a molecular structure file specifying an initial three-dimensional structure of a protein molecule comprising a first sequence of amino acid residues; determining, based at least on the molecular structure file, a representation of the protein molecule that includes a plurality of frames for each amino acid residue in the first sequence of amino acid residues, the plurality of frames for each amino acid residue including a first set of frames specifying a geometric state a backbone of the amino acid residue, and the plurality of frames of each amino acid residue further including a second set of frames specifying one or more torsion angles in a sidechain of the amino acid residue; and generating a first three-dimensional structure of the protein molecule by at least applying a design computation model to modify the representation of the protein molecule.

Item 31: The method of Item 30, wherein each frame of the plurality of frames correspond to a degree-of-freedom for the design computation model to update the initial three-dimensional structure of the protein molecule.

Item 32: The method of any of Items 30 to 31, wherein the first set of frames include a first frame comprising an affine transformation matrix specifying a rotation and a translation of the backbone of the amino acid residue.

Item 33: The method of Item 32, wherein the affine transformation matrix includes a rotation matrix specifying the rotation of the backbone of the amino acid residue, and wherein the affine transformation matrix further includes a displacement vector specifying the translation of the backbone of the amino acid residue.

Item 34: The method of any of Items 32 to 33, wherein the first set of frames further includes a second frame specifying a torsion angle in the backbone of the amino acid residue.

Item 35: The method of Item 34, wherein the torsion angle is associated with a rotatable bond between an alpha carbon ($C_\alpha$) atom and a carbonyl group in the backbone of the amino acid residue.

Item 36: The method of any of Items 30 to 35, wherein the first set of frames include a first frame specifying a first torsion angle in the backbone of the amino acid residue, and wherein the first set of frames further includes a second frame specifying a second torsion angle in the backbone of the amino acid residue.

Item 37: The method of Item 36, wherein the first torsion angle is associated with a first rotatable bond between an alpha carbon ($C_\alpha$) atom and a carbon (C) atom in the backbone in the backbone of the amino acid residue, and wherein the second torsion angle is associated with a second rotatable bond between the alpha carbon ($C_\alpha$) atom and a nitrogen (N) atom in the backbone of the of the amino acid residue.

Item 38: The method of Item 37, wherein the first set of frames further includes a third frame specifying a third torsion angle present in the backbone of the amino acid residue.

Item 39: The method of Item 38, wherein the third torsion angle is associated with a third rotatable bond between the carbon (C) atom and the nitrogen (N) atom in the backbone of the amino acid residue.

Item 40: The method of any of Items 30 to 39, further comprising: determining, based at least on the modified representation of the protein molecule, one or more coordinates of each atom comprising the first three-dimensional structure of the protein molecule.

Item 41: The method of Item 40, wherein the one or more coordinates of each atom in the first three-dimensional structure of the protein molecule is determined based at least on the plurality of frames associated with each amino acid residue included in the modified representation of the protein molecule.

Item 42: The method of Item 41, wherein the one or more coordinates of each atom in the first three-dimensional structure of the protein molecule is determined by at least determining the one or more coordinates of a plurality of backbone atoms in the protein molecule.

Item 43: The method of Item 42, wherein the one or more coordinates of each atom in the first three-dimensional structure of the protein molecule is further determined by at least determining, based on the one or more coordinates of the plurality of backbone atoms in the protein molecule, the one or more coordinates of a plurality of sidechain atoms in the protein molecule.

Item 44: The method of any of Items 30 to 43, wherein the design computation model comprises a machine learning model trained to generate the first three-dimensional structure of the protein molecule by at least to denoising the initial three-dimensional structure of the protein molecule.

Item 45: The method of Item 44, wherein the machine learning model denoises the initial three-dimensional structure of the protein molecule by at least performing a sequence of updates to the representation of the protein molecule.

Item 46: The method of Item 45, wherein the machine learning model is trained to reduce a loss function associated with each successive update to the initial three-dimensional structure of the protein molecule.

Item 47: The method of Item 46, wherein the loss function is a frame aligned point error (FAPE) loss function and/or a structure violation loss function.

Item 48: The method of any of Items 45 to 46, wherein the machine learning model is trained to reduce an energy function associated with each successive update successive update to the initial three-dimensional structure of the protein molecule.

Item 49: The method of any of Items 30 to 48, wherein the machine learning model is a diffusion model that removes, at each timestep of a plurality of successive timesteps, a portion of noise present in the initial three-dimensional structure of the protein molecule.

Item 50: The method of Item 49, wherein the diffusion model performs a first update to the representation of the protein molecule in order to remove a first quantity of noise present in the initial three-dimensional structure of the protein molecule, and wherein the diffusion model further performs a second update to the representation of the protein molecule in order to remove a second quantity of noise present in the initial three-dimensional structure of the protein molecule.

Item 51: The method of Item 50, wherein the diffusion model further adds a third quantity of noise prior to performing the second update to remove the second quantity of noise and a fourth quantity of noise subsequent to performing the second update to remove the second quantity of noise, and wherein the third quantity of noise and the fourth quantity of noise are determined based on a noise schedule defining a distribution of noise levels that is added across the plurality of successive timesteps.

Item 52: The method of Item 51, wherein the distribution of noise levels corresponds to a degree-of-freedom present in the representation of the protein molecule for the computation model to modify the initial three-dimensional structure of the protein molecule.

Item 53: The method of any of Items 49 to 52, wherein update performed by the diffusion model generates an output that is equivariant to special Euclidean group SE(3) transformations.

Item 54: The method of any of Items 30 to 53, wherein the modifying of the representation of the protein molecule includes updating the first set of frames to alter the geometric state of the backbone of one or more amino acid residues in the protein molecule.

Item 55: The method of any of Items 30 to 54, wherein the modifying of the representation of the protein molecule includes updating the second set of frames to alter the one or more torsion angles in the sidechain of one or more amino acid residues in the protein molecule.

Item 56: The method of any of Items 30 to 55, wherein the first three-dimensional structure of the protein molecule is associated with one or more desirable properties.

Item 57: The method of any of Items 30 to 56, wherein the first three-dimensional structure of the protein molecule is configured for one or more downstream tasks.

Item 58: The method of Item 57, wherein the one or more downstream tasks include determining, based at least on the first three-dimensional structure of the protein molecule, one or more properties of the protein molecule.

Item 59: The method of any of Items 30 to 58, further comprising: determining, based at least on the first three-dimensional structure of the protein molecule, that the first sequence of amino acid residues exhibits a desirable three-dimensional structure and/or a desirable property; and in response to determining that the first sequence of amino acid residues exhibits the desirable three-dimensional structure and/or the desirable property, generating, based at least on the first sequence of amino acid residues, a second sequence of amino acid residues for a different protein molecule.

Item 60: The method of any of Items 30 to 59, wherein the representation of the protein molecule further includes, for each position in a sequence of amino acid residue forming the protein molecule, a logic vector indicating an identity of an amino acid residue occupying the position by at least enumerating a probability distribution across a set of possible amino acid residues occupying the position.

Item 61: The method of Item 60, wherein the design computation model further generates the first three-dimensional structure of the protein molecule by modifying an identity of at least one amino acid residue in the first sequence of residues while modifying the first set of frames and/or the second set of frames associated with the at least one amino acid residue.

Item 62: The method of any of Items 30 to 61, wherein the initial three-dimensional structure of the protein molecule includes noise in an identity of each amino acid residue and/or a spatial arrangement of a plurality of atoms forming each amino acid, and wherein the noise is removed by the design computation model modifying the representation of the protein molecule.

Item 63: The method of Item 62, wherein the noise is Gaussian noise.

Item 64: The method of any of Items 30 to 63, wherein the representation of the protein molecule is further generated to include a plurality of polymer chains, and wherein each polymer chain includes one or more amino acid residues from the first sequence of amino acid residues.

Item 65: The method of Item 64, wherein the modifying of the representation of the protein molecule includes modifying a position of the one or more amino acid in each polymer chain as a group.

Item 66: A system, comprising: at least one data processor; and at least one memory storing instructions, which when executed by the at least one data processor, result in operations comprising the method of any of Items 30 to 65.

Item 67: A non-transitory computer readable medium storing instructions, which when executed by at least one data processor, result in operations comprising the method of any of Items 30 to 65.

Figure 9:
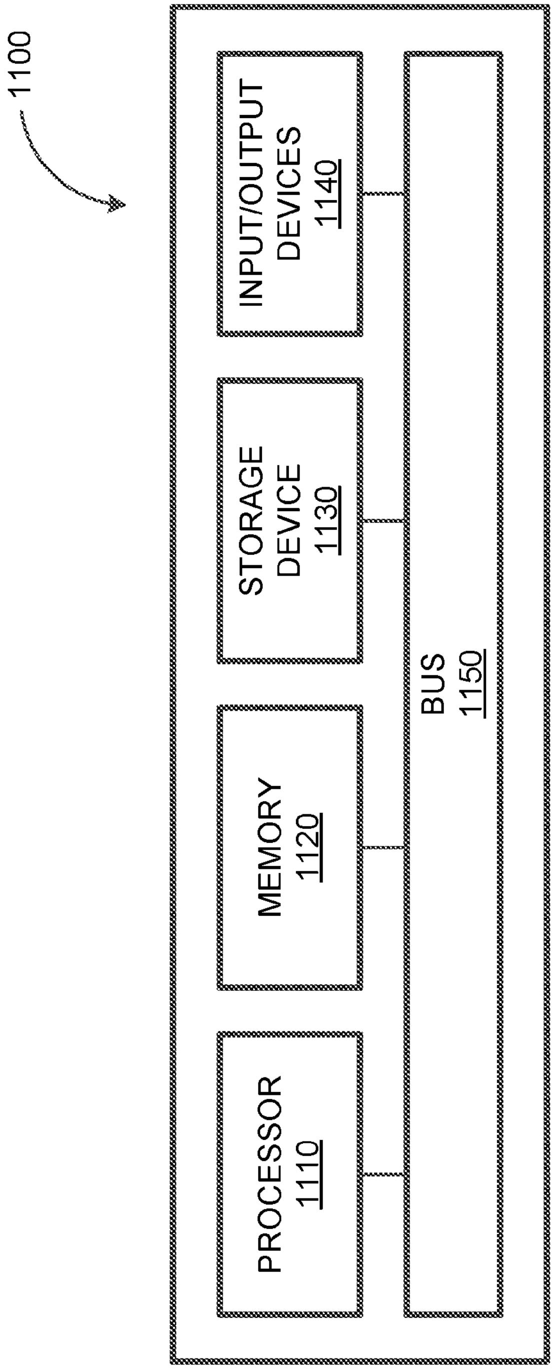
FIG. 9 depicts a block diagram illustrating an example of a computing system, in accordance with some example embodiments.

FIG. 9 depicts a block diagram illustrating an example of computing system 1100, in accordance with some example embodiments. Referring to FIGS. 1-9, the computing system 1100 may be used to implement the molecule design engine 110, the molecular analysis engine 120, the client device 130, and/or any components therein.

As shown in FIG. 9, the computing system 1100 can include a processor 1110, a memory 1120, a storage device 1130, and input/output devices 1140. The processor 1110, the memory 1120, the storage device 1130, and the input/output devices 1140 can be interconnected via a system bus 1150. The processor 1110 is capable of processing instructions for execution within the computing system 1100. Such executed instructions can implement one or more components of, for example, the molecule design engine 110, the molecular analysis engine 120, the client device 130, and/or the like. In some example embodiments, the processor 1110 can be a single-threaded processor. Alternatively, the processor 1110 can be a multi-threaded processor. The processor 1110 is capable of processing instructions stored in the memory 1120 and/or on the storage device 1130 to display graphical information for a user interface provided via the input/output device 1140.

The memory 1120 is a computer readable medium such as volatile or non-volatile that stores information within the computing system 1100. The memory 1120 can store data structures representing configuration object databases, for example. The storage device 1130 is capable of providing persistent storage for the computing system 1100. The storage device 1130 can be a floppy disk device, a hard disk device, an optical disk device, or a tape device, or other suitable persistent storage means. The input/output device 1140 provides input/output operations for the computing system 1100. In some example embodiments, the input/output device 1140 includes a keyboard and/or pointing device. In various implementations, the input/output device 1140 includes a display unit for displaying graphical user interfaces.

According to some example embodiments, the input/output device 1140 can provide input/output operations for a network device. For example, the input/output device 1140 can include Ethernet ports or other networking ports to communicate with one or more wired and/or wireless networks (e.g., a local area network (LAN), a wide area network (WAN), the Internet).

In some example embodiments, the computing system 1100 can be used to execute various interactive computer software applications that can be used for organization, analysis and/or storage of data in various formats. Alternatively, the computing system 1100 can be used to execute any type of software applications. These applications can be used to perform various functionalities, e.g., planning functionalities (e.g., generating, managing, editing of spreadsheet documents, word processing documents, and/or any other objects, etc.), computing functionalities, communications functionalities, etc. The applications can include various add-in functionalities or can be standalone computing products and/or functionalities. Upon activation within the applications, the functionalities can be used to generate the user interface provided via the input/output device 1140. The user interface can be generated and presented to a user by the computing system 1100 (e.g., on a computer screen monitor, etc.).

One or more aspects or features of the subject matter described herein can be realized in digital electronic circuitry, integrated circuitry, specially designed ASICs, field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including acoustic, speech, or tactile input. Other possible input devices include touch screens or other touch-sensitive devices such as single or multi-point resistive or capacitive track pads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A system, comprising:

at least one data processor; and at least one memory storing instructions, which when executed by the at least one data processor, result in operations comprising:

receiving a molecular structure file specifying an initial three-dimensional structure of a protein molecule comprising a sequence of amino acid residues;

determining, based at least on the molecular structure file, a representation of the protein molecule that includes a plurality of frames for each amino acid residue in the sequence of amino acid residues, wherein the plurality of frames for each amino acid residue includes a first set of frames specifying a geometric state a backbone of the amino acid residue, and wherein the first set of frames includes a rotation matrix specifying the rotation of the backbone of the amino acid residue or a displacement vector specifying the translation of the backbone of the amino acid residue, and wherein the representation of the protein molecule further includes, for each position in a sequence of amino acid residue forming the protein molecule, a probability distribution across a set of possible amino acid residues occupying the position; and generating a three-dimensional structure of the protein molecule by at least applying a design computation model to modify the representation of the protein molecule, wherein the design computation model modifies the plurality of frames while also modifying the probability distribution such that a probability of the position being occupied by each possible type of amino acid residue sums to 1.

2. The system of claim 1, wherein each frame of the plurality of frames corresponds to a degree-of-freedom for the design computation model to update the initial three-dimensional structure of the protein molecule.

3. The system of claim 1, wherein the rotation matrix or the displacement vector comprise a first frame of the first set of frames, and wherein the first set of frames further includes a second frame specifying a torsion angle in the backbone of the amino acid residue.

4. The system of claim 1, wherein the first set of frames includes a first frame specifying a first torsion angle in the backbone of the amino acid residue, and wherein the first set of frames further includes a second frame specifying a second torsion angle in the backbone of the amino acid residue.

5. The system of claim 4, wherein the first torsion angle is associated with a first rotatable bond between an alpha carbon ($C_\alpha$) atom and a carbon (C) atom in the backbone in the backbone of the amino acid residue, and wherein the second torsion angle is associated with a second rotatable bond between the alpha carbon ($C_\alpha$) atom and a nitrogen (N) atom in the backbone of the of the amino acid residue.

6. The system of claim 5, wherein the first set of frames further includes a third frame specifying a third torsion angle present in the backbone of the amino acid residue, and wherein the third torsion angle is associated with a third rotatable bond between the carbon (C) atom and the nitrogen (N) atom in the backbone of the amino acid residue.

7. The system of claim 1, further comprising:

determining, based at least on the plurality of frames associated with each amino acid residue included in the modified representation of the protein molecule, one or more coordinates of a plurality of backbone atoms in the protein molecule; and determining, based on the one or more coordinates of the plurality of backbone atoms in the protein molecule, one or more coordinates of a plurality of sidechain atoms in the protein molecule.

8. The system of claim 1, wherein the design computation model is trained to generate the three-dimensional structure of the protein molecule by at least to denoising the initial three-dimensional structure of the protein molecule.

9. The system of claim 1, wherein the design computation model denoises the initial three-dimensional structure of the protein molecule by at least performing a sequence of updates to the representation of the protein molecule.

10. The system of claim 1, wherein the design computation model is trained to reduce a loss function and/or an energy function associated with each successive update to the representation of the protein molecule.

11. The system of claim 1, wherein the design computation model comprises a diffusion model that removes, at each timestep of a plurality of successive timesteps, a portion of noise present in the initial three-dimensional structure of the protein molecule.

12. The system of claim 11, wherein the diffusion model performs a first update to the representation of the protein molecule in order to remove a first quantity of noise present in the initial three-dimensional structure of the protein molecule, and wherein the diffusion model further performs a second update to the representation of the protein molecule in order to remove a second quantity of noise present in the initial three-dimensional structure of the protein molecule.

13. The system of claim 12, wherein the diffusion model further adds a third quantity of noise prior to performing the second update to remove the second quantity of noise and a fourth quantity of noise subsequent to performing the second update to remove the second quantity of noise, and wherein the third quantity of noise and the fourth quantity of noise are determined based on a noise schedule defining a distribution of noise levels that is added across the plurality of successive timesteps.

14. The system of claim 13, wherein the distribution of noise levels corresponds to a degree-of-freedom present in the representation of the protein molecule for the computation model to modify the initial three-dimensional structure of the protein molecule.

15. The system of claim 11, wherein each update performed by the diffusion model generates an output that is equivariant to special Euclidean group SE(3) transformations.

16. The system of claim 1, wherein the modifying of the representation of the protein molecule includes updating the first set of frames to alter the geometric state of the backbone of one or more amino acid residues in the protein molecule.

17. The system of claim 1, wherein the plurality of frames for each amino acid residue further includes a second set of frames specifying one or more torsion angles in a sidechain of the amino acid residue, and wherein the modifying of the representation of the protein molecule includes updating the second set of frames to alter the one or more torsion angles in the sidechain of one or more amino acid residues in the protein molecule.

18. The system of claim 1, wherein the three-dimensional structure of the protein molecule is associated with one or more properties.

19. The system of claim 1, wherein the three-dimensional structure of the protein molecule is configured for one or more downstream tasks.

20. The system of claim 1, further comprising:

determining, based at least on the three-dimensional structure of the protein molecule, that the sequence of amino acid residues exhibits a three-dimensional structure and/or a property; and in response to determining that the sequence of amino acid residues exhibits the three-dimensional structure and/or the property, generating, based at least on the sequence of amino acid residues, a sequence of amino acid residues for a different protein molecule.

21. The system of claim 1, wherein the representation of the protein molecule further includes, for each position in a sequence of amino acid residue forming the protein molecule, a logit vector enumerating the probability distribution across the set of possible amino acid residues occupying the position.

22. The system of claim 1, wherein the initial three-dimensional structure of the protein molecule includes noise in an identity of each amino acid residue and/or a spatial arrangement of a plurality of atoms forming each amino acid, and wherein the noise is removed by the design computation model modifying the representation of the protein molecule.

23. The system of claim 1, wherein the representation of the protein molecule is further generated to include a plurality of polymer chains, wherein each polymer chain includes one or more amino acid residues from the sequence of amino acid residues, and wherein the representation of the protein molecule is modified by the protein design computation model modifying a position of the one or more amino acid in each polymer chain as a group.

24. A computer-implemented method, comprising:

receiving a molecular structure file specifying an initial three-dimensional structure of a protein molecule comprising a sequence of amino acid residues;

determining, based at least on the molecular structure file, a representation of the protein molecule that includes a plurality of frames for each amino acid residue in the sequence of amino acid residues, wherein the plurality of frames for each amino acid residue includes a first set of frames specifying a geometric state a backbone of the amino acid residue, and wherein the first set of frames includes a rotation matrix specifying the rotation of the backbone of the amino acid residue or a displacement vector specifying the translation of the backbone of the amino acid residue, and wherein the representation of the protein molecule further includes, for each position in a sequence of amino acid residue forming the protein molecule, a probability distribution across a set of possible amino acid residues occupying the position; and generating a three-dimensional structure of the protein molecule by at least applying a design computation model to modify the representation of the protein molecule, wherein the design computation model modifies the plurality of frames while also modifying the probability distribution such that a probability of the position being occupied by each possible type of amino acid residue sums to 1.

25. A non-transitory computer readable medium storing instructions, which when executed by at least one data processor coupled with a computing system, result in operations comprising:

receiving a molecular structure file specifying an initial three-dimensional structure of a protein molecule comprising a sequence of amino acid residues;

determining, based at least on the molecular structure file, a representation of the protein molecule that includes a plurality of frames for each amino acid residue in the sequence of amino acid residues, wherein the plurality of frames for each amino acid residue includes a first set of frames specifying a geometric state a backbone of the amino acid residue, and wherein the first set of frames includes a rotation matrix specifying the rotation of the backbone of the amino acid residue or a displacement vector specifying the translation of the backbone of the amino acid residue, and wherein the representation of the protein molecule further includes, for each position in a sequence of amino acid residue forming the protein molecule, a probability distribution across a set of possible amino acid residues occupying the position; and generating a three-dimensional structure of the protein molecule by at least applying a design computation model to modify the representation of the protein molecule, wherein the design computation model modifies the plurality of frames while also modifying the probability distribution such that a probability of the position being occupied by each possible type of amino acid residue sums to 1.

26. The system of claim 19, wherein the one or more downstream tasks include determining, based at least on the three-dimensional structure of the protein molecule, one or more properties of the protein molecule.

27. The system of claim 19, wherein the one or more downstream tasks include docking another molecule to the three-dimensional structure of the protein molecule.

28. The system of claim 19, wherein the degree-of-freedom associated with the frame imposes one or more constraints on a spatial range within which the design computation model is able to move one or more atoms comprising the corresponding amino acid residue when updating the initial three-dimensional structure of the protein molecule.

29. The system of claim 1, wherein the probability distribution associated with each position in the sequence of amino acid residues comprises a probability simplex occupying a (D−1) dimensional space where the set of possible amino acid residues includes a D quantity of possible amino acid residues.

* * * * *